(12) United States Patent
Kappe et al.

(10) Patent No.: US 8,168,166 B2
(45) Date of Patent: May 1, 2012

(54) LIVE GENETICALLY ATTENUATED MALARIA VACCINE

(75) Inventors: Stefan H. I. Kappe, Seattle, WA (US); Kai-Uwe C. Matuschewski, Berlin (DE); Ann-Kristin Mueller, Dossenheim (DE); Kelley van Buskirk, Columbia City, IN (US); Mehdi Labaied, Bainbridge Island, WA (US); Ahmed Sayed Ibrahim Aly, Seattle, WA (US); Alan Frederick Cowman, Melbourne (AU); Alexander Gerd Maier, Coburg (AU)

(73) Assignees: Seattle Biomedical Research Institute, Seattle, WA (US); Walter and Eliza Hall Institute of Medical Research, Parkville (AU)

( * ) Notice: Subject to any disclaimer, the term of this patent is extended or adjusted under 35 U.S.C. 154(b) by 590 days.

(21) Appl. No.: 12/116,159

(22) Filed: May 6, 2008

(65) Prior Publication Data

US 2011/0033502 A1 Feb. 10, 2011

Related U.S. Application Data

(63) Continuation-in-part of application No. 10/583,186, filed as application No. PCT/US2004/043023 on Dec. 20, 2004, now Pat. No. 7,718,165.

(60) Provisional application No. 60/631,228, filed on Nov. 26, 2004, provisional application No. 60/531,479, filed on Dec. 19, 2003.

(51) Int. Cl.
*A01N 65/00* (2009.01)
*A61K 39/00* (2006.01)
*A61K 48/00* (2006.01)
*C12N 1/10* (2006.01)

(52) U.S. Cl. .................. 424/93.1; 424/93.2; 424/93.21; 424/93.7; 424/265.1; 435/258.2

(58) Field of Classification Search .................. None
See application file for complete search history.

(56) References Cited

U.S. PATENT DOCUMENTS

| 4,479,935 | A * | 10/1984 | Metianu et al. | 424/282.1 |
| 7,122,179 | B2 * | 10/2006 | Kappe et al. | 424/93.1 |
| 7,550,138 | B1 | 6/2009 | Waters | |
| 7,718,165 | B2 * | 5/2010 | Kappe et al. | 424/93.1 |
| 2005/0208078 | A1 * | 9/2005 | Hoffman et al. | 424/272.1 |
| 2005/0266017 | A1 * | 12/2005 | Druilhe et al. | 424/191.1 |

FOREIGN PATENT DOCUMENTS

WO 95/07094 A1 3/1995

OTHER PUBLICATIONS

Thathy, V., and R. Ménard, "Gene Targeting in *Plasmodium berghei*," in D. Doolan (ed.) Methods in Molecular Medicine, vol. 72, "Malaria Methods and Protocols," Humana Press, Totowa, New Jersey, 2002, pp. 317-331.
Matuschewski, K., et al., "Infectivity-Associated Changes in the Transcriptional Repertoire of the Malaria Parasite Sporozoite Stage," Journal of Biological Chemistry 277(44):41948-41953, 2002.
Ménard, R., et al., "Circumsporozoite Protein is Required for Development of Malaria Sporozoites in Mosquitoes," Nature 385(23):336-340, 1997.
Ménard, G., and C. Janse," Gene Targeting in Malaria Parasites," Methods: A Companion to Methods in Enzymology 13:148-157, 1997.
Mueller, A.-K., et al., "Genetically Modified *Plasmodium* Parasites as a Protective Experimental Malaria Vaccine," Nature 433(13):164-167, 2005.
Sultan, A.A., et al., "TRAP is Necessary for Gliding Motility and Infectivity of *Plasmodium* Sporozoites," Cell 90:511-522, 1997.
Van Dijk, M.R., et al., "A Central Role for P48/45 in Malaria Parasite Male Gamete Fertility," Cell 104:153-164, 2001.
Vos, H.-J., and E. Hauben, Letter sent on behalf of Leiden University Medical Center and Stichting Katholieke Universiteit Nijmegen regarding U.S. Patent No. 7,550,138, mailed May 3, 2011, 2 pages.

* cited by examiner

*Primary Examiner* — Albert Navarro
(74) *Attorney, Agent, or Firm* — Christensen O'Connor Johnson Kindness PLLC

(57) ABSTRACT

Method for inoculating a vertebrate host against malaria, by administering to the host a live *Plasmodium* organism that is genetically engineered to disrupt a liver-stage-specific gene function.

1 Claim, 4 Drawing Sheets

SEQUENCE LISTING

<160> NUMBER OF SEQ ID NOS: 99

<210> SEQ ID NO 1
<211> LENGTH: 31
<212> TYPE: DNA
<213> ORGANISM: Plasmodium berghei

<400> SEQUENCE: 1
gggtacccgc attagcataa catctcattg g                                      31

<210> SEQ ID NO 2
<211> LENGTH: 31
<212> TYPE: DNA
<213> ORGANISM: Plasmodium berghei

<400> SEQUENCE: 2
caagcttgct ttcatatatt tgttatttgt c                                      31

<210> SEQ ID NO 3
<211> LENGTH: 27
<212> TYPE: DNA
<213> ORGANISM: Plasmodium berghei

<400> SEQUENCE: 3
ggaattccca tatgtttgtg taacatc                                           27

<210> SEQ ID NO 4
<211> LENGTH: 31
<212> TYPE: DNA
<213> ORGANISM: Plasmodium berghei

<400> SEQUENCE: 4
ctctagagtg tgcttaaatg tttctttaaa c                                      31

<210> SEQ ID NO 5
<211> LENGTH: 31
<212> TYPE: DNA
<213> ORGANISM: Plasmodium berghei

<400> SEQUENCE: 5
cggaattcat catattacta attttcgggg g                                      31

```
<210> SEQ ID NO 6
<211> LENGTH: 36
<212> TYPE: DNA
<213> ORGANISM: Plasmodium berghei

<400> SEQUENCE: 6
tccccgcggt tattccatgt tataaacgtt atttcc                              36

<210> SEQ ID NO 7
<211> LENGTH: 23
<212> TYPE: DNA
<213> ORGANISM: Plasmodium berghei

<400> SEQUENCE: 7
cccgcacgga cgaatccaga tgg                                            23

<210> SEQ ID NO 8
<211> LENGTH: 32
<212> TYPE: DNA
<213> ORGANISM: Plasmodium berghei

<400> SEQUENCE: 8
cccaagctta gtttgcatat acggctgctt cc                                  32

<210> SEQ ID NO 9
<211> LENGTH: 31
<212> TYPE: DNA
<213> ORGANISM: Plasmodium berghei

<400> SEQUENCE: 9
cggaattctg gattcatttt ttgatgcatg c                                   31

<210> SEQ ID NO 10
<211> LENGTH: 21
<212> TYPE: DNA
<213> ORGANISM: Plasmodium berghei

<400> SEQUENCE: 10
gtaatacgac tcactatagg c                                              21

<210> SEQ ID NO 11
<211> LENGTH: 29
<212> TYPE: DNA
<213> ORGANISM: Plasmodium berghei

<400> SEQUENCE: 11
gaattctgga ttcatttttt gatgcatgc                                      29

<210> SEQ ID NO 12
<211> LENGTH: 34
<212> TYPE: DNA
<213> ORGANISM: Plasmodium berghei

<400> SEQUENCE: 12
ggggtacctt tattcagacg taataattat gtgc                                34

<210> SEQ ID NO 13
<211> LENGTH: 38
<212> TYPE: DNA
<213> ORGANISM: Plasmodium berghei

<400> SEQUENCE: 13
aaaactgcag ataattcatt atgagtagtg taattcag                            38
```

```
<210> SEQ ID NO 14
<211> LENGTH: 34
<212> TYPE: DNA
<213> ORGANISM: Plasmodium falciparum

<400> SEQUENCE: 14 cccccaagctt aagtttgcat atacggctgc ttcc                                34

<210> SEQ ID NO 15
<211> LENGTH: 27
<212> TYPE: DNA
<213> ORGANISM: Plasmodium falciparum

<400> SEQUENCE: 15
gagtaatata atgtgtaatg catatgg                                         27

<210> SEQ ID NO 16
<211> LENGTH: 24
<212> TYPE: DNA
<213> ORGANISM: Plasmodium falciparum

<400> SEQUENCE: 16
gagaccttca tttcaaaaag gaag                                            24

<210> SEQ ID NO 17
<211> LENGTH: 30
<212> TYPE: DNA
<213> ORGANISM: Plasmodium falciparum

<400> SEQUENCE: 17
caaatgaaaa cttggaaata atcagacgag                                      30

<210> SEQ ID NO 18
<211> LENGTH: 32
<212> TYPE: DNA
<213> ORGANISM: Plasmodium falciparum

<400> SEQUENCE: 18
gtattatgct taaattggaa aaaagtttga ag                                   32

<210> SEQ ID NO 19
<211> LENGTH: 39
<212> TYPE: DNA
<213> ORGANISM: Plasmodium yoelii

<400> SEQUENCE: 19
ggggtaccgt gcaatgtgaa aatgataatg ctcgataag                            39

<210> SEQ ID NO 20
<211> LENGTH: 42
<212> TYPE: DNA
<213> ORGANISM: Plasmodium yoelii

<400> SEQUENCE: 20
gcccaagctt ttttctttct taaatacaaa aaaataattt at                        42

<210> SEQ ID NO 21
<211> LENGTH: 40
<212> TYPE: DNA
<213> ORGANISM: Plasmodium yoelii

<400> SEQUENCE: 21
ggactagtcc agctataaac tccgaaacat cgaattatgt                           40
```

```
<210> SEQ ID NO 22
<211> LENGTH: 40
<212> TYPE: DNA
<213> ORGANISM: Plasmodium yoelii

<400> SEQUENCE: 22
tccccgcggg catcgcgttg atgcttttgg gaattattga                          40

<210> SEQ ID NO 23
<211> LENGTH: 31
<212> TYPE: DNA
<213> ORGANISM: Plasmodium yoelii

<400> SEQUENCE: 23
ggctacgtcc cgcacggacg aatccagatg g                                  31

<210> SEQ ID NO 24
<211> LENGTH: 31
<212> TYPE: DNA
<213> ORGANISM: Plasmodium yoelii

<400> SEQUENCE: 24 caccctta ta accatcatta tctactttc c                                  31

<210> SEQ ID NO 25
<211> LENGTH: 28
<212> TYPE: DNA
<213> ORGANISM: Plasmodium yoelii

<400> SEQUENCE: 25 ctcttttgg gagtcaaaaa cggtatgc                                       28

<210> SEQ ID NO 26
<211> LENGTH: 30
<212> TYPE: DNA
<213> ORGANISM: Plasmodium yoelii

<400> SEQUENCE: 26
cgcattatat gagttcattt tacacaatcc                                    30

<210> SEQ ID NO 27
<211> LENGTH: 27
<212> TYPE: DNA
<213> ORGANISM: Plasmodium yoelii

<400> SEQUENCE: 27
ggtaaaccac ggcacgttcc tatgttt                                       27

<210> SEQ ID NO 28
<211> LENGTH: 29
<212> TYPE: DNA
<213> ORGANISM: Plasmodium yoelii

<400> SEQUENCE: 28
cttgatttat cagcattgtt aatatgccc                                     29

<210> SEQ ID NO 29
<211> LENGTH: 15
<212> TYPE: PRT
<213> ORGANISM: Plasmodium yoelii

<400> SEQUENCE: 29

Leu Arg Gly Arg Gln Val Gln Gln Ser Phe Asn His Ser Ala Ser
```

<210> SEQ ID NO 30
<211> LENGTH: 44
<212> TYPE: DNA
<213> ORGANISM: Plasmodium falciparum

<400> SEQUENCE: 30
ggaccgctcg agttttatg tcgaataacg ctttacaaac aatt                44

<210> SEQ ID NO 31
<211> LENGTH: 38
<212> TYPE: DNA
<213> ORGANISM: Plasmodium falciparum

<400> SEQUENCE: 31
ggaccctcga gtcaacgttt gtagtcgatg gcttctgg                     38

<210> SEQ ID NO 32
<211> LENGTH: 29
<212> TYPE: DNA
<213> ORGANISM: Plasmodium falciparum

<400> SEQUENCE: 32
ggaccccgcg gaaaactttc agttttcac                               29

<210> SEQ ID NO 33
<211> LENGTH: 31
<212> TYPE: DNA
<213> ORGANISM: Plasmodium falciparum

<400> SEQUENCE: 33
ggaccgttaa cctcccaata ttctcttgtc c                            31

<210> SEQ ID NO 34
<211> LENGTH: 43
<212> TYPE: DNA
<213> ORGANISM: Plasmodium falciparum

<400> SEQUENCE: 34
ggaccaccgg tagcctaggg acggattagt tgaaaataaa tcc               43

<210> SEQ ID NO 35
<211> LENGTH: 33
<212> TYPE: DNA
<213> ORGANISM: Plasmodium falciparum

<400> SEQUENCE: 35
ggaccgggcg cccgggtttc ccatcaacta agg                          33

<210> SEQ ID NO 36
<211> LENGTH: 42
<212> TYPE: DNA
<213> ORGANISM: Plasmodium falciparum

<400> SEQUENCE: 36
ggaccgctcg agttttatg gcttcgtacc cctgccatca ac                 42

<210> SEQ ID NO 37
<211> LENGTH: 35
<212> TYPE: DNA
<213> ORGANISM: Plasmodium falciparum

<400> SEQUENCE: 37
ggaccgctcg agtcagttag cctcccccat ctccc                          35

<210> SEQ ID NO 38
<211> LENGTH: 52
<212> TYPE: DNA
<213> ORGANISM: Artificial Sequence
<220> FEATURE:
<223> OTHER INFORMATION: Synthetic

<400> SEQUENCE: 38
ctagagtaga tctgtcttaa ggtggatccg taagcttgtg aattcgtgag ct        52

<210> SEQ ID NO 39
<211> LENGTH: 44
<212> TYPE: DNA
<213> ORGANISM: Artificial Sequence
<220> FEATURE:
<223> OTHER INFORMATION: Synthetic

<400> SEQUENCE: 39
cacgaattca caagcttacg gatccacctt aagacagatc tact                44

<210> SEQ ID NO 40
<211> LENGTH: 48
<212> TYPE: DNA
<213> ORGANISM: Photinus pyralis

<400> SEQUENCE: 40
atcggatcct ttttatggaa gacgccaaaa acataaagaa aggcccgg            48

<210> SEQ ID NO 41
<211> LENGTH: 32
<212> TYPE: DNA
<213> ORGANISM: Photinus pyralis

<400> SEQUENCE: 41
gatgataagc ttacacggcg atctttccgc cc                             32

<210> SEQ ID NO 42
<211> LENGTH: 26
<212> TYPE: DNA
<213> ORGANISM: Plasmodium falciparum

<400> SEQUENCE: 42
caatggcccc tttcttaagc attttg                                    26

<210> SEQ ID NO 43
<211> LENGTH: 28
<212> TYPE: DNA
<213> ORGANISM: Plasmodium falciparum

<400> SEQUENCE: 43
gcatggatcc tgatatattt ctattagg                                  28

<210> SEQ ID NO 44
<211> LENGTH: 64
<212> TYPE: DNA
<213> ORGANISM: Plasmodium berghei

<400> SEQUENCE: 44
atcccccggg ggtaccctgc aggtcgactt aattaaggat atggcagctt aatgttcgtt    60
tttc                                                                64

<210> SEQ ID NO 45

```
<211> LENGTH: 30
<212> TYPE: DNA
<213> ORGANISM: Plasmodium berghei

<400> SEQUENCE: 45
tactactagc ggccgcctac cctgaagaag                                              30

<210> SEQ ID NO 46
<211> LENGTH: 27
<212> TYPE: DNA
<213> ORGANISM: Artificial Sequence
<220> FEATURE:
<223> OTHER INFORMATION: Synthetic

<400> SEQUENCE: 46
atcctcgaga tggtgacagg gggaatg                                                 27

<210> SEQ ID NO 47
<211> LENGTH: 25
<212> TYPE: DNA
<213> ORGANISM: Artificial Sequence
<220> FEATURE:
<223> OTHER INFORMATION: Synthetic

<400> SEQUENCE: 47
ggatcccggg ttaaacacag tagta                                                   25

<210> SEQ ID NO 48
<211> LENGTH: 34
<212> TYPE: DNA
<213> ORGANISM: Plasmodium falciparum

<400> SEQUENCE: 48
gaagttccta tactttctag agaataggaa cttc                                         34

<210> SEQ ID NO 49
<211> LENGTH: 34
<212> TYPE: DNA
<213> ORGANISM: Plasmodium falciparum

<400> SEQUENCE: 49
gaagttccta ttctctagaa agtataggaa cttc                                         34

<210> SEQ ID NO 50
<211> LENGTH: 34
<212> TYPE: DNA
<213> ORGANISM: Plasmodium falciparum

<400> SEQUENCE: 50
ataacttcgt atagcataca ttatacgaag ttat                                         34

<210> SEQ ID NO 51
<211> LENGTH: 34
<212> TYPE: DNA
<213> ORGANISM: Plasmodium falciparum

<400> SEQUENCE: 51
ataacttcgt ataatgtatg ctatacgaag ttat                                         34

<210> SEQ ID NO 52
<211> LENGTH: 74
<212> TYPE: DNA
<213> ORGANISM: Plasmodium falciparum

<400> SEQUENCE: 52
```

```
atatccgcgg gaagttccta ttctctagaa agtataggaa cttcctgaaa catattttgt    60
acatatcatt ttac                                                      74

<210> SEQ ID NO 53
<211> LENGTH: 33
<212> TYPE: DNA
<213> ORGANISM: Plasmodium falciparum

<400> SEQUENCE: 53
atatactagt ctagatcttc ttgtctgttt tcg                                 33

<210> SEQ ID NO 54
<211> LENGTH: 31
<212> TYPE: DNA
<213> ORGANISM: Plasmodium falciparum

<400> SEQUENCE: 54
atatccatgg cagctataga acttccatca g                                   31

<210> SEQ ID NO 55
<211> LENGTH: 72
<212> TYPE: DNA
<213> ORGANISM: Plasmodium falciparum

<400> SEQUENCE: 55
atatggcgcc gaagttccta actttctag agaataggaa cttcgataat cttctgatg      60 attttttctat tc                                                       72

<210> SEQ ID NO 56
<211> LENGTH: 66
<212> TYPE: DNA
<213> ORGANISM: Plasmodium falciparum

<400> SEQUENCE: 56
atatccgcgg gaagttccta ttctctagaa agtataggaa cttcggatct ctataaatgc    60
atgagg                                                               66

<210> SEQ ID NO 57
<211> LENGTH: 28
<212> TYPE: DNA
<213> ORGANISM: Plasmodium falciparum

<400> SEQUENCE: 57
atatactagt ctgggtgagt ttttgccg                                       28

<210> SEQ ID NO 58
<211> LENGTH: 34
<212> TYPE: DNA
<213> ORGANISM: Plasmodium falciparum

<400> SEQUENCE: 58
atatcctagg caaggaaaaa aattaagggt tgtg                                34

<210> SEQ ID NO 59
<211> LENGTH: 72
<212> TYPE: DNA
<213> ORGANISM: Plasmodium falciparum

<400> SEQUENCE: 59
atatggcgcc gaagttccta actttctag agaataggaa cttcgttcat ttatatattt     60
ggaaatatca tc                                                        72
```

```
<210> SEQ ID NO 60
<211> LENGTH: 66
<212> TYPE: DNA
<213> ORGANISM: Plasmodium falciparum

<400> SEQUENCE: 60
atatccgcgg gaagttccta ttctctagaa agtataggaa cttcggagag tatagcaaaa      60
tgttgc                                                                66

<210> SEQ ID NO 61
<211> LENGTH: 34
<212> TYPE: DNA
<213> ORGANISM: Plasmodium falciparum

<400> SEQUENCE: 61
atatactagt gtgcatgttt cattagcata atcc                                 34

<210> SEQ ID NO 62
<211> LENGTH: 33
<212> TYPE: DNA
<213> ORGANISM: Plasmodium falciparum

<400> SEQUENCE: 62
atatcctagg gggaatttac atgccattct atg                                  33

<210> SEQ ID NO 63
<211> LENGTH: 63
<212> TYPE: DNA
<213> ORGANISM: Plasmodium falciparum

<400> SEQUENCE: 63
atatggcgcc gaagttccta tactttctag agaataggaa cttccctata cccttccctt     60
gtg                                                                   63

<210> SEQ ID NO 64
<211> LENGTH: 30
<212> TYPE: DNA
<213> ORGANISM: Plasmodium falciparum

<400> SEQUENCE: 64
ccagaaaatt gcccttctag agcctttgtt                                      30

<210> SEQ ID NO 65
<211> LENGTH: 27
<212> TYPE: DNA
<213> ORGANISM: Plasmodium falciparum

<400> SEQUENCE: 65
gcccaataca tcatttgaat aagcatg                                         27

<210> SEQ ID NO 66
<211> LENGTH: 30
<212> TYPE: DNA
<213> ORGANISM: Plasmodium falciparum

<400> SEQUENCE: 66
tgtttacact cgaatgtggg atggcatcct                                      30

<210> SEQ ID NO 67
<211> LENGTH: 30
<212> TYPE: DNA
<213> ORGANISM: Plasmodium falciparum
```

```
<400> SEQUENCE: 67
gaatggcatg taaattccca cattatatct                                    30

<210> SEQ ID NO 68
<211> LENGTH: 19
<212> TYPE: DNA
<213> ORGANISM: Plasmodium falciparum

<400> SEQUENCE: 68
aatcttgaac gaggatgcc                                                19

<210> SEQ ID NO 69
<211> LENGTH: 23
<212> TYPE: DNA
<213> ORGANISM: Plasmodium falciparum

<400> SEQUENCE: 69
ggaaaccttg ttacgacttc tcc                                           23

<210> SEQ ID NO 70
<211> LENGTH: 19
<212> TYPE: DNA
<213> ORGANISM: Homo sapiens

<400> SEQUENCE: 70
gaaggtgaag gtcggagtc                                                19

<210> SEQ ID NO 71
<211> LENGTH: 20
<212> TYPE: DNA
<213> ORGANISM: Homo sapiens

<400> SEQUENCE: 71
gaagatggtg atgggatttc                                               20

<210> SEQ ID NO 72
<211> LENGTH: 32
<212> TYPE: DNA
<213> ORGANISM: Plasmodium falciparum

<400> SEQUENCE: 72
atatccgcgg ggatctctat aaatgcatga gg                                 32

<210> SEQ ID NO 73
<211> LENGTH: 82
<212> TYPE: DNA
<213> ORGANISM: Plasmodium falciparum

<400> SEQUENCE: 73
atatactagt ataacttcgt atagcataca ttatacgaag ttatctgggt gagttttgc    60 cgtagtacta aaagcatcat tc                                            82

<210> SEQ ID NO 74
<211> LENGTH: 83
<212> TYPE: DNA
<213> ORGANISM: Plasmodium falciparum

<400> SEQUENCE: 74
atatcctagg ataacttcgt ataatgtatg ctatacgaag ttatgggaat ttacatgcca   60
ttctatgtaa aggaagatat aac                                           83

<210> SEQ ID NO 75
```

```
<211> LENGTH: 29
<212> TYPE: DNA
<213> ORGANISM: Plasmodium falciparum

<400> SEQUENCE: 75
atatggcgcc ctatacccct tcccttgtg                                          29

<210> SEQ ID NO 76
<211> LENGTH: 31
<212> TYPE: DNA
<213> ORGANISM: Plasmodium falciparum

<400> SEQUENCE: 76
atcccgcggt gtagattaaa agaatctgtt g                                       31

<210> SEQ ID NO 77
<211> LENGTH: 32
<212> TYPE: DNA
<213> ORGANISM: Plasmodium falciparum

<400> SEQUENCE: 77
gatactagtc cttaaaatgg ctattaatac cc                                      32

<210> SEQ ID NO 78
<211> LENGTH: 32
<212> TYPE: DNA
<213> ORGANISM: Plasmodium falciparum

<400> SEQUENCE: 78
atcgaattcg cagttggaat atggaaaact ag                                      32

<210> SEQ ID NO 79
<211> LENGTH: 30
<212> TYPE: DNA
<213> ORGANISM: Plasmodium falciparum

<400> SEQUENCE: 79
gatcctaggt gcataccgtt ccaaattgac                                         30

<210> SEQ ID NO 80
<211> LENGTH: 31
<212> TYPE: DNA
<213> ORGANISM: Plasmodium falciparum

<400> SEQUENCE: 80
atcccgcggc tctttttttt atttcatttt a                                       31

<210> SEQ ID NO 81
<211> LENGTH: 68
<212> TYPE: DNA
<213> ORGANISM: Plasmodium falciparum

<400> SEQUENCE: 81
cggactagtg aagttcctat actttctaga gaataggaac ttcttagcta tcaatgaata        60
ataaatta                                                                 68

<210> SEQ ID NO 82
<211> LENGTH: 86
<212> TYPE: DNA
<213> ORGANISM: Plasmodium falciparum

<400> SEQUENCE: 82
atcgaattcg aagttcctat tctctagaaa gtataggaac ttcaagatgg tgctatagca        60
```

```
agtactagtg aattttatat agaacc                                          86
```

<210> SEQ ID NO 83
<211> LENGTH: 29
<212> TYPE: DNA
<213> ORGANISM: Plasmodium falciparum

<400> SEQUENCE: 83

```
gatcctagga tagatgtatt gttccctcc                                       29
```

<210> SEQ ID NO 84
<211> LENGTH: 33
<212> TYPE: DNA
<213> ORGANISM: Plasmodium falciparum

<400> SEQUENCE: 84

```
atcccgcggc catttatcat aaaattgtgg tcc                                  33
```

<210> SEQ ID NO 85
<211> LENGTH: 84
<212> TYPE: DNA
<213> ORGANISM: Plasmodium falciparum

<400> SEQUENCE: 85

```
gatactagtg aagttcctat actttctaga gaataggaac ttcttagtcg atatccttca     60
acgctctctt atcatcattt gcag                                            84
```

<210> SEQ ID NO 86
<211> LENGTH: 80
<212> TYPE: DNA
<213> ORGANISM: Plasmodium falciparum

<400> SEQUENCE: 86

```
atcgaattcg aagttcctat tctctagaaa gtataggaac ttcggatccg actctgagga     60
attagatagt tctaaagagg                                                 80
```

<210> SEQ ID NO 87
<211> LENGTH: 30
<212> TYPE: DNA
<213> ORGANISM: Plasmodium falciparum

<400> SEQUENCE: 87

```
gatcctaggt aacaagcaca ttacgtacag                                      30
```

<210> SEQ ID NO 88
<211> LENGTH: 88
<212> TYPE: DNA
<213> ORGANISM: Plasmodium falciparum

<400> SEQUENCE: 88

```
gatactagtg aagttcctat actttctaga gaataggaac ttcttactta aaatggctat     60
taatacccat accaaatata gctattcc                                        88
```

<210> SEQ ID NO 89
<211> LENGTH: 83
<212> TYPE: DNA
<213> ORGANISM: Plasmodium falciparum

<400> SEQUENCE: 89

```
atcgaattcg aagttcctat tctctagaaa gtataggaac ttcgcagttg gaatatggaa     60
aactagaaaa aattacaaaa acg                                             83
```

```
<210> SEQ ID NO 90
<211> LENGTH: 88
<212> TYPE: DNA
<213> ORGANISM: Plasmodium falciparum

<400> SEQUENCE: 90
gatactagta taacttcgta tagcatacat tatacgaagt tatttactta aaatggctat      60
taatacccat accaaatata gctattcc                                        88

<210> SEQ ID NO 91
<211> LENGTH: 83
<212> TYPE: DNA
<213> ORGANISM: Plasmodium falciparum

<400> SEQUENCE: 91
atcgaattca taacttcgta taatgtatgc tatacgaagt tatgcagttg gaatatggaa      60
aactagaaaa aattacaaaa acg                                             83

<210> SEQ ID NO 92
<211> LENGTH: 33
<212> TYPE: DNA
<213> ORGANISM: Plasmodium falciparum

<400> SEQUENCE: 92
atcccgcggg agtttattca tgtggacatg tgc                                  33

<210> SEQ ID NO 93
<211> LENGTH: 66
<212> TYPE: DNA
<213> ORGANISM: Plasmodium falciparum

<400> SEQUENCE: 93
atcactagta taacttcgta tagcatacat tatacgaagt tatgttcatt ctgaagaacg      60
ttatgg                                                                66

<210> SEQ ID NO 94
<211> LENGTH: 64
<212> TYPE: DNA
<213> ORGANISM: Plasmodium falciparum

<400> SEQUENCE: 94
atcgaattca taacttcgta taatgtatgc tatacgaagt tattgacgct tcttttgata      60
ctgc                                                                  64

<210> SEQ ID NO 95
<211> LENGTH: 29
<212> TYPE: DNA
<213> ORGANISM: Plasmodium falciparum

<400> SEQUENCE: 95
actcctagga tccacatata ttgtctgcc                                       29

<210> SEQ ID NO 96
<211> LENGTH: 35
<212> TYPE: DNA
<213> ORGANISM: Plasmodium falciparum

<400> SEQUENCE: 96
atcccgcggg tggttatata tacacataac ttagc                                35

<210> SEQ ID NO 97
```

```
<211> LENGTH: 67
<212> TYPE: DNA
<213> ORGANISM: Plasmodium falciparum

<400> SEQUENCE: 97
atcactagta aacttcgta tagcatacat tatacgaagt tatcaatgga agaactttgt    60
aaacaag                                                             67

<210> SEQ ID NO 98
<211> LENGTH: 65
<212> TYPE: DNA
<213> ORGANISM: Plasmodium falciparum

<400> SEQUENCE: 98
atcgaattca taacttcgta taatgtatgc tatacgaagt tatcaagtat agtagggtta   60
acagg                                                               65

<210> SEQ ID NO 99
<211> LENGTH: 31
<212> TYPE: DNA
<213> ORGANISM: Plasmodium falciparum

<400> SEQUENCE: 99
atccctaagc ttcttctggt gttcccattc g                                  31
```

LIVE GENETICALLY ATTENUATED MALARIA VACCINE

CROSS-REFERENCES TO RELATED APPLICATIONS

This application is a continuation-in-part application of U.S. application Ser. No. 10/583,186, filed May 15, 2007, which is the National Stage of International Application No. PCT/US04/43023, filed Dec. 20, 2004, which claims the benefit of U.S. Provisional Application No. 60/631,228, filed Nov. 26, 2004, and U.S. Provisional Application No. 60/531,479, filed Dec. 19, 2003, all three of which are incorporated by reference in their entireties.

STATEMENT OF GOVERNMENT LICENSE RIGHTS

This invention was made with government support under R01AI053709 awarded by the National Institutes of Health. The government has certain rights in the invention.

SEQUENCE LISTING

A sequence listing in electronic form is submitted herewith, and the material in the sequence listing is hereby incorporated-by-reference into this application.

FIELD OF THE INVENTION

This invention relates to live genetically modified *Plasmodium* organisms and their use as immunospecific immunoeffectors for vaccination purposes.

BACKGROUND OF THE INVENTION

Malaria has a tremendous impact on human health, killing millions annually and the disease is a major impediment for social and economic development of nations in malaria-endemic areas, particularly in sub-Saharan Africa (1, see the appended Citations). Malaria is a mosquito-borne disease that is transmitted by inoculation of the *Plasmodium* parasite sporozoite stage. Sporozoites invade hepatocytes (2), transform into liver stages, and subsequent liver stage development ultimately results in release of pathogenic merozoites (3).

Because an effective "subunit" malaria vaccine has remained elusive and the complexity of the malaria parasite *Plasmodium* might preclude the successful development of such a vaccine, whole organism vaccine approaches against malaria have lately found renewed interest (4). The feasibility of such a vaccine has been demonstrated in animal models and subsequently in humans by induction of sterile protective immunity through inoculation with irradiation-attenuated parasites (5, 6). Liver stages (LS) are a prime malaria vaccine target because they can be completely eliminated by sterilizing immune responses, thereby preventing malaria infection (7). The recent availability of complete *Plasmodium* genome sequences (8, 9) may now permit the development of live-attenuated parasites by more precise and defined genetic manipulations.

Using expression profiling, we previously identified genes that are specifically expressed during the pre-erythrocytic part of the parasite life cycle (11, 12). A number of pre-erythrocytic genes named UIS (up-regulated in infective sporozoites) also showed up-regulation in sporozoites when they gain infectivity for the mammalian host (11).

SUMMARY OF THE INVENTION

Here we show by reverse genetics that selected individual genes, exemplified by UIS3 (up-regulated in infective sporozoites gene 3) and UIS4, are essential for early liver stage development: uis3(−) and uis4(−) sporozoites infect hepatocytes but are no longer able to establish blood stage infections in vivo and thus do not lead to disease. The invention thereby provides the first live *Plasmodium* organisms that are genetically engineered to disrupt liver-stage-specific gene functions.

Surprisingly, immunization with either uis3(−) or uis4(−) sporozoites confers complete protection against infectious sporozoite challenge in a rodent malaria model. This protection is sustained and stage-specific. These findings provide the first genetically attenuated whole organism malaria vaccines. Similar results with uis3(−) or uis4(−) sporozoites have been obtained in another rodent malaria model and using sporozoites in which other liver-stage-specific gene functions were disrupted, as shown, for example, in EXAMPLE 4 with disruption of S22 in *P. yoelii* and in EXAMPLE 5 with simultaneous disruption of p52 and p36 in *P. yoelii*. Moreover, p52(−) and p36(−) deficient *P. falciparum* lines also exhibit developmental arrest in the liver, confirming the potential of these mutant parasite lines as a vaccine against malaria in humans, as described in EXAMPLE 11.

An LS-specific gene function may be identified using routine methodology that is standard in the art. For example, an LS-specific gene function may be identified by assessing the function of genes whose expression is up-regulated in liver-stage parasites ("LS-up-regulated genes"). For example, genes whose expression is up-regulated in liver-stage parasites may be expressed at higher levels in liver-stage parasites than, e.g., in the sporozoite population that emerges from mosquito mid-gut oocysts. Up-regulation of expression of such genes may also be observed in mature, infective salivary gland sporozoites (as for the UIS4 and UIS3 genes discussed in EXAMPLES 1 and 2, below).

Thus, the invention provides a method for inoculating a vertebrate host against malaria, by administering to the host a live *Plasmodium* organism that is genetically engineered to disrupt a liver-stage-specific gene function. The invention further provides a vaccine composition comprising a live *Plasmodium* organism that is genetically engineered to disrupt a liver-stage-specific gene function. In addition, the invention provides the use of a vaccine composition comprising a live *Plasmodium* organism that is genetically engineered to disrupt a liver-stage-specific gene function. The invention also provides for production of a vaccine composition, by suspending and packaging the subject engineered *Plasmodium* organisms in a suitable pharmaceutically acceptable carrier solution.

BRIEF DESCRIPTION OF THE DRAWINGS

The foregoing aspects and many of the attendant advantages of this invention will become more readily appreciated as the same become better understood by reference to the following detailed description, when taken in conjunction with the accompanying drawings, wherein.

Amino acid identities of the *P. yoelii* and *P. falciparum* UIS3 orthologs (EAA22537 and PF13_0012, respectively) are indicated as percentage of identical residues compared with the *P. berghei* sequence.

Figure 2:
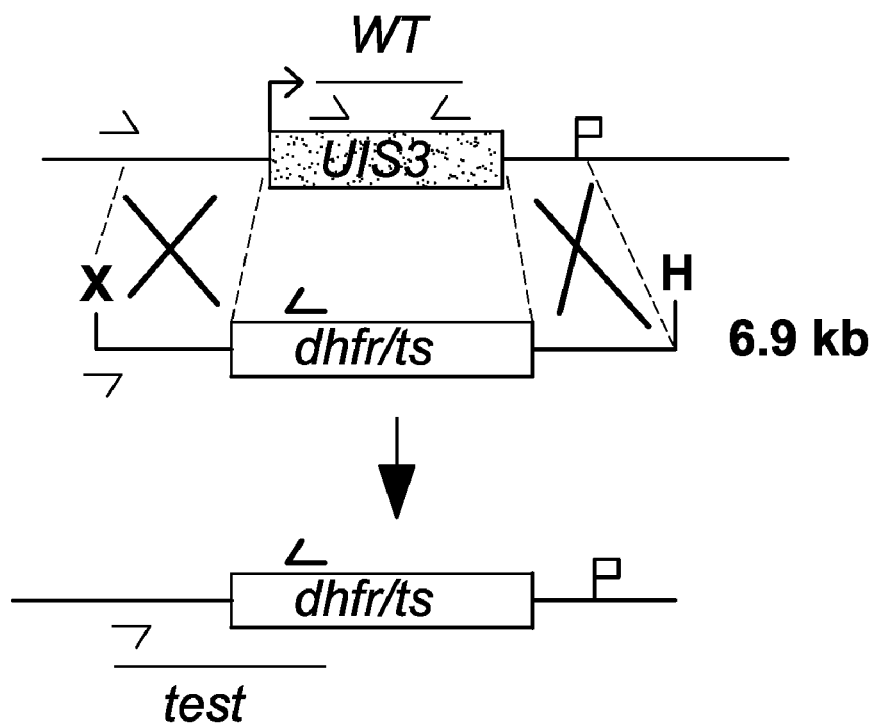

FIG. 2 depicts the replacement strategy used to generate the uis3(−) parasite described in EXAMPLE 1. The wild-type (WT) UIS3 genome locus is targeted with an EcoRI/HindIII-linearized replacement plasmid containing the 5' and 3' untranslated regions of the UIS3 open reading frame (ORF) and the *Toxoplasma gondii* dhfr/ts− positive selectable marker. Upon a double crossover event the UIS3 ORF is replaced by the selection marker. Replacement-specific test primer combinations are indicated by arrows, and expected fragments are shown as lines. A similar strategy was used for to generate the loss-of-function parasites described in EXAMPLES 2, 4, 5, 9-11, 13, and 14.

Figure 3:
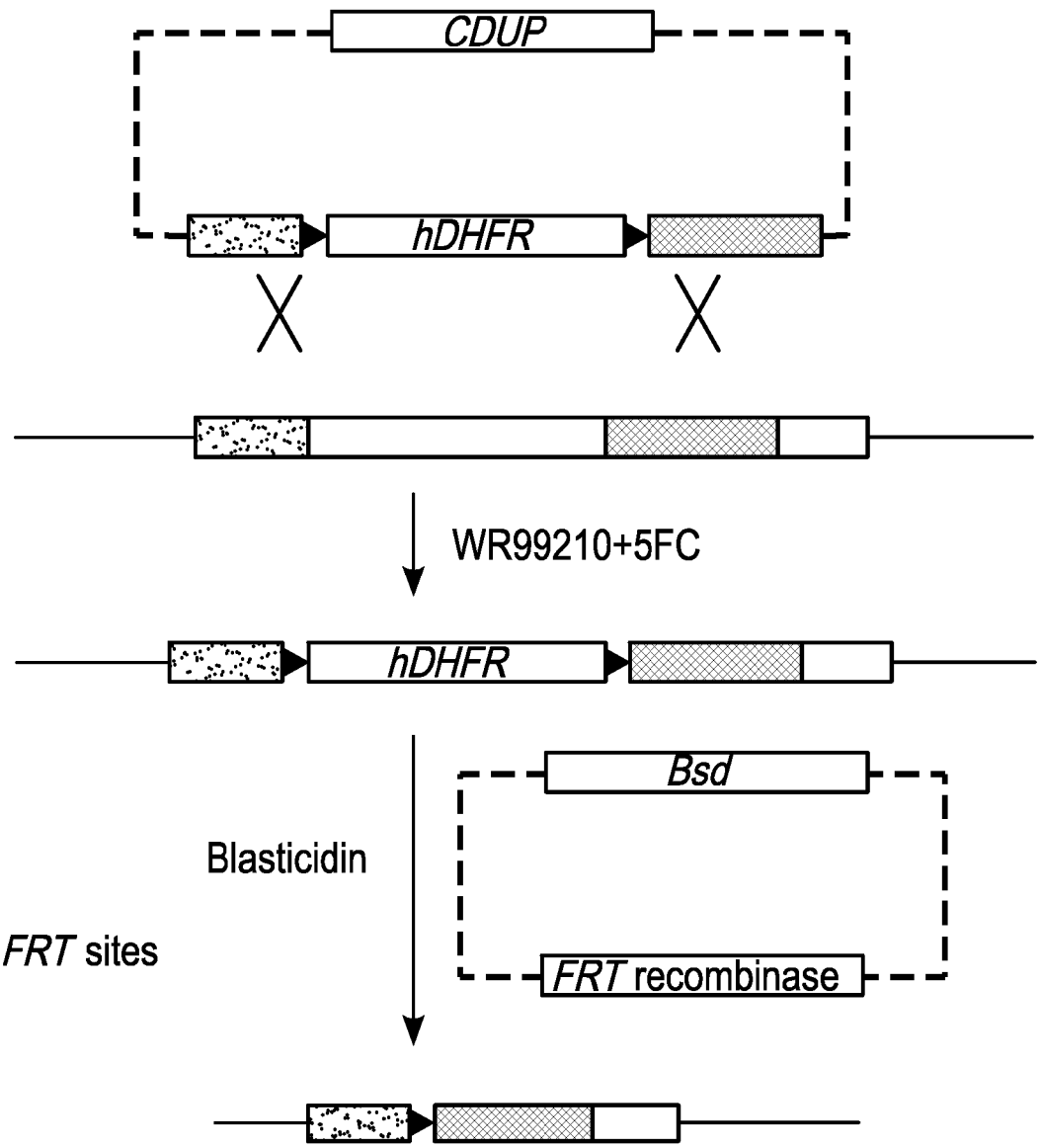

FIG. 3 depicts the strategy for generating loss-of-function parasites using double crossover recombination and FLP recombinase to remove the positive selectable marker, as described in EXAMPLE 7. The vectors are derivatives of pCC1 containing FRT sequences to catalyze recombination for deletion of the positive selectable marker. pCC1-derivatives contain the cytosine deaminase/uracil phosphoribosyl transferase gene (CDUP) to select parasites in which the construct integrated by homologous double crossover recombination. The positive selectable marker of pCC1 is hDHFR. A second vector (pCC4-FLP) containing the positive selectable marker bsd and flp recombinase is introduced to the parasites to catalyze deletion of the positive selectable marker (e.g. hDHFR).

Figure 4:
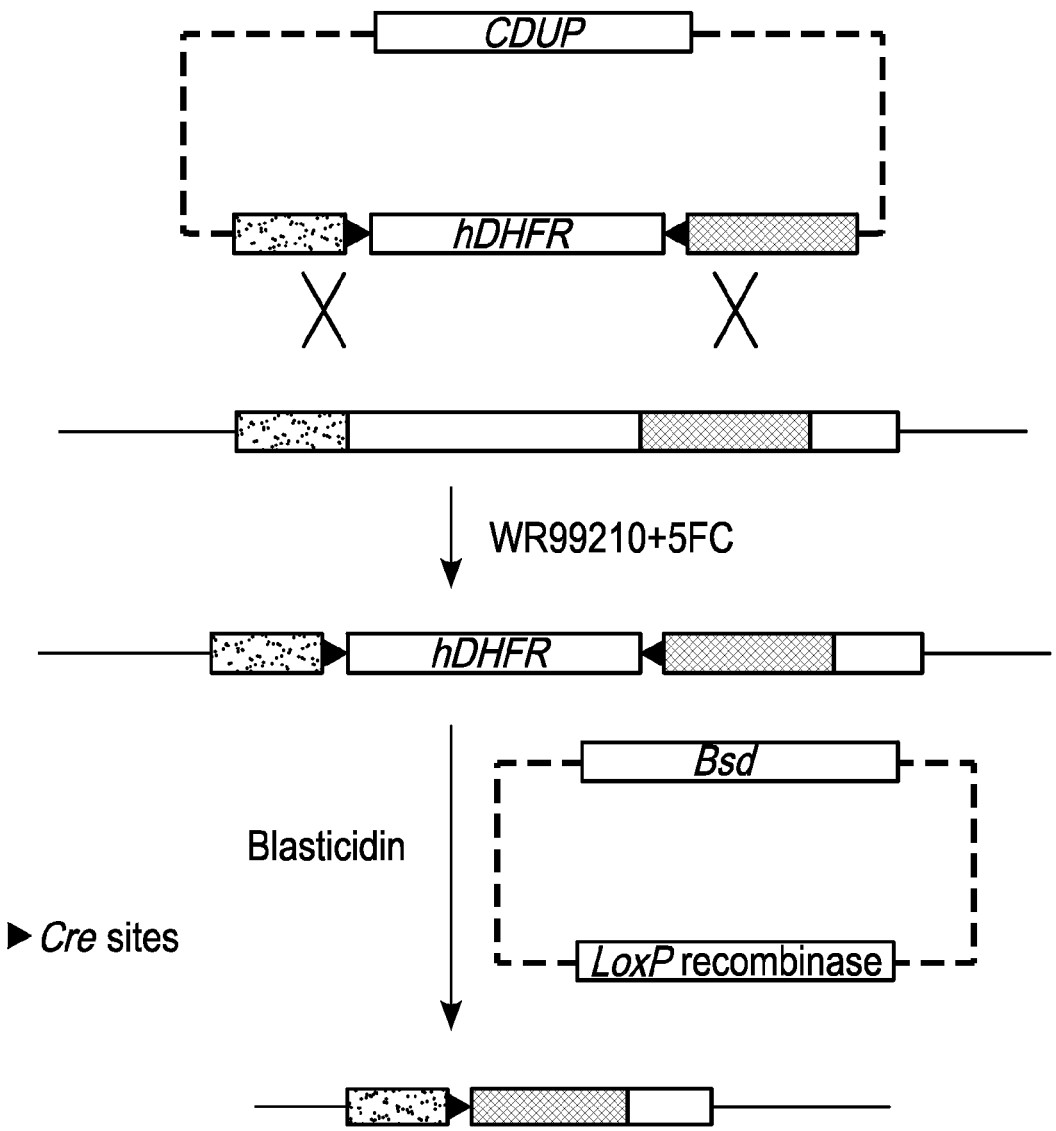

FIG. 4 depicts the strategy for generating loss-of-function parasites using double crossover recombination and Cre recombinase to remove the positive selectable marker, as described in EXAMPLE 8. The vectors are derivatives of pCC1 containing loxP sequences to catalyse recombination for deletion of the positive selectable marker. pCC1-derivatives contain CDUP to select parasites in which the construct integrates by homologous double crossover recombination. The positive selectable marker of pCC1 is hDHFR. A second vector (pCC4-Cre) containing the positive selectable marker bsd and Cre recombinase is introduced to the parasites to catalyze deletion of the positive selectable marker (e.g. hDHFR), as described in EXAMPLE 12.

Figure 5:
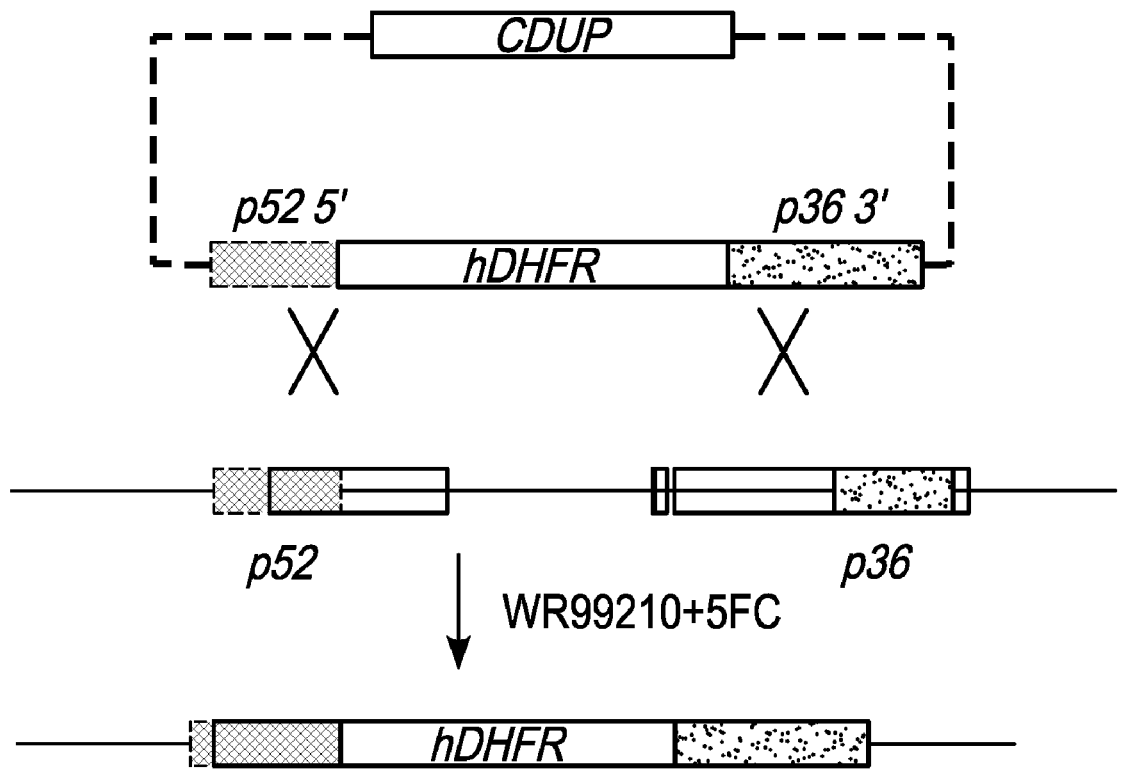

FIG. 5 depicts the strategy for disrupting both p52 and p36 using double crossover recombination, as described in EXAMPLE 11. The vector used was a derivative of pCC1. The pCC1 vector contains two cassettes the first containing the hDHFR gene for positive selection, driven by the calmodulin promoter (5' CAM) and has the histidine rich protein 2 terminator (3' hrp2). The second cassette has the CDUP gene for negative selection with 5-FC and is driven by the heat shock protein 86 promoter (5' hsp86) and flanked by the *Plasmodium berghei* dhfr terminator (3' PbDT). The plasmid backbone contains the cassette for bacterial expression and selection (AMP). The homologous flanks of p52 and p36 for recombination are marked (p52 5' flank, and p36 3' flank) and shown as crosshatched and stippled regions, respectively.

DETAILED DESCRIPTION OF THE PREFERRED EMBODIMENT

The invention provides a method for inoculating a vertebrate host against a *Plasmodium* parasite, by administering to the host a live *Plasmodium* organism that is genetically engineered to disrupt a liver-stage-specific gene function.

By "*Plasmodium* parasite" or "*Plasmodium* organism" is meant any member of the protozoan genus *Plasmodium*, including the four species that cause human malaria: *P. vivax, P. malariae, P. falciparum,* and *P. ovale*. The corresponding vertebrate host is a human or other secondary host that is susceptible to infection by the wild-type *Plasmodium* parasite.

For use as a live anti-malarial vaccine, the *Plasmodium* parasite is genetically engineered to disrupt a liver-stage-specific gene function. The term "disrupt liver-stage-specific gene function" or "disrupt LS-specific gene function" means interfering with an LS-specific gene function such as to completely or partially inhibit, inactivate, attenuate, or block the LS-specific gene function, for example, by gene disruption or influencing transcription, translation, protein folding, and/or protein activity. The term "liver-stage-specific gene function" or "LS-specific gene function" refers to a function that is required in liver stage parasites to ultimately produce infectious merozoites and establish the erythrocytic stage of the life cycle, but that is not required for productive entry into host hepatocytes or, preferably, maintenance of the parasite in asexual blood cell stages and production of infective sporozoites in mosquitoes. Exemplary *P. falciparum* genes with LS-specific gene functions include, but are not limited to, UIS3 (PF13_0012), UIS4 (PF10_0164), LSA-1 (PF10_0356), SAP1 (S22) (PF11_0480), p52 (PFD0215c), p36 (PFD0210c), Etramp "Y" (MAL8P1.6), Etramp "Z" (PF14_0729), FabI (PFF0730c), FabG (PFI1125c), FabB/F (PFF127c), FabZ (PF13_0128), PDH E1 alpha (PF11_0256), PDH E1 beta (PF14_0441), and PDH E2 (PF10_0407). The sequences of these genes, protein sequences encoded by them, and annotation information may be obtained from the *Plasmodium* Genome Database (http://plasmodb.org/; Kissinger et. al (2002) *Nature* 419:490-492) under the identification number provided above, and are herein incorporated by reference. In some embodiments, the LS-specific gene whose function is disrupted in the genetically attenuated *P. falciparum* parasites of the invention is one of UIS3, UIS4, LSA-1, SAP1 (S22), p52, p36, Etramp "Y", Etramp "Z", FabI, and FabG, as described in EXAMPLES 1-5 and 9-14. In some embodiments, more than one LS-specific gene function is disrupted, such as, for example, p52 and p36, as described in EXAMPLE 11.

Malaria infection is initiated by *Plasmodium* sporozoites in the salivary glands of mosquitoes. These sporozoites invade hepatocytes of the vertebrate host and differentiate into liver stage (LS) forms. After a few days the LS parasites produce several thousand merozoites that are released from the hepatocytes and invade erythrocytes to start the blood stage cycle that causes malaria disease. According to the invention, the *Plasmodium* parasite is genetically engineered to disrupt at least one LS-specific gene function such that the genetically engineered parasites remain capable of invading hepatocytes but cannot produce merozoites that can establish blood stage infections. Of course, pursuant to this disclosure, more than one LS-specific gene function can be disrupted (such as by creating, for example, double knock-outs as described in EXAMPLE 11) as such redundancy may ensure an additional degree of protection against parasitemia.

Pursuant to this disclosure, an LS-specific gene function may be identified using routine methodology that is standard in the art. For example, an LS-specific gene function may be identified by assessing the function of genes whose expression is up-regulated in liver-stage parasites ("LS-up-regulated genes"). For example, genes whose expression is up-regulated in liver-stage parasites may be expressed at higher levels in liver-stage parasites than, e.g., in the sporozoite population that emerges from mosquito mid-gut oocysts. Up-regulation of expression of such genes may also be observed in mature, infective salivary gland sporozoites (like in the UIS4 and UIS3 genes discussed in the Examples below). Well-known methods for differential transcriptional profiling, including, but not limited to, subtractive hybridization screens, differential display, and genome-wide microarray analyses, may be used for identifying genes whose expression is up-regulated in liver-stage parasites. Such methods have been previously used to analyze infectivity-associated changes in the transcriptional repertoire of sporozoite-stage parasites (11) and to identify *Plasmodium* genes that encode pre-erythrocytic stage-specific proteins (12). For example, suppression subtractive hybridization permits selective enrichment of differentially regulated cDNAs of high and low abundance through a combination of hybridization and polymerase chain reaction (PCR) amplification protocols that allow the simultaneous normalization and subtraction of the cDNA populations. Suppression subtractive hybridization has been used to analyze transcriptional differences between non-infective and infective sporozoites and to identity genes controlling infectivity to the mammalian host (11). This procedure has permitted the identification of LS-up-regulated genes, including, but not limited to, the UIS3 and UIS4 genes disrupted in the Examples below. Suppression subtractive hybridization of *Plasmodium* salivary gland sporozoites versus merozoites has also been used to identify stage-specific pre-erythrocytic transcripts (12). Differential expression of candidate LS-specific genes may be confirmed using methods that are standard in the art, including dot blots, reverse transcriptase PCR(RT-PCR), immunoblotting, immunofluorescence microscopy, and/or microarray expression analyses, as previously described (11, 12).

In some embodiments of the invention, LS-specific gene functions are identified by analyzing the function of LS-up-regulated genes, as further described below. However, not all genes with an LS-specific gene function are necessarily LS-up-regulated genes. Thus, genes whose expression is not up-regulated in LS forms may nevertheless possess an LS-specific gene function.

Interference with a liver-specific function may also be achieved by LS-specific overexpression of an inhibitory factor. This factor may be inserted by reverse genetics methods into a pseudogene, i.e., one that is not essential for parasite survival at any time point during the life cycle (47). The inhibitory factor should not confer toxicity to the parasite but rather act in arresting LS development. Such a factor may include, but is not limited to, inhibitors of cell-cycle progression and/or ubiquitin-mediated proteolysis, and/or factors that interfere with post-transcriptional control of gene-expression.

LS-specific gene functions may be identified by analyzing the phenotype of parasites in which one or more gene functions have been disrupted. Several methods for disrupting gene functions in *Plasmodium* are well-known in the art and may be used in the practice of the invention. Such methods include, but are not limited to, gene replacement by homologous recombination, antisense technologies, and RNA interference. For example, methods of gene targeting for inactivation or modification of a *Plasmodium* gene by homologous recombination have been established (13). Such methods were herein successfully used to disrupt LS-specific gene functions, as described in EXAMPLES 1, 2, 4, 5, 9-11, and 13.

Antisense technology has also been successfully used for disrupting *Plasmodium* gene functions. For example, exogenous delivery of phosphorothioate antisense oligonucleotides against different regions of the *P. falciparum* topoisomerase II gene resulted in sequence-specific inhibition of parasite growth (14). Similarly, transfection of an antisense construct to the *Plasmodium falciparum* clag9 gene, which had been shown to be essential for cytoadherence by targeted gene disruption, resulted in a 15-fold reduction in cytoadherence compared to untransfected control parasites (15).

Another exemplary technology that may be used in the practice of the invention to disrupt LS-specific gene functions is RNA interference (RNAi) using short interfering RNA molecules (siRNA) to produce phenotypic mutations in genes. RNAi has been used as a method to investigate and/or validate gene function in various organisms, including plants, *Drosophila*, mosquitoes, mice, and *Plasmodium* (see, e.g., 37-44). In *Plasmodium*, RNAi has been used, for example, to demonstrate the essential role of a PPI serine/threonine protein phosphatase (PfPP1) from *P. falciparum* (41). RNAi has also been used to inhibit *P. falciparum* growth by decreasing the level of expression of the gene encoding dihydroorotate dehydrogenase (42) and by blocking the expression of cysteine protease genes (43). In the mouse malaria model, RNAi has been used to inhibit gene expression in circulating *P. berghei* parasites in vivo (44). These studies have demonstrated the use of RNAi as an effective tool for disrupting gene function in *Plasmodium* organisms.

The gene disruption approaches described above (for example, gene targeting by homologous recombination, antisense, and RNAi) have been used successfully to investigate the function of virtually all genes in an organism's genome. For example, the availability of sequenced genomes has enabled the generation of siRNA libraries for use in large-scale RNAi studies to screen for genes that are involved in various processes, such as developmental pathways or stages (see, e.g., 45 and 46). Such screens may be used in the practice of the invention to identify LS-specific gene functions in *Plasmodium*. Assays that may be used for identifying LS-specific gene functions include, but are not limited to, phenotypic analyses such as the phenotypic assays described in EXAMPLES 1, 2, 4, 5, and 11. The term "phenotypic analysis" includes all assays with vital recombinant parasites that are generated in a wild type, fluorescent or any other transgenic reporter background. Assays may be performed in vivo, with cultured cells, in in vitro development assays or any other system that provides a read-out for LS development.

Positive selectable markers introduced during the process of genetically disrupting genes in *Plasmodium* may be removed following disruption using standard methods in the art, for example, by using a site-specific recombination system such as Flp/FRT (90) or Cre/lox (91). Alternatively, the positive selectable markers may be only transiently expressed to select for genetically disrupted parasites using tetracycline analogue-regulated transgene expression, as previously described (92). In some embodiments, blood stage-specific promoters may be used to drive expression of the selectable marker, which would silence expression of the selectable marker in the mosquito and liver stages. Methods for removing positive selectable markers following disruption are further described in FIGS. 3 and 4, and EXAMPLES 7, 8, and 12.

The engineered *Plasmodium* organisms in which an LS-specific gene function has been disrupted are typically grown in cell culture or animals, expanded in the mosquito host, and harvested as sporozoites for use in vaccines (see, e.g., 16). Methods for producing attenuated, aseptic mosquitoes suitable for administration as a vaccine, as well as methods for cryopreservation of sporozoites have been previously described (e.g., 93-96, U.S. Pat. No. 7,229,627, herein incorporated by reference). The subject vaccine compositions are produced by suspending the attenuated live *Plasmodium* organisms in a pharmaceutically acceptable carrier. Suitable pharmaceutically acceptable carriers include sterile water or sterile physiological salt solution, particularly phosphate buffered saline (PBS), as well known in the art.

Vaccines according to the invention can be administered, e.g., intradermally, subcutaneously, transcutaneously, epidermally, through mucous membranes, into submucosal tissue, intramuscularly, intraperitoneally, and intravenously. Suitable methods of administering the live attenuated sporozoites of the invention are described in PCT/US03/37498, filed Nov. 20, 2003, and U.S. Patent Application Publication No. US 2005/0220822, published on Oct. 6, 2005, both of which are herein incorporated by reference. A single inoculation or a series of two or more inoculations may be used to achieve the desired level of protection. Thus, a first priming dose of the vaccine may be followed by subsequent booster doses. The number of inoculations may range between 1 and 6 doses within a year, with additional booster doses in subsequent years.

Dosage is empirically selected to achieve the desired immune response in the host. By "immune response" is meant an acquired and enhanced degree of protective immunity, preferably complete or sterile protection, against subsequent exposure to wild-type *Plasmodium* sporozoites. For example, in EXAMPLES 1, and 3-5 below, sterile protection was achieved following three vaccinations with 10,000 live genetically attenuated sporozoites per inoculation. In some embodiments, the protective immunity achieved after administration of the genetically attenuated sporozoites of the invention will not be complete but will reduce the severity of the disease symptoms after exposure to wild-type *Plasmodium* parasites (partial protection).

A suitable dose of genetically attenuated *Plasmodium* sporozoites, such as *P. falciparum* genetically attenuated sporozoites, per inoculation may be between about 1,000 to about 10 million sporozoites, such as between about 1,000 and 1 million sporozoites, or between 5,000 and 50,000 sporozoites, or between 10,000 and 50,000 sporozoites. In some embodiments of the invention, a dose of at least about 1,000 genetically attenuated sporozoites are administered to a human subject per inoculation. In some embodiments of the invention, a dose of at between about 1,000 and 10,000 genetically attenuated sporozoites are administered to a human subject. In some embodiments of the invention, a dose of at between about 10,000 and 100,000 genetically attenuated sporozoites are administered to a human subject.

Some embodiments of the invention provide methods for inoculating a human subject to confer protective immunity against subsequent exposure to *Plasmodium* parasites (such as *P. vivax, P. malariae, P. falciparum,* or *P. ovale* parasites), comprising administering to a human subject live *Plasmodium* sporozoites (such as *P. vivax, P. malariae, P. falciparum,* or *P. ovale* sporozoites), wherein the live *Plasmodium* sporozoites are genetically engineered to disrupt a liver-stage-specific gene function. Some embodiments of the invention provide methods for inoculating a human subject to confer protective immunity against subsequent exposure to *Plasmodium* parasites (such as *P. vivax, P. malariae, P. falciparum,* or *P. ovale* parasites), comprising administering to a human subject live *Plasmodium* sporozoites (such as *P. vivax, P. malariae, P. falciparum,* or *P. ovale* sporozoites), wherein the live *Plasmodium* sporozoites are genetically engineered to disrupt a gene that is upregulated in liver stage parasites or in infective salivary gland sporozoites and whose function is not required for entry into host hepatocytes.

It is generally contemplated that inoculating a subject according to the methods of the invention with genetically attenuated *Plasmodium* sporozoites of one *Plasmodium* species will induce protective immunity against challenge with wildtype *Plasmodium* parasites of the same species. However, it has been shown that immunization with sporozoites of one *Plasmodium* species can protect against challenge with another *Plasmodium* (113-115), and eliciting cross-species protection in this manner is also within the scope of the invention.

In some embodiments, the methods of the invention confer protective immunity sufficient to prevent malaria in at least 60% of human subjects, such as, for example at least 60%, at least 70%, at least 80%, at least 90%, at least 95%, or at least 99% of human subjects, following exposure to wildtype *Plasmodium falciparum* (complete protective immunity). In some embodiments, the methods of the invention confer protective immunity sufficient to reduce the symptoms of malaria in at least 60% of human subjects, such as, for example at least 60%, at least 70%, at least 80%, at least 90%, at least 95%, or at least 99% of human subjects, following exposure to wild-type *Plasmodium falciparum* (partial protective immunity). Previous experiments with the rodent models *P. yoelii* and *P. berghei* demonstrated that genetically attenuated sporozoites provide sterile protection for as long as 8 months against challenge with 10,000 wild-type sporozoites (unpublished). Later time points have not yet been tested. Therefore, sterile protection might extend beyond 8 months. In some embodiments, 70-100% of human subjects are completely protected against challenge with wildtype *Plasmodium* parasites (such as *P. falciparum* parasites) 2 weeks after the last immunizing dose of genetically attenuated sporozoites, and 50-100% of human subjects remain completely protected against challenge 6 months after the first challenge. In some embodiments, 70-100% of human subjects, such as 95% of human subjects, are completely protected against challenge with wildtype *Plasmodium* parasites (such as *P. falciparum* parasites) for at least 10 months, similar to the complete protection previously observed with radiation-attenuated sporozoites (6). In some embodiments, 70-100% of human subjects, such as 95% of human subjects, are completely protected against challenge with wildtype *Plasmodium* parasites (such as *P. falciparum* parasites) for longer than 10 months. In some embodiments, 70-100% of human subjects are partially protected against challenge with wildtype *Plasmodium* parasites (such as *P. falciparum* parasites) 2 weeks after the last immunizing dose of genetically attenuated sporozoites, and 50-100% of human subjects remain partially protected against challenge 6 months after the first challenge. In some embodiments, 70-100% of human subjects, such as 95% of human subjects, are partially protected against challenge with wildtype *Plasmodium* parasites (such as *P. falciparum* parasites) for at least 10 months. In some embodiments, 70-100% of human subjects, such as 95% of human subjects, are partially protected against challenge with wildtype *Plasmodium* parasites (such as *P. falciparum* parasites) for longer than 10 months.

DETAILED TECHNICAL DESCRIPTION

Background. Radiation-attenuated sporozoites are a singular model that achieves sterile, protective immunity against malaria infection.

Malaria causes more than 300 million clinical cases and more than 1 million deaths annually. The disease has a severe negative impact on the social and economic progress of developing nations. Transmission of the malaria parasite *Plasmodium* to the mammalian host occurs when infected mosquitoes bloodfeed and inoculate the sporozoite stage (spz). After entering the bloodstream, spzs are quickly transported to the liver where they extravasate and invade hepatocytes (2). Within hepatocytes, spzs transform into liver stages (LS) (also called exo-erythrocytic forms, EEFs). LS parasites grow, undergo multiple rounds of nuclear division and finally produce thousands of merozoites (17, 18). Merozoites released from the liver rapidly invade red blood cells and initiate the erythrocytic cycle, which causes malaria disease. A protective malaria vaccine would have tremendous impact on global health but despite over a century of efforts, no vaccine has been developed that confers prolonged protection. Yet, we have known for more than 35 years that sterile protracted protection against malaria infection is possible.

Immunization of mice with radiation-attenuated rodent model malaria spzs (gamma-spzs) induces sterile immunity against subsequent infectious spz challenge, thus completely preventing the initiation of blood stage infection from the liver (5). Importantly, based on these findings it was later shown that immunization of humans with gamma-*P. falciparum* spzs completely protected greater than 93% of human recipients (13 of 14) against infectious spz challenge and that protection can last for at least 10 months (6). Gamma-spzs retain the capacity to infect the liver of the mammalian host and invade hepatocytes (19-20). However, LS derived from gamma-spzs suffer arrested development and thus do not produce red blood cell-infectious merozoites. Although, the inoculated stage is the spz, the main immune target is the infected hepatocyte harboring the LS (21). Protective immunity is spz-dose and radiation-dose dependent: greater than 1000 immunizing bites from *P. falciparum*-infected mosquitoes exposed to 15,000-20,000 rads of gamma radiation is required to protect the majority of subjects exposed to infectious spz challenge (6). Mosquitoes inoculate between 10-100 spzs during a bite (22-23). Therefore, the total spz dose for complete protection comes to 10,000-100,000. Importantly, immunization with over-irradiated spzs or heat-inactivated spzs fails to induce protection, indicating that the spz must remain viable for some time after inoculation and must progress to a liver stage that induces protection (6, 24). On the basis of observations in the rodent malaria model, protracted protective immunity may depend on sufficient expression of LS antigen (Ag), because treatment with primaquine, a drug that kills LS, aborts the development of protection (21). Importantly, protection induced by *P. falciparum* gamma-spzs is strain-transcending: inoculation with gamma-spzs of one parasite strain confers protection against heterologous strains (6).

Although we have learned much about spz gene expression in the last few years (25-27), the LS as the putative immunological target(s) of gamma-spzs induced protection have so far completely eluded gene expression analysis because of their inherent experimental inaccessibility. We currently know only one liver stage-specific Ag, liver stage antigen-1 (LSA-1) (28). Thus, the fine Ag specificity of lymphocytes participating in protective immunity remains unknown in humans, because the Ags expressed by LS parasites remain unknown.

Feasibility to create genetically attenuated *Plasmodium* Liver Stages. To generate genetically attenuated *Plasmodium* LS that are defective only in LS development a stage-specific gene that plays an essential and exclusive role at this stage needs to be disrupted. The gene should not be essential during the blood stage cycle given that *Plasmodium* is haploid and transfection is done with asexual blood stages and the mutant parasites are typically maintained as blood stages (13). We previously employed transcription-profiling based on the prediction that infectious *Plasmodium* spzs residing in the mosquito salivary glands are uniquely equipped with transcripts required for hepatocyte invasion and subsequent development of the LS (11). Next, we screened for transcripts that are specific for pre-erythrocytic and absent from blood cell stages in order to generate a subset of genes that can disrupted (12). The combined screens identified two abundant salivary-gland-spz-enriched transcripts that are absent from blood stages, termed UIS3 and UIS4 (for upregulated in infectious spzs). Cell biological studies have shown that both encoded proteins locate to the parasitophorous vacuole, the parasite-derived organelle where replication and schizogony takes place (data not shown).

Gene knockouts using insertion and replacement strategies have now revealed that both genes are necessary for LS development (see EXAMPLES 1 and 2 below). Both proteins are normally expressed in spzs (data not shown), but uis3(−) and uis4(−) parasites develop normal spzs and these invade hepatocyte normally. However, uis3(−) and uis4(−) LS arrest in intermediate-LS development and do not produce late LS (data not shown). Therefore, both UIS3 and UIS4 have LS-specific gene functions. Remarkably, animals infected by natural bite or intravenously with doses of up to 10,000 spzs do not become patent, confirming that both genes play vital roles in successful completion of the *Plasmodium* life cycle (see Tables 1 and 2 below). Therefore, we succeeded in generating the first genetically attenuated LS.

The results obtained with uis3(−) and uis4(−) *P. berghei* parasites described in EXAMPLES 1 and 2 have now been extended and confirmed in another murine *Plasmodium* species, *P. yoelii* (71, herein incorporated by reference). One dose of *P. yoelii* uis4(−) spz or two doses of uis3(−) spz conferred complete protection after subsequent challenge with wildtype spz (71). Moreover, we have successfully generated additional genetically attenuated *P. yoelii*, and *P. falciparum* parasites that lack one or more other LS-specific gene functions, as described in EXAMPLES 4, 5, 9-11, and 13.

Based on these discoveries we and others can now advance and test various LS-up-regulated genes identified by microarray analysis for their importance in LS development. We predict that more LS-up-regulated genes will turn out to be essential for LS development (i.e., to possess LS-specific gene functions), especially uniquely expressed genes given the remarkable capacity of the parasite to develop from a single spz to more than 10,000 daughter merozoites. Such LS-up-regulated genes can be similarly disrupted to produce additional live vaccine candidates, as described herein.

Representative embodiments of the present invention are described in the following examples.

EXAMPLE 1

This first Example was published by Nature AOP on Dec. 5, 2004 (29).

Figure 1:
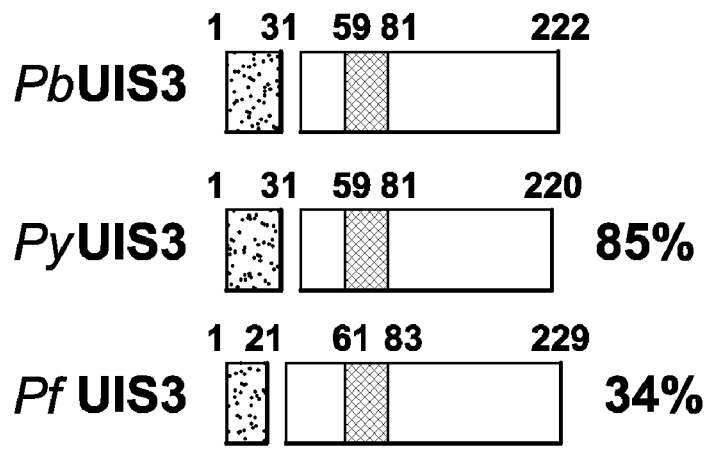
FIG. 1 depicts the primary structure of *Plasmodium* UIS3 proteins, as discussed in EXAMPLES 1 and 3. Predicted cleavable signal peptides and transmembrane spans are indicated with stippled and cross-hatched boxes, respectively.

We hypothesized that inactivation of UIS genes for which expression is restricted to pre-erythrocytic stages could lead to attenuation of the liver stage parasite, without affecting the blood stages or mosquito stages. We focused on a gene called UIS3 that encodes a small conserved transmembrane protein (FIG. 1). UIS3 was expressed in infectious sporozoites (12) and we determined that it was also expressed after sporozoite infection of livers in vivo (data not shown). UIS3 of rodent malaria parasites (accession number EAA22537) and UIS3 of the human malaria parasite *P. falciparum* (Pf13_0012) show 34% amino acid sequence identity (FIG. 1). Because the rodent malaria parasites such as *P. berghei* (Pb) are excellent models to study *Plasmodium* liver stage and pre-erythrocytic immunity we pursued investigation of UIS3 in this species.

The endogenous PbUIS3 gene was deleted using an established replacement strategy (13) (FIG. 2). After transfection, parental blood stage parasites were used to obtain clonal parasite lines designated uis3(−) that contained exclusively the predicted locus deletion (data not shown). As expected, uis3(−) parasites showed normal asexual blood stage growth and normal transmission to the *Anopheles* mosquito vector (data not shown). Within the mosquito uis3(−) sporozoites developed normally in midgut oocycts and infected the salivary glands in numbers comparable to wildtype (WT) sporozoites (data not shown). Reverse transcriptase (RT)-PCR confirmed lack of UIS3 expression in uis3(−) sporozoites (data not shown). uis3(−) sporozoites showed typical gliding motility, a form of substrate-dependant locomotion that is critical for sporozoite transmission and infectivity (30) (data not shown). They also retained their host cell invasion capacity of cultured hepatoma cells at levels comparable to WT parasites (data not shown).

Intracellular uis3(−) sporozoites initiated the typical cellular transformation process that leads to de-differentiation of the banana-shaped elongated sporozoite to a spherical liver trophozoite (17, 31) (data not shown). In marked contrast, uis3(−) parasites showed a severe defect in their ability to complete transformation into liver trophozoites (data not shown). Only a small fraction of uis3(−) parasites developed into spherical early liver stages that in addition appeared consistently smaller than the corresponding WT forms. Consequently, mutant parasites lacked the capacity to progress to mature liver schizonts (data not shown). Based on this extreme developmental defect observed in vitro, we next tested if uis3(−) sporozoites had lost their capacity to progress through liver stage development and lead to blood stage infections in vivo. Indeed, intravenous injection of up to 100,000 uis3(−) sporozoites failed to induce blood stage parasitemia in young Sprague/Dawley rats which are highly susceptible to *P. berghei* sporozoite infections (data not shown). Control WT sporozoites induced blood stage parasitemia in rats between 3-4 days after injection.

Thus, the observed phenotypic characteristics of uis3(−) parasites, i.e., their ability to invade hepatocytes and their defect in complete liver stage development allowed us to test them as a whole organism vaccine in a mouse/sporozoite challenge model. We intravenously immunized mice with uis3(−) sporozoites using different prime-boost regimens and subsequently challenged the mice by intravenous injection of infectious WT sporozoites (Table 1). Protection was evaluated by blood smear to detect the development of blood stage parasitemia starting two days after sporozoite challenge, the most stringent readout for sterile protection against malaria infection. Priming with 50,000 uis3(−) sporozoites followed by 2 boosts with 25,000 uis3(−) sporozoites completely protected all immunized mice against a challenge with 10,000 WT sporozoites given 7 days after the last boost (Table 1). Complete sterile protection against the same sporozoite challenge dose was also achieved with a similar prime-2 boost protocol using 10,000 uis3(−) sporozoites (Table 1). We next immunized mice using the same prime-boost protocols but challenged with WT sporozoites 4 weeks after the last boost. None of the challenged mice developed blood stage infections and thus enjoyed protracted sterile protection (Table 1). Protracted protection was confirmed by a re-challenge experiment where protected animals were challenged again with a high inoculum of 50,000 infectious sporozoites after two months. All animals remained completely protected. Mice immunized with uis3(−) sporozoites were also completely protected against re-challenge by infectious mosquito bite (Table 1). To determine the level of protection with a reduced immunization dose we tested a prime-single boost protocol with 10,000 uis3(−) sporozoites. Seven out of ten animals enjoyed complete protection, while the remaining three animals became patent after a long delay in patency. Next, a subset of immunized mice was challenged by direct inoculation with blood stage parasites. All animals developed blood stage parasitemia two days after challenge, indicating that the observed protective immunity is not acting against blood stages and thus was specific against pre-erythrocytic stages. Finally, to evaluate a more vaccine-relevant delivery route we immunized mice subcutaneously using a prime-2 boost protocol with 50,000 uis3(−) and 25,000 uis3(−) sporozoites, respectively. All mice were completely protected against subsequent intravenous WT sporozoite challenge.

Our results show that it is possible to develop genetically modified malaria parasites that are completely attenuated at the liver stage, which normally establishes infection of the mammalian host after mosquito transmission. This attenuation was achieved by deletion of a single parasite gene, UIS3. Although UIS3 function remains unknown, uis3(−) parasites clearly lacked the ability to compensate for its loss. The protracted sterile protection against malaria that we observed after immunization with uis3(−) sporozoites in the mouse/sporozoite challenge model provides proof of principle that a genetically modified malaria vaccine is feasible. We identified a UIS3 orthologue (accession number PF13_0012) in the genome of the most lethal human malaria parasite *P. falciparum*. This will allow us to create a genetically attenuated uis3(−) human parasite that can be tested as a vaccine in human/sporozoite challenge models. Together our findings lead the way to the development of a genetically attenuated, protective whole organism malaria vaccine that prevents natural infection by mosquito bite.

Methods: *Plasmodium berghei* transfection. For replacement of PbUIS3 two fragments were amplified using primers: UIS3rep1for (5' GGGTACCCGCATTAGCATAACATCT-CATTGG 3') (SEQ ID NO: 1) and UIS3rep2rev (5' CAAGCTTGCTTTCATATATTTGTTATTTGTC 3') (SEQ ID NO: 2) for the 800 by 3' fragment; and: UIS3rep3for (5' GGAATTCCCATATGTTTGTGTAACATC 3') (SEQ ID NO: 3) and UIS3rep4rev (5' CTCTAGAGTGTGCTTAAAT-GTTTCTTTAAAC 3') (SEQ ID NO: 4) for the 760 bp 5' fragment using *P. berghei* genomic DNA as template. Cloning into the *P. berghei* targeting vector (13) resulted in plasmid pAKM19. To obtain clonal parasite populations, limited dilution series and i.v. injection of one parasite into 15 recipient NMRI mice each was performed. For RT-PCR analysis we dissected $6 \times 10^5$ uis3(−) and $6 \times 10^5$ WT salivary gland sporozoites and isolated polyA$^+$ RNA using oligo dT-columns (Invitrogen). For cDNA-synthesis and amplification we performed a two step-PCR using random decamer primers (Ambion) and subsequent standard PCR reactions.

Phenotypical analysis of uis3(−) parasites. *Anopheles stephensi* mosquito rearing and maintenance were under a 14 h light/10 h dark cycle, 75% humidity and at 28° C. or 20° C., respectively. For each experiment, mosquitoes were allowed to blood-feed for 15 min. on anaesthetized NMRI-mice that had been infected with wild-type *P. berghei* NK65 or the uis3(−) clone and were assayed for a high proportion of differentiated gametocytes and microgametocyte-stage parasites capable of exflagellation. Mosquitoes were dissected at days 10, 14, and 17 to determine infectivity, midgut sporozoite and salivary gland sporozoite numbers, respectively. For analysis of sporozoite motility, sporozoites were deposited onto precoated (3% BSA/RPMI 1640) glass coverslips, fixed for 10 min at RT with 4% paraformaldehyde, and incubated using primary antibody against P. berghei circumsporozoite protein (anti-PbCSP) (32). To detect liver stages in hepatocytes, $10^3$ Huh7 cells were seeded in eight chamber slides and grown to semiconfluency. P. berghei sporozoites were added, incubated 90 min. at 37° C., and washed off. After 8, 12, 15, 24, 36 and 48 h, LS were revealed using primary antibodies against the P. berghei heat shock protein 70 (HSP70) (33). To analyze sporozoite invasion a double staining protocol with anti-CSP antibody was used (36). To determine the infectivity of clonal sporozoite populations in vivo young Sprague-Dawley rats were injected intravenously with 100 microliter sporozoite suspension in RPMI 1640. Parasitemia of the animals was checked daily by Giemsa-stained blood smears. The appearance of a single erythrocytic stage represents the first day of patency.

Immunization and parasite challenge experiments. For all experiments female C57BL/6 mice (Charles River Laboratories) at the age of 50 to 80 days were used. For immunization, uis3(−) sporozoites were extracted from salivary glands from infected mosquitoes. Typically, a single infected mosquito contained 20,000 uis3(−) sporozoites. Sporozoites were injected in a volume of 100 microliters intravenously into the tail vein or subcutanously into the neck of animals. Animals were immunized with a single dose of 1 or $5 \times 10^4$ uis3(−) sporozoites, followed by two boosts of either 1 or $2.5 \times 10^4$ uis3(−) sporozoites administered i.v. or s.c. The first boost was given 14 days following the immunization, with a second boost following 7 days thereafter, or at time intervals indicated. One set of animals was immunized followed by a single boost with $1 \times 10^4$ uis3(−) sporozoites each. The animals were then monitored for the parasitemia by daily blood smears. All animals remained blood stage parasite-negative after the first immunization and subsequent boosts. Animals were challenged 7 days up to 1 month after receiving the last boost of uis3(−) sporozoites by intravenous or subcutaneous injection of either $5 \times 10^4$ or $1 \times 10^4$ infectious P. berghei WT sporozoites. For each set of experiments, at least three naive animals of the same age group were included to verify infectivity of the sporozoite challenge dose. In each naive animal, parasitemia was readily detectable at days three to five after injection by Giemsa-stained blood smears. Protected animals were monitored for at least 14 days and typically up to 1 month. A re-challenge study was performed for one immunization experiment two months after the first challenge with a single dose of $5 \times 10^4$ infective P. berghei WT sporozoites. To test whether uis3(−) immunized mice were protected against re-challenge by natural transmission 10 protected and 5 naive control mice were exposed for 10 min to 10 highly infected mosquitoes that contained an average of 40,000 WT salivary gland sporozoites each. Successful blood-feeding was confirmed by mosquito dissection after the challenge experiment. To confirm stage-specificity of protection, an additional experiment was performed with 10 mice that were fully protected against a challenge with infective sporozoites. All immunized mice and three naive control mice were challenged by intravenous injection of $5 \times 10^4$ P. berghei WT blood stage parasites. All mice were fully susceptible to blood stage inoculations with no differences in patency.

Results: Table 1 below shows that C57B1/6 mice immunized with P. berghei uis3(−) sporozoites are completely protected against a challenge with WT P. berghei sporozoites.

TABLE 1

| Exp | Immunization #'s uis3(−) spz | Boosts: 1st/2nd numbers (day) | Challenge dose (timepoint) | # Protected/ # Challenged (pre-patency) |
|---|---|---|---|---|
| I. | 50,000 | 25,000 (d.14)/ 25,000 (d.21) | 10,000 spz. (d.7) | 10/10 (no infection) |
|  | 10,000 | 10,000 (d.14)/ 10,000 (d.21) | 10,000 spz. (d.7) | 10/10 (no infection) |
|  | — | — | 10,000 spz. | 0/9 (d.3) |
| II. | 50,000 | 25,000 (d.34)/ 25,000 (d.45) | 10,000 spz. (d.30) | 5/5 (no infection) |
|  | 10,000 | 10,000 (d.34)/ 10,000 (d.45) | 10,000 spz. (d.30) | 5/5 (no infection) |
|  | — | — | 10,000 spz. | 0/6 (d.4.5) |
| III. | 50,000 | 50,000 (d.14)/ 10,000 (d.21) | 10 inf. mosq. (d.38) | 5/5 (no infection) |
|  | 10,000 | 10,000 (d.14)/ 10,000 (d.21) | 10 inf. mosq. (d.38) | 5/5 (no infection) |
|  | — | — | 10 inf. mosq. | 0/5 (d.3) |
| IV. | 10,000 | 10,000 (d.14)/ | 10,000 spz. (d.7) | 7/10 (d.8) |
|  | — | — | 10,000 spz. | 0/5 (d.3) |
| V. | 50,000 | 25,000 (d.14)/ 25,000 (d.21) | 10,000 blood st. (d.30) | 0/5 (d.2) |
|  | 10,000 | 10,000 (d.14)/ 10,000 (d.21) | 10,000 blood st. (d.30) | 0/5 (d.2) |
|  | — | — | 10,000 blood st. | 0/3 (d.2) |
| VI. | 50,000 s.c. | 25,000 (d.11) s.c./ 25,000 (d.18) s.c. | 10,000 spz. (d.23) | 5/5 (no infection) |
|  | 50,000 s.c. | 25,000 (d.11) s.c./ 25,000 (d.18) s.c. | 50,000 spz. (d.23) | 5/5 (no infection) |
|  | — | — | 10,000 spz. | 0/6 (d.4.5) |

Notes:
Mice were immunized with P. berghei uis3(−) sporozoites. Mice were challenged with infectious P. berghei WT sporozoites or blood stages. Mice were from the same age group (50-80 days old) and sporozoites were from the same mosquito batch. Timepoints in column 4 indicate the day of challenge after the final boost. The pre-patent period is defined as the time until the first appearance of a single erythrocytic stage in Giemsa-stained blood smears. Five mice of the Exp. I. group were re-challenged with one dose of 50,000 WT sporozoites 2 months after the first challenge and remained protected.

EXAMPLE 2

This second Example summarizes the following publication: Mueller, A.-K. et al. Plasmodium liver stage developmental arrest by depletion of a protein at the parasite-host interface, Proc. Natl. Acad. Sci. U.S.A. 102(8):3022-3027, 22 Feb. 2005, which is hereby incorporated by reference.

Here, we disrupted another Plasmodium protein with a critical function for complete liver stage development. UIS4 (upregulated in infective sporozoites gene 4) is expressed exclusively in infective sporozoites and developing liver stages. Targeted gene disruption of UIS4 in the rodent model malaria parasite Plasmodium berghei generated knockout parasites that complete the malaria life cycle until after hepatocyte invasion. UIS4 knockout parasites transform into early liver stages. However, they are severely impaired in further liver stage development and can only initiate blood stage infections when inoculated at high sporozoite doses. Immunization with UIS4 knockout sporozoites completely protects mice against subsequent infectious wildtype sporozoite challenge. After sporozoite invasion of hepatocytes, UIS4 localizes to the newly formed parasitophorous vacuole membrane that constitutes the parasite-host cell interface and extends as a tubo-vesicular network into the hepatocyte cytoplasm. Together our data demonstrate that depletion of UIS4 results in attenuated liver stage parasites. Genetically attenuated liver stages may induce immune responses, which inhibit subsequent infection of the liver with wildtype parasites.

Generation of uis4(−) parasites: Given that UIS4 is expressed in sporozoites but not in blood stages, we were able to pursue a targeted gene disruption at the blood stages to study the importance of UIS4 for the *Plasmodium* pre-erythrocytic life cycle stages. The endogenous PbUIS4 gene was disrupted using the above-described insertion and replacement strategies (13) (data not shown). The parental blood stage population from the successful transfection was used for selection of clonal parasite lines carrying the gene disruption. We obtained insertion/disruption clones designated uis4 (−) and replacement clones designated uis4REP(−) that contained exclusively the predicted mutant locus. The correct replacement event was confirmed by insertion-specific PCR (data not shown). To confirm PbUIS4 deficiency of the mutant parasites we performed RT-PCR and cDNA amplification using polyA+ RNA from salivary gland sporozoites as templates (data not shown). Moreover, Western blot analysis of uis4REP(−) sporozoites did not detect PbUIS4 (data not shown).

*Plasmodium berghei* transfection and genotypic analysis: For gene targeting of PbUIS4 a 582 by fragment was amplified using primers UIS41NTfor (5' CGGAATTCATCATAT-TACTAATTTTCGGGGG 3') (SEQ ID NO: 5) and UIS41NTrev (5' TCCCCGCGGTTATTCCATGT-TATAAACGTTATTTCC 3') (SEQ ID NO: 6) using *P. berghei* genomic DNA as template. Cloning into the *P. berghei* targeting vector (13) resulted in plasmid pAKM15. Parasite transformation and selection was performed as described previously (13). Integration-specific PCR amplification of the uis4(−) locus was achieved using the following primers: test1, *T. gondii* DHFR-TS for (5' CCCGCACG-GACGAATCCAGATGG 3') (SEQ ID NO: 7) and UIS4 test rev (5' CCCAAGCTTAGTTTGCATATACGGCTGCTTCC 3') (SEQ ID NO: 8); test 2, UIS4 test for (5' CGGAATTCTG-GATTCATTTTTTGATGCATGC 3' (SEQ ID NO: 9) and T7 (5' GTAATACGACTCACTATAGGC 3') (SEQ ID NO: 10). For replacement of PbUIS4 two fragments 1 kb and 600 by were amplified using primers UIS4rep1for (5' GAATTCTG-GATTCATTTTTTGATGCATGC 3') (SEQ ID NO: 11) and UIS4rep2rev (5' GGGGTACCTTTATTCAGACG-TAATAATTATGTGC 3') (SEQ ID NO: 12) for the 1 kb fragment and UIS4rep3for (5' AAAACTGCAGATAAT-TCATTATGAGTAGTGTAATTCAG 3') (SEQ ID NO:13) and UIS4rep4rev (5' CCCCAAGCTTAAGTTTG-CATATACGGCTGCTTCC 3') (SEQ ID NO:14) for the 600 by fragment using *P. berghei* genomic DNA as template. Cloning into the hDHFR targeting vector (34) resulted in plasmid pAKM17. To detect UIS4 expression in WT and mutant *P. berghei* parasites, 1×10⁵ salivary gland sporozoites were dissolved in 10 microliters SDS sample buffer. UIS4 was visualized on Western blots using the polyclonal UIS4 antisera (12) and horseradish peroxidase-coupled anti-rabbit IgG secondary antibody (Amersham). For RT-PCR analysis we dissected 8×10⁵ uis 4(−), 8×10⁵ uis4REP(−) and 4×10⁵ WT salivary gland sporozoites and isolated polyA+ RNA using oligo dT-columns (Invitrogen). For cDNA synthesis and amplification we performed a two step-PCR using random decamer primers (Ambion) and subsequent standard PCR reactions.

Phenotypic analysis of uis4(−) parasites: *Anopheles stephensi* mosquitoes were raised under a 14 h light/10 h dark cycle at 28° C., 75% humidity and were fed on 10% sucrose solution. Blood-feeding and mosquito dissection was as described (35). The number of sporozoites per infected mosquito was determined in a hemocytometer. To analyze sporozoite motility, sporozoites were deposited onto precoated glass coverslips and incubated using primary antibody against *P. berghei* circumsporozoite protein (anti-PbCSP) (35). Bound antibody was detected using Alexa Fluor 488-conjugated anti-mouse antibody (Molecular Probes). To detect liver stages in hepatocytes, *P. berghei* sporozoites were added to subconfluent hepatocytes, incubated 2 h at 37° C., and washed off. After 12, 24, 36 and 48 h, liver stages were revealed using primary antibodies against parasite heat shock protein 70 (HSP70) and a secondary antibody conjugated with Alexa Fluor 488 (Molecular Probes). To analyze sporozoite invasion, 3×10⁴ salivary gland sporozoites were added to subconfluent HepG2 cells and incubated for 90 min at 37° C. The ratio between intracellular and extracellular parasites was visualized using a double staining protocol with the anti-CSP antibody (36) and confocal microscopy. To determine the infectivity of clonal sporozoite populations in vivo, C57/Bl6 mice were injected intravenously or subcutaneously with 100 microliters sporozoite suspension of WT parasites or knockout parasites in RPMI 1640. Parasitemia of the animals was checked daily by examination of a Giemsa-stained blood smear. The appearance of a single erythrocytic stage represents the first day of patency.

Immunization and parasite challenge experiments: For all experiments female C57BL/6 mice (Charles River Laboratories) aged between 50 and 80 days were used. For immunizations, uis4REP(−) sporozoites were extracted from the salivary glands from infected mosquitoes. Sporozoites were injected in a volume of 100 microliters intravenously into the tail vein of the animals. Animals were immunized with a single dose of 10,000 or 50,000 uis4REP(−) sporozoites, followed by two boosts of either 10,000 or 25,000 uis4REP (−) sporozoites administered i.v. The first boost was given 14 days following the immunization, with a second boost following 14 days thereafter. The animals were then monitored for parasitemia by daily blood smears. Only those animals that remained blood stage parasite-negative after the first immunization and subsequent boosts were exposed to a challenge with WT sporozoites. Animals were challenged 10 days after receiving the last boost of uis4REP(−) sporozoites by intravenous injection. All challenges consisted of 50,000 infective *P. berghei* WT sporozoites. For both sets of experiments, 5 naive animals were included to verify infectivity of the sporozoite challenge dose. In each naive animal, parasitemia was readily detectable at day 3 after injection. Starting from day 3 after WT challenge, the uis4REP(−) sporozoite-immunized animals were examined for detectable parasitemia in Giemsa-stained blood smears. Animals did not show a detectable parasitemia within 50 days following the challenge and were considered completely protected.

Results are shown in Table 2 below. Immunization with uis4REP(−) sporozoites confers sterile protection. The fact that a large proportion of mice remained blood stage negative after inoculation with uis4REP(−) sporozoites allowed us to test if immunization with these attenuated sporozoites would protect mice against WT sporozoite challenge. Therefore, we immunized C57/bl6 mice with 3 doses of 50,000 or 10,000 uis4REP(−) sporozoites and subsequently challenged the mice, which remained blood stage negative after immunization, with 50,000 infectious WT sporozoites (Table 2). None of the immunized mice developed blood stage infections after challenge and therefore enjoyed complete, sterile protection. Naive mice that were challenged with 50,000 WT sporozoites developed blood stage infections 3 days after inoculation.

TABLE 2

C57B1/6 mice immunized with uis4REP(−) sporozoites are completely protected against a challenge with WT sporozoites.

| Immunization (uis4REP(−) spz.) | Boosts (days after immun./# of spz.) | # Protected/# Challenged (prepatency) |
|---|---|---|
| 50,000 | 1st (14/25,000), 2nd (28/25,000) | 8/8 (no infection)[1] |
| none | none | 0/5 (day 3)[2] |
| 10,000 | 1st (14/10,000), 2nd (28/10,000) | 8/8 (no infection)[1] |
| none | none | 0/5 (day 3)[2] |

Notes:
[1] Immunized mice were challenged with 50,000 WT *P. berghei* sporozoites at day 38 after immunization. Mice were from the same age group and sporozoites were from the same mosquito batch. Blood smears were evaluated up to day 50 after challenge.
[2] Naive control mice were from the same age group and challenged with 50,000 WT *P. berghei* sporozoites.

Summary: Our findings demonstrate that malaria parasites harbor genes that are necessary only for successful completion of the pre-erythrocytic mammalian infection, within hepatocytes. We have shown that deletion of two genes individually effectively creates genetically attenuated malaria parasites that infect the liver of the mammalian host but are severely impaired in their ability to further progress through the life cycle and cause malaria disease. Other genes in the *Plasmodium* genome, which are critical for liver stage development, can be identified with the materials, methods, and procedures described herein.

Finally, we have shown here that immunization with UIS3 and UIS4 knockout sporozoites confers complete, sterile protection against subsequent infectious sporozoite challenge in a mouse model. This demonstrates the successful use of genetically attenuated *Plasmodium* parasites as live experimental vaccines. Genetically attenuated human *Plasmodium* parasites may be similarly prepared as whole organism vaccines against malaria.

EXAMPLE 3

This third example describes a representative protocol for making a UIS3-like knockout in *P. falciparum*.

The *P. falciparum* UIS3 gene is targeted for disruption by replacement via a well-established double-crossover recombination strategy (13). The UIS3 locus is replaced by a fragment containing the 5' and 3' untranslated regions of the *P. falciparum* UIS3 open reading frame, each flanking the human dihydrofolate reductase (hdhfr) selectable marker. Sequence data for the *P. falciparum* UIS3 locus were obtained from the PlasmoDB database (www.plasmodb.org). The accession number for the coding sequence of *P. falciparum* UIS3 is PF13_0012 (12) and the location of the exon within chromosome 13 is 123930-124619 on the minus strand. The *P. falciparum* UIS3 rep1 fragment extends from nucleotides 124609-125594, and the rep2 fragment from 122872-123921.

PfUIS3 rep 1 and 2 fragments are amplified from *P. falciparum* 3D7 genomic DNA using Expand polymerase and the following primers: PfUIS3 rep1 forward 5'-GAG-TAATATAATGTGTAATGCATATGG-3' (SEQ ID NO:15) and reverse 5'-GAGACCTTCATTTCAAAAAGGAAG-3' (SEQ ID NO:16); PfUIS3 rep2 forward 5'-CAAAT-GAAAACTTGGAAATAATCAGACGAG-3' (SEQ ID NO:17) and reverse 5'-GTATTATGCTTAAATTG-GAAAAAAGTTTGAAG-3' (SEQ ID NO:18). The sizes of the rep1 and rep2 fragments amplified are 986 and 1051 base pairs, respectively. The PCR conditions are: one cycle of 94° C. for 3 min, followed by thirty cycles of 94° C. for 30 sec, 54.5° C. for 1 min, and 65° C. for 3 min.

The PCR products are digested and cloned into the pHTK (47) vector. Rep1 was cloned into restriction sites SacII and BglII, and rep2 into EcoRI and SfoI sites. The PfUIS3 replacement construct is sequenced to confirm correct cloning. Positive selection for transfected parasites carrying the dhfr gene is carried out with the drug WR99210. pHTK contains the gene for thymidine kinase, allowing for negative selection of parasites carrying the plasmid episomally.

A similar protocol may be used for making a knockout of any gene of interest in *P. falciparum* (for example, a UIS4-like gene, accession number NP_700638, PF10_0164), or for making a knockout of such LS-specific genes in other *Plasmodium* organisms. Genomic information, including genomic sequences, ESTs, annotations, automated predictions, SAGE tags, microarray data, mapping data, and open reading frames, for many *Plasmodium* organisms, including, for example, *P. falciparum*, *P. vivax*, *P. knowlesi*, *P. yoelii*, *P. chabaudi*, *P. reichenowi*, and *P. gallinaceum*, is readily available in public databases such as the National Center for Biotechnology Information (www.ncbi.nlm.nih.gov), the *Plasmodium* Genome Database (www.plasmodb.org), and the Sanger Institute (www.sanger.ac.uk).

EXAMPLE 4

This example describes the creation and characterization of a *P. yoelii* knockout parasite in which SAP1 (sporozoite asparagine-rich protein 1) has been deleted (Aly, A. S. I, Mikolajczak, S. A., Rivera, H. S., Camargo, N., Jacobs-Lorena, V., Labaied, M., Coppens, I., and Kappe, S. H. I., Targeted deletion of SAP1 abolishes the expression of infectivity factors necessary for successful malaria parasite liver infection, *Molecular Microbiology*, accepted for publication Apr. 22, 2008, herein incorporated by reference).

Malaria parasite sporozoites prepare for transmission to a mammalian host by upregulation of UIS genes. A number of UIS genes are critical to initiate establishment of the intra-hepatocytic niche. Factors that regulate expression of genes involved in gain of infectivity for the liver are unknown. We show that a conserved low complexity asparagine-rich parasite protein, SAP1, has an essential role in regulation of *Plasmodium* liver infection. Deletion of SAP1 in the rodent malaria parasite *P. yoelii* generated mutant parasites that invade hepatocytes normally but cannot initiate liver stage development. Strikingly, lack of SAP1 abolished expression of essential UIS genes that encode secreted or membrane associated proteins including UIS3, UIS4 and P52. SAP1 localization to the cytoplasm of sporozoites suggested a post-transcriptional mechanism of gene expression control. The findings demonstrate that SAP1 is essential for liver infection possibly by means of functioning as a master regulator controlling expression of infectivity-associated parasite effector genes.

The first step of malaria transmission is the injection of sporozoites into a mammalian host during a mosquito blood meal (48, 49). Initially, sporozoites form in mosquito midgut oocysts and subsequently invade and reside inside the salivary glands (50). In the mosquito salivary glands, sporozoites gain infectivity that is critical to support transmission and their life cycle progression in the mammalian liver (51, 52, 53). Previous work has demonstrated that when gaining infectivity sporozoites undergo extensive differential gene expression and unique gene products called UIS (Up-regulated in Infectious Sporozoites) are induced (11). UIS genes were shown to be essential for the liver infection. UIS3 and UIS4 (29, 54, 55) are proteins of the parasitophorous vacuole membrane (PVM), the principal host-parasite interface during cell infection (29, 54, 56). Deletion of UIS3 and UIS4 leads to complete arrest of early liver stage development inside the PVM. Recently it was shown that UIS3 interacts with liver fatty acid binding protein L-FABP, indicating a potential role of this protein in fatty acid uptake from the host hepatocyte (57). Simultaneous deletion of the UIS gene p52, a putative GPI-anchored protein and a non-UIS gene P36, a putative secreted protein, renders sporozoites unable to form a PVM during infection and also leads to developmental arrest at the early stage of hepatocyte infection (58). Therefore, UIS genes critically contribute to establishing the intracellular parasitic niche either by formation or modification of the host-parasite interface (reviewed in 59). However, it remains unknown what factors regulate the expression of UIS genes and, as a consequence, liver infectivity of sporozoites. As described below, we have identified a cytoplasmic low-complexity asparagine-rich protein, SAP1 (sporozoite asparagine rich protein 1) that is essential for liver infection, possibly by regulating expression of effector proteins such as P52, UIS3 and UIS4. Targeted deletion of PySAP1 generated mutant parasites that migrate through host cells, invade hepatocytes and can form a PVM but cannot initiate liver stage development and consequently completely loose mammalian infectivity in vivo. Drastically reduced transcript levels of liver infection-associated genes in SAP1-deficient sporozoites in combination with its cytoplasmic localization may indicate a posttranscriptional regulatory function of SAP1 in malaria parasite liver infection.

Materials and Methods

Experimental animals, parasites, and cell lines: 6-8 weeks old female BALB/c (for in vivo infection studies and immunizations) or Swiss Webster (SW) mice (for parasite cycle maintenance) were purchased from the Jackson laboratory (Bar Harbor, Me.) or Harlan (Indianapolis, Ind.). Animals handling was conducted according to Institutional Animal Care and Use Committee approved protocols. P. yoelii 17XNL (a non-lethal strain) WT and Pysap1(−) were cycled between SW mice and Anopheles stephensi mosquitoes. Infected mosquitoes were maintained on sugar water at 24° C. and 70% humidity. Salivary gland sporozoites were extracted from infected mosquitoes between days 13-15 post blood meal infection. First, mosquitoes were rinsed in 70% ethanol, washed and dissected in incomplete Dulbecco's Modified Eagle's Medium (DMEM) F12 medium. Collected mosquito tissues were ground gently with a tissue homogenizer, centrifuged at 800 rpm for 3 minutes to remove mosquito debris and sporozoites were counted in a hemocytometer. The human hepatoma cell line HepG2-CD81 (Silvie et al., 2006) was used for all in vitro assays and were maintained in DMEM-F12 medium supplemented with 10% fetal calf serum (FCS).

Generation of Pysap1(−) parasites: Targeted deletion of PySAP1 by double cross-over homologous recombination was achieved constructing a replacement plasmid in b3D.DT.H Db targeting vector (kindly provided by Dr. Andy Waters). P. yoelii 17XNL genomic DNA was used as a template to amplify a 1.5 kb fragment of the 5'UTR of PySAP1 using oligonucleotide primers PyS22rep1 forward (F) 5' GG GGTACCGTGCAATGTGAAAATGATAATGCTCGATAA G 3' (SEQ ID NO: 19) and PyS22rep2 reverse (R) 5' GCCC AAGCTTTTTTCTTTCTTAAATACAAAAAAATAATTTA T 3' (SEQ ID NO:20). The amplified fragment was inserted into the transfection plasmid between KpnI and HindIII restriction enzymes sites. Similarly, a 1 kb DNA fragment from 3'ORF sequence of PySAP1 was amplified using PyS22rep3F 5' GGACTAGTCCAGCTATAAACTCCG AAACATCGAATTATGT 3' (SEQ ID NO:21) and PyS22rep4R 5' TCCCCGCGGGCATCGCGTTGATG CTTTTGGGAATTATTG A 3' (SEQ ID NO:22) primers and inserted between SpeI and SacII restriction sites in the transfection vector. The resulting plasmids were digested with KpnI and SacII to release the replacement fragment used for the transfection. Transfection using the Amaxa nucleofector device (Amaxa GmbH, Germany) resistant parasites selection, and recombinant parasite cloning by limited dilution were all conducted as described elsewhere (61, 62). We obtained two independent Pysap1(−) clonal parasite populations that were phenotypically identical. Detailed analysis was performed with one representative clone. To confirm the targeted deletion and the new genetic recombination, Integration-specific genomic DNA (gDNA) PCR amplification of the Pysap1(−) locus was generated using the specific primers combinations Test1 (TgF 5' GGCTACGTCCCGCACGGAC-GAATCCAGATGG 3' (SEQ ID NO:23) and PyS22TestR 5' CACCCTTATAACCATCATTATCTACTTTTCC 3' (SEQ ID NO:24)) and Test2 (PyS22TestF 5' CTCTTTTTGGGAGT-CAAAAACGGTATGC 3' (SEQ ID NO:25) and TgR 5' CGCATTATATGAGTTCATTTTACACAATCC 3' (SEQ ID NO:26)). PySAP1 locus specific gDNA-PCR amplification was generated using the primers combination WT (PyS22orfF 5' GGTAAACCACGGCACGTTCCTATGTTT 3' (SEQ ID NO:27) and PyS22orfR 5' CTTGATTTATCAG-CATTGTTAATATGCCC 3' (SEQ ID NO:28)). The primers combination test for the WT PySAP1 locus was also used in RT-PCR to confirm the absence of the PySAP1 transcript from Pysap1(−) recombinant parasite clone.

Reverse transcription PCR(RT-PCR): Total RNA was extracted from P. yoelii and P. falciparum sporozoites and mixed blood stages using TRIzol reagent (Invitrogen) and treated with TURBO DNase (Ambion). cDNA synthesis was performed using the Super Script III Platinum 2-step qRT-PCR kit (Invitrogen).

Immuno-fluorescence assays (IFAs): We generated rabbit polyclonal antisera against a PySAPI$_{3020-3034}$ synthetic peptide (LRGRQVQQSFNHSAS (SEQ ID NO:29)). The antisera were further affinity purified against the synthetic peptide and the specific IgGs were concentrated. Pysap1(−) or PyWT sporozoites were air dried on poly-lysine treated glass slides. Sporozoites were fixed with 4% paraformaldehyde (PFA) for 10 minutes at room temperature (RT). This was followed by permeabilization with 0.2% Saponin for 15 minutes at RT or with no membrane permeabilization. After blocking in 10% FCS/PBS overnight (ON) at 4° C., primary antibodies were diluted 1:300 in 10% FCS/PBS, incubated with the sporozoites for 1 hour at 37° C. Mouse monoclonal antibodies against PyCSP and PyHSP70, and rabbit polyclonal antisera against PySAP1, PyUIS4, PyUIS3, PyMTIP, were used in staining of sporozoites. Alexa Fluor (Molecular Probes, Eugene, Oreg.) conjugated secondary antibodies were also diluted in 10% FCS/PBS and incubated with the sporozoites for 1 hour at 37° C. Conjugated anti-rabbit Alexa Fluor 488 (green) and anti-mouse Alexa Fluor 594 (red) were used to visualize the bound primary antibodies. Nuclear staining with 4',6'-diamidino-2-phenylindole (DAPI) was conducted within the last washing step with PBS and before mounting the slides with the anti-fade reagent (Fluoroguard; Bio-Rad, Hercules, Calif.). Preparations were analyzed using fluorescence confocal microscopy (Olympus 1X70 Delta Vision).

Sporozoites in vivo infections: For challenge and immunizations BALB/c mice were intravenously (iv) injected with sporozoites resuspended in incomplete DMEM-F12 medium. Blood stage patency was monitored daily by evaluation of Giemsa-stained blood smears from day 3 to day 14 post sporozoite infection.

Cell-traversal assay: Hepatoma HepG2-CD81 cells were inoculated in 8-wells chamber slides at a density of 60,000 cells/well 2 days before the assay. 20,000 sporozoites per well of PyWT or Pysap1(−), in addition to uninfected mosquitoes salivary glands extracts (mock), were resuspended in incomplete DMEM-F12 medium with 3% Bovine Albumin Serum (BSA) and 2 mg/ml of fluorescein isothiocyanate (FITC)-dextran (Invitrogen-Molecular Probes, Eugene, Oreg.). Sporozoites and mock suspensions were added to the cells, centrifuged 2 minutes at 1000 rpm and incubated for 1 hour at 37° C. Thereafter, the cells were washed thoroughly with PBS 1× and complete DMEM medium 2× to remove any extracellular dextran, and the cells were allowed to grow further for 3 hours in complete DMEM medium. Flow cytometric quantitative analysis of dextran-positive hepatomas was conducted using flow cytometer (Cytopia, Seattle, Wash.) and the flow cytometry analysis program FlowJo version 7.0.3 (TreeStar, Inc., Ashland, Oreg.) (58).

Hepatoma intracellular infection in vitro assays: We standardized a differential permeabilization hepatoma infection assay to specifically quantify intrahepatocytic parasites at different time points of infection by fluorescence microscopy. Hepatoma HepG2-CD81 cells were seeded in 8-wells chamber slides at a density of 30,000-50,000 cells/well 2 days before the assay. 50,000 sporozoites of Pysap1(−) or PyWT resuspended in incomplete DMEM-F12 medium were added per well. The sporozoites were incubated for 1 hour with the cells at 37° C. All wells were thoroughly washed with PBS 1× and with complete DMEM medium 2× to remove all non-invading and unbound sporozoites and mosquitoes debris. 1 hour post infection (pi) assays were fixed with 4% paraformaldehyde (which does not permeabilize hepatocytes) for 10 minutes at RT, followed by +/−permeabilization with ice cold methanol for 5 minutes at RT and then blocking in 10% FCS/PBS (ON) at 4° C. The cells for other post infection time points assays were further grown in complete DMEM medium until fixed, +/−permeabilized and blocked at 6 hours, 12 hours, 18 hours and 24 hours, respectively. Primary antibodies against PyCSP, PyHSP70 and PyUIS4 were diluted in 10% FCS/PBS and incubated with the cells for 1 hour at 37° C. Conjugated secondary anti-mouse Alexa Fluor 488 (green) and anti-rabbit Alexa Fluor 594 (red) were used to visualize the bound primary antibodies. Nuclear staining with DAPI was conducted within the last washing step with PBS and before mounting the slides with the antifade reagent. Preparations were analyzed using fluorescence confocal microscopy (Olympus 1X70 Delta Vision). Intracellular parasites were determined as the total number of parasites counted from each permeabilized hepatoma slide well out of the total number of parasites counted in the control unpermeabilized well.

Transmission Electron Microscopy: For thin-section transmission electron microscopy, $10^6$ PyWT and Pysap1(−) sporozoites were used to infect $10^6$ subconfluent HepG2-CD81 cells. One hour p.i., cells were fixed with 2.5% glutaraldehyde (Electron Microscopy Sciences, Hatfield, Pa.) in 0.1 M sodium cacodylate buffer (pH 7.4) for 1 h at room temperature and processed, as described previously (88), before examination with a Philips 410 electron microscope (Eindhoven, The Netherlands) under 80 kV.

Results

SAP1 is a conserved cytoplasmic protein with an asparagine-rich low complexity domain: We searched for putative cytoplasmic proteins that are highly expressed in sporozoites but not in blood stages because they might uniquely contribute to regulation of sporozoite infectivity. SAP1 was first identified as a sporozoite-expressed gene in a suppression subtractive hybridization (SSH) screen of *Plasmodium yoelii* salivary gland sporozoites versus blood stage merozoites (designated S22, sporozoite-specific gene 22) (12). PySAP1 (gene identifier PY03269, incorrectly annotated) has orthologs in all *Plasmodium* species including the human malaria parasite *P. falciparum* (gene identifier PF11_0480) (8, 9). Notably, PySAP1 encodes a large putative protein of about 370 kDa molecular mass. PySAP1 has one large exon followed by two small exons. We confirmed the nucleotide sequence of the 5' and 3' ends and elucidated the correct exon-intron organization using reverse transcriptase polymerase chain reaction (RT-PCR) analysis with salivary gland sporozoite RNA. The PySAP1 ORF nucleotide sequence (9723 nucleotides) and the predicted protein sequence (3240 amino acids) were deposited in NCBI (accession number: pending). We did not identify a signal sequence, transmembrane domain or any organelle-specific targeting motif in any of the predicted *Plasmodium* SAP1 putative protein sequences examined. *Plasmodium* SAP1 proteins are characterized by the presence of an extended internal asparagine-rich low complexity domain with an asparagine content of 27% in *P. yoelii* and 29% in *P. falciparum*, flanked by predicted more globular domains with low asparagine content. Interestingly, these amino (n)- and carboxyl (c)-terminal regions are highly conserved among *Plasmodium* species. The PySAP1 n-terminus shares 70% amino acid sequence identity with the n-terminus of the *P. falciparum* ortholog, and the PySAP1 c-terminus shares 89% amino acid sequence identity with c-terminus of PfSAP1. However, the overall amino acid sequence identity of SAP1 between *P. yoelii* and *P. falciparum* is only 26% due to the divergence of the asparagine-rich domain. Therefore, SAP1 is a putative cytoplasmic low complexity protein containing an asparagine-rich internal domain flanked by conserved non asparagine-rich domains.

Sporozoite-specific expression profile of PySAP1 and PfSAP1: RT-PCR analysis revealed that PySAP1 is transcribed in oocyst and salivary gland sporozoites (FIG. 1C). As expected from the previous SSH screen (12), no transcription were detected in unsynchronized mixed blood stages. A similar expression pattern of SAP1 was observed in *P. falciparum* oocyst and salivary gland sporozoites. No transcripts were detected in mixed blood stages. Thus, the sporozoite-specific transcript expression profile of PfSAP1 is similar to the expression profile of PySAP1.

Cytoplasmic localization of PySAP1: To determine the cellular localization of SAP1, we generated rabbit polyclonal antisera against a peptide in the c-terminus of PySAP1 and tested it in immunofluorescence assays (IFAs) using *P. yoelii* sporozoites. A specific sporozoite-internal staining that excluded the nucleus was observed. The staining pattern was distinct from circumsporozoite (CS) protein sporozoite surface staining and similar to cytoplasmic heat shock protein (HSP) 70 staining. The staining was only observed in sporozoites after permeabilization. This indicated that SAP1 localizes to the cytoplasm of sporozoites as predicted by the lack of any targeting signal in the SAP1 sequence. Pre-immune sera did not show reactivity with sporozoites.

Targeted deletion of PySAP1 and phenotype in blood and mosquito stages: Targeted gene deletion of PySAP1 was conducted by double-crossover homologous recombination to replace the majority of the coding sequence with the TgDHFR/TS selection marker cassette (63). Deletion-specific genomic PCR analysis confirmed the successful double crossover recombination event and Pysap1(−) recombinant parasite clones with pure gene deletion background. Therefore, PySAP1 was successfully deleted in the erythrocytic stages with no observed deficiency of blood stage development. In addition, the morphology of male and female gametocytes in thin blood smears and male gamete exflagellation in wet mounts were indistinguishable from *P. yoelii* wildtype (WT) parasites. Transmission of Pysap1(−) parasites to mosquitoes resulted in normal midgut infection and oocyst development. Pysap1(−) oocyst sporozoites developed as well as PyWT oocyst sporozoites. Importantly, Pysap1(−) sporozoites accumulated in the salivary glands in numbers comparable to WT indicating no apparent defect in salivary gland infection. RT-PCR analysis confirmed the absence of PySAP1 transcripts in Pysap1(−) sporozoites. IFAs with the anti-SAP1 antisera were negative, confirming that Pysap1(−) sporozoites did not express SAP1. The data also gave further support to the specificity of the anti-SAP1 antisera. Noteworthy, we conducted all experiments initially with two clones of Pysap1 (−) that were identical in their phenotypes. Thereafter, experiments were done with only one Pysap1(−) clone.

Pysap1(−) sporozoites fail to induce blood stage infection and elicit sterile protection against PyWT sporozoite challenge: We tested the infectivity of PySAP1 deficient salivary gland sporozoites to susceptible BALB/c mice (64). Initially, mosquito bite experiments with more than 50 Pysap1(−) infected mosquitoes/mouse did not result in blood stage infection in 3 BALB/c mice, tested daily by blood smears until day 14 post infection. Strikingly, intravenous (iv) injection of escalating doses of Pysap1 salivary gland sporozoites did not lead to blood stage parasitemia, tested daily by blood smears until day 14 post infection (Table 3) even with extremely high doses of more than 2 million sporozoites. This dose corresponded to a ~200,000 fold increase over the minimal infectious dose of *P. yoelii* WT sporozoites administered to BALB/c mice by iv injection (65). Hence, PySAP1 is essential for parasite pre-erythrocytic stage functions after transmission from mosquito to mammalian host.

TABLE 3

PySAP1 deficient sporozoites are completely attenuated and cause no infection to BALB/c mice via intravenous route of infection.

| No. of injected sporozoites | Pysap1 (−) | | PyWT | |
|---|---|---|---|---|
| | Infected | Pre-patent period* | Infected | Pre-patent period* |
| 20 | ND | ND | 2/2 | 4 days |
| 100 | ND | ND | 6/6 | 4 days |
| 10,000 | 0/30 | — | 8/8 | 3 days |
| 100,000 | 0/15 | — | 3/3 | 2.5 days |
| 500,000 | 0/8 | — | ND | ND |
| 1,000,000 | 0/4 | — | ND | ND |
| >2,000,000 | 0/3 | — | ND | ND |

*The period (in days) between sporozoite infection and the detection of erythrocytic stages in blood smears.
ND: Not done We next tested whether Pysap1(−) salivary gland sporozoite immunization of mice can induce sterile protection against PyWT sporozoite challenge. Four groups of BALB/c mice were immunized iv with three doses of 10,000 Pysap1(−) salivary gland sporozoites, in two week intervals (Table 4). The first immunization group (group I) was challenged by iv injection of 10,000 PyWT sporozoites at day 7 after the last immunization dose. Two of the immunization groups (group II and III) were challenged by iv injection of 10,000 PyWT sporozoites 30 and 210 days after the last immunization dose. The mice of group III were then challenged by PyWT erythrocytic stages 2 weeks after the last challenge with either $10^3$ or $10^6$ asexual blood stages injected iv or intraperitoneal (ip) into 5 mice each, respectively (data not shown). The fourth group (group IV) was challenged by infectious mosquito bite 45 and 210 days after the last immunization dose. All mice were protected when challenged with PyWT sporozoites and did not develop any blood stage infection (Table 4). However, mice challenged with blood stage parasites developed blood stage parasitemia after 2 days (data not shown). The data demonstrate that Pysap1(−) salivary gland sporozoite immunizations induce stage-specific sterile immunity against subsequent PyWT sporozoite infection but not against asexual blood stage infection.

TABLE 4

Immunization with Pysap1 (−) sporozoites confers sterile protection against wildtype sporozoite challenge.

| Group | Primary dose (Days of booster dose) | Challenge dose/ (days after last boost) | No. protected/ No. challenged* | Mean pre-patent period (days |
|---|---|---|---|---|
| I | 10,000 (14, 28) | 10,000/7 | 9/9 | — |
| II | 10,000 (14, 28) | 10,000/ (30)/(210) | 15/15/15 | −/− |
| III | 10,000 (14, 28) | 10,000/ (30)/(210) | 10/10/10 | −/− |
| IV | 10,000 (14, 28) | MB+/ (45)/(210) | 5/5 | −/− |

*Each immunization group had an age-matched naïve control group (minimum 3 mice) that all became patent at day 3 after each PyWT challenge.
+ Infection through mosquito bite (MB) by allowing at least 10 PyWT female infected mosquitoes with midgut oocyst infectivity higher than 90% to bite one mouse for at least 10 minutes.

Pysap1(−) sporozoites traverse and invade hepatocytes normally but suffer an early liver stage developmental arrest in vitro: Failure of salivary gland sporozoites to induce blood stage infection in mice can be due to distinct deficiency phenotypes (reviewed in 59). In order to identify and characterize the deficiency of Pysap1(−) sporozoites in completing pre-erythrocytic infection, we conducted in vitro assays with the hepatoma cell line HepG2-CD81 that sustains productive *P. yoelii* liver stage infection and development (60). Pysap1(−) salivary gland sporozoites displayed continuous gliding motility that was undistinguishable from PyWT, tested on glass slide by direct microscopic examination (52, 53). Thereafter, we tested the cell-traversal capacity of Pysap1(−) salivary gland sporozoites using a cell-wounding assay (66, 67, 68). Pysap1(−) sporozoites traversed hepatocytes and wounded cells at a rate comparable to PyWT sporozoites. Next, we specifically quantified intrahepatocytic parasites at 1-, 6-, 12-, 18- and 24 hours post infection in vitro by fluorescence microscopy. Interestingly, at 1 hour pi the number of Pysap1(−) intracellular parasites was similar to PyWT infections, but Pysap1(−) intracellular liver stage numbers gradually decreased in comparison to PyWT infections at 6 hours and 12 hours pi. Pysap1(−) intracellular parasites numbers then sharply decreased at 18 hours pi and at 24 hours pi there were almost no intracellular parasites, while PyWT infections showed robust numbers of intracellular parasites at 18 hours pi and at 24 hours pi time points. Most importantly, intrahepatocytic Pysap1(−) trophozoites failed to grow and develop. Parasites appeared smaller and deficient in their transformation when compared to PyWT liver stages. Surprisingly, immunostaining of the PVM-resident protein UIS4 was not detected in Pysap1(−) parasites at all time points tested, whereas in PyWT liver stages, a UIS4 positive PVM staining pattern was evident at all time points later than 1 hour pi. We conclude that Pysap1(−) sporozoites infect host hepatocytes but suffer growth-arrest early during liver stage development, explaining the lack of Pysap1(−) infectivity to mice.

Electron-microscopic (EM) analysis of intrahepatocytic Pysap1(−) sporozoites: Intracellular malaria parasites need a PVM for development (reviewed in 59). Therefore, we examined whether the observed lack of UIS4 in intracellular Pysap1(−) parasites indicated a possible deficiency in PVM formation. We performed an electron microscopic analysis of intracellular WT and Pysap1(−) parasites one hour after infection of HepG2-CD81 cells. Intracellular Pysap1(−) parasites were able to form a PVM. Out of 15 parasites evaluated by EM, 4 exhibited a PVM and 11 appeared free in the cytoplasm. The latter may represent sporozoites in the process of cell traversal. However, it is possible that Pysap1(−) sporozoites form a PVM but less efficiently than PyWT.

UIS gene transcripts are depleted in Pysap1(−) sporozoites: Despite the presence of a PVM we noted the lack of PyUIS4 in Pysap1(−) liver stages. PyUIS4 is normally expressed in sporozoite secretory organelles and the liver, and is essential for malaria parasite liver stage development (54). To test whether PyUIS4 protein, or other sporozoite-specific proteins are expressed in Pysap1(−) sporozoites at all before hepatocytes invasion, we performed IFAs to test UIS4, UIS3 and MTIP (69) expression in Pysap1(−) and PyWT salivary gland sporozoites. In PyWT sporozoites, we detected staining for all three proteins. We did not detect staining for PyUIS4, PyUIS3 in Pysap1(−) sporozoites but detected PyMTIP staining. To test whether this absence is due to a reduction in UIS4 transcript abundance, which would potentially indicate transcript degradation (70), we performed RT-PCR analysis on Pysap1(−) salivary gland sporozoite cDNA. Strikingly, we observed a severe reduction of PyUIS4 transcript abundance. Furthermore, when we assayed for transcripts of UIS3 (29) and p52 (58, 71, 72), both critical for liver stage infection, we again observed a severe reduction of abundance. In addition, transcript abundance for two uncharacterized UIS genes, UIS2 (putative secreted phosphatase) and UIS28 (putative secreted lipase) (11) was also reduced in Pysap1(−) sporozoites. Conversely, transcript abundance for genes that are involved in sporozoite functions prior to PVM formation and liver stage development was not reduced in Pysap1(−) sporozoites. These genes include CS and TRAP (51, 73), SPECT1 (74), SPECT2 (75), and S4/CELTOS (76). We conclude that lack of SAP1 in sporozoites has a selective negative impact on UIS gene expression.

Discussion

Successful hepatocyte infection and liver stage development by the malaria parasite is dependent on establishment of a PVM and establishment of a functional host-parasite interface. Some UIS gene products expressed in salivary gland sporozoites and liver stages play essential roles in these processes (29, 54, 55, 71). However, factors that allow sporozoites lying in wait in the mosquito salivary glands to initiate a coordinated switch to mammalian host infection by differential expression of UIS genes have not been identified. Our work identifies SAP1 as such a factor. SAP1 is the first cytoplasmic *Plasmodium* protein with an essential function for pre-erythrocytic stages. SAP1 has a large internal low-complexity asparagine-rich domain, which are frequently found in *Plasmodium* proteins (77). This is partially due to the high A and T nucleotide content in the *Plasmodium* genome (78, 79). The biological relevance of low complexity domains in *Plasmodium* proteins has been discussed as an evolutionary byproduct with no significant function in the biology of the malaria parasite (80). In contrast, low complexity proteins have been proposed as virulence inducing factors in some pathogenic bacterial strains (81), but not much is known about their roles in the biology of infection. The low complexity domain of SAP1 is embraced by two highly conserved non-asparagine-rich c- and n-terminal domains. The level of conservation in these domains is very high among SAP1 proteins from distinct *Plasmodium* species, indicating that they represent functionally important regions. Pysap1(−) salivary gland sporozoites showed extremely reduced transcript abundance for UIS3, UIS4 and p52 but not SPECTs, TRAP and CS, indicating a selective mechanism of UIS transcript depletion. The former are highly induced in WT salivary gland sporozoites but are not expressed in WT sporozoites emerging from the mosquito midgut oocysts. It will be of interest to determine whether transcript abundance for additional genes is affected in the Pysap1(−) sporozoites as we have shown here for the uncharacterized UIS2 and UIS28. Lack of UIS expression cannot be attributed to a defect in salivary gland invasion and residence because Pysap1(−) sporozoites infected the glands with efficiencies that were comparable to WT sporozoites. Therefore, it appears likely that the reduction of UIS transcript expression in Pysap1(−) sporozoites is a direct effect of the lack of SAP1 and not an indirect effect of an altered biological behavior of the mutant.

Transcript abundance in eukaryotes is mainly regulated by transcriptional and posttranscriptional mechanisms. SAP1 localization to the sporozoite cytoplasm and absence of SAP1 from the sporozoite nucleus indicates that SAP1 is involved in a yet to be defined posttranscriptional mechanism of UIS transcript regulation, since posttranscriptional regulation is expected to be executed in the cytoplasm of the cell (70, 82). Interestingly, posttranscriptional regulation has been discussed as a main pathway for controlling the expression levels of proteins in *Plasmodium* (83, 84). Indeed, it has been suggested that *Plasmodium* must rely on this mechanism for controlling the extensive differential gene expression, required by the complexity of the malaria parasite life cycle (85). Recently, it has been shown that a RNA helicase termed DOZI (Development of Zygote Inhibited) is expressed in the female gametocyte where it localizes to cytoplasmic protein-complexes and is involved in translational repression of transcripts (86). DOZI knockouts showed severe reduction in the levels of many sexual stage specific transcripts, presumably because they were subject to rapid degradation when not protected in ribonucleoprotein (RNP) complexes. We speculate that SAP1 might be an essential component of such an RNP complex in sporozoites that protects UIS transcripts and its absence leads to specific degradation of UIS transcripts. This scenario however requires further investigation. Interestingly, proteins with glutamine and asparagine-rich domains have recently been shown to be part RNP complexes in yeast where they act as scaffolding proteins (87).

Pysap1(−) sporozoites showed complete attenuation of liver infection. This can be attributed to the lack of the essential proteins UIS3, UIS4 and P52 and possibly additional UIS in the knockout parasite and not to a lack of a direct effector function of SAP1. Single and double gene deletion sporozoites are extremely effective live attenuated vaccines in mouse models (reviewed in 56) and we have shown herein that Pysap1(−) sporozoites also confer sterile protection against WT sporozoite challenge. *P. falciparum* gene deletion mutants are likely going forward for testing as human malaria vaccines. We suggest that a putative *P. falciparum* sap1(−) sporozoite may be an attractive live attenuated vaccine candidate because of its quasi-multi-locus attenuation. Together our data give important first insights into the regulation of the malaria parasite infectivity after mosquito transmission and this might advance efforts to develop measures for prevention of malaria infection.

EXAMPLE 5

This Example summarizes the following publication (105): Labaied, M., Harupa, A., Dumpit, R. F., Coppens, I., Mikolajczak, S. A., and Kappe, S. H. I., *Plasmodium yoelii* Sporozoites with Simultaneous Deletion of P52 and P36 are Completely Attenuated and Confer Sterile Immunity against Infection, *Infection and Immunity* (2007) 75(8):3758-68, published electronically ahead of print on May 21, 2007, which is hereby incorporated by reference in its entirety. The Example further provides additional data on protection of mice after rechallenge.

Malaria infection starts when sporozoites are transmitted to the mammalian host during a mosquito bite. Sporozoites enter the blood circulation, reach the liver and infect hepatocytes. The formation of a parasitophorous vacuole (PV) establishes their intracellular niche. Recently, two members of the 6-cys domain protein family, P52 and P36, were shown to each play an important albeit non-essential role in *Plasmodium berghei* sporozoite infectivity for the rodent host. Here, we generated p52(−)/p36(−) deficient *Plasmodium yoelii* parasites by simultaneous deletion of both genes using a single genetic manipulation. p52(−)/p36(−) parasites exhibited normal progression through the life cycle during blood stage infection, transmission to mosquitoes, mosquito stage development and sporozoite infection of the salivary glands. p52(−)/p36(−) sporozoites also showed normal motility and cell traversal activity. However, immunofluorescence analysis and electron microscopic observations revealed that p52(−)/p36(−) parasites did not form a PV within hepatocytes in vitro and in vivo. The p52(−)/p36(−) parasites localized as free entities in the host cell cytoplasm or the host cell nucleoplasm and did not develop as liver stages. Consequently they did not cause blood stage infections even at high sporozoite inoculation doses. Mice immunized with p52(−)/p36(−) sporozoites were completely protected against infectious sporozoite challenge. Our results demonstrate for the first time the generation of two-loci gene deletion-attenuated parasites that infect the liver but do not progress to blood stage infection.

In the present published study, a triple immunization regimen with *P. yoelii* p52(−)/p36(−) sporozoites completely protect against intravenous sporozoite injection and mosquito bite challenge (105). Specifically, mice immunized with three doses of 1.0×10⁴ p52(−)/p36(−) sporozoites showed complete protection against challenge with 1.0×10⁴ wild-type sporozoites 7 and 30 days after the last immunization. Furthermore, the same triple immunization regimen conferred complete protection against sporozoite challenge by mosquito bite. These results indicate that p52(−)/p36(−) sporozoites are able to induce sterile protection against a challenge with high doses of infectious sporozoites as well as against natural mosquito infection.

The additional data provided in Table 5, below, shows that mice remain protected after re-challenge on days 240 and 224, respectively.

TABLE 5

Protection of BALB/c mice immunized with Py52(−)/36(−) sporozoites against challenge with Pywt sporozoites

|  | Balb/cJ | Balb/cJ | Control |
| --- | --- | --- | --- |
| Primary p52(−)/p36(−) sporozoites | 1.0 × 10⁴ | 1.0 × 10⁴ | — |
| Boosts p52(−)/p36(−) sporozoites[a] | 1.0 × 10⁴(d7)/ 1.0 × 10⁴(d14) | 1.0 × 10⁴(d7)/ 1.0 × 10⁴(d14) | — |
| Challenge dose wt sporozoites[b] | 1.0 × 10⁴(d7) | 1.0 × 10⁴(d30) | — |
| Re-Challenge dose wt sporozoites[c] | 1.0 × 10⁴(d240) | 1.0 × 10⁴(d224) | 1.0 × 10⁴(−) |
| No. protected/ No. challenged/ pre-patency[d] | 8/8/− | 7/7/− | 0/5/d3 |

[a]Number of sporozoites injected for first boost / second boost. Days after primary shown in parentheses.
[b]Immunized mice were challenged with Pywt sporozoites by iv injection. Days after final boost shown in parentheses.
[c]Protected mice from first challenge were injected iv with Pywt sporozoites. Days after first challenge are shown in parentheses.
[d]Pre-patency is the number of days after sporozoite inoculation until detection of a single erythrocytic stage by blood smear examination.

EXAMPLE 6

This example describes vectors useful for generating loss-of-function *P. falciparum* parasites.

To disrupt the function of genes in *Plasmodium falciparum* (e.g., UIS3, UIS4, LSA-1, p52, p36, Etramp "Y", Etramp "Z", S22, FabI and FabG), plasmids are constructed that can integrate into targeted genes by double crossover homologous recombination using plasmids pHHT-Tk, pCC1 and pCC4 for negative selection using either thymidine kinase (Tk), or the *Saccharomyces cerevisiae* cytosine deaminase/ uracil phosphoribosyl transferase gene. Vectors pHHT-Tk and pCC1 contain a hDHFR cassette (driven by a calmodulin promoter) flanked by 2 multiple cloning sites to accept targeting sequence of the relevant gene, whereas vector pCC4 contains a blasticidin deaminase (bsd) cassette (driven by a calmodulin promoter) flanked by 2 multiple cloning sites to accept targeting sequence of the relevant gene. They also include a negative selection cassette (driven by an Hsp86 promoter region) to select parasites in which double recombination events occur.

To construct vector pHH-Tk, We amplified the cytosine deaminase (CD) gene from *E. coli* using the primers CD1 5'-GGACCGCTCGAGTTTTTATGTCGAATAACGCTTTA CAAACAATT-3' (SEQ ID NO: 30) and CD2 5'-GGAC- CCTCGAGTCAACGTTTGTAGTCGATGGCTTCTGG-3' (SEQ ID NO: 31). Following digestion of the PCR product with Xho I CD was inserted into the Xho I site of the plasmid transfection vector pHH1 (100), between the *Plasmodium falciparum* hsp86 promoter and the *Plasmodium berghei* dhfr-thymidylate synthase gene terminator, to give the construct pHCD. Two DNA segments of approximately 1 kb from the Pfrh3 pseudogene (Accession no. AF324831) were amplified from *Plasmodium falciparum* 3D7 genomic DNA and introduced into the flanking regions of the human dhfr cassette to mediate the integration of the plasmid into the parasite genome. The 5' segment of Pfrh3 was amplified from genomic DNA of 3D7 parasites with the primers Pfrh3-1 5'-GGACCCCGCGGAAAACTTTCAGTTTTCAC-3' (SEQ ID NO: 32) and Pfrh3-2 5'-GGACCGTTAACCTC- CCAATATTCTCTTGTCC-3' (SEQ ID NO: 33). This was introduced 5' of the hdhfr cassette between the Sac II and Hpa I sites of pHCD. The 3' segment of the Pfrh3 gene was amplified with the primers Pfrh3-3 5'-GGACCACCGGTAGC- CTAGGGACGGATTAGTTGAAAATAAATCC-3' (SEQ ID NO:34) and Pfrh3-4 5'-GGACCGGGCGCCCGGGTTTC-CCATCAACTAAGG-3' (SEQ ID NO: 35). An XmaI site was introduced instead of the KasI site and the 3' fragment cloned into this to give the plasmid pHCD-rh3. The thymidine kinase (Tk) gene from Herpes simplex virus was amplified from the vector pTCTK (obtained from Dr. Michael White, Montana State University) using the primers Tk1 5'-GGACCGCTC-GAGTTTTTATGGCTTCGTACCCCTGCCATCAAC-3' (SEQ ID NO: 36) and Tk2 5'-GGACCGCTCGAGTCAGT-TAGCCTCCCCCATCTCCC-3' (SEQ ID NO: 37) and cloned into the pHCD-rh3 vector in place of the cytosine deaminase (CD) gene to give the plasmid pHTK-rh3. Both the Tk and CD genes were sequenced prior to transfection.

To generate pCC1, we modified pGEM7Z(+) (Promega) by annealing a polylinker consisting of oligonucleotides aw132 5' ctagagtagatctgtcttaaggtggatc-cgtaagcttgtgaattcgtgagct 3' (SEQ ID NO: 38) and aw133 5' cacgaattcacaagcttacggatccaccttaagacagatctact 3' (SEQ ID NO: 39) into the XbaI/SacI sites of pGEM7Z(+). This yielded the cloning vector LT-1. We then amplified firefly luciferase from pPf86 (101) with primers aw118 5' atcggatcctttttatggaa-gacgccaaaaacataaagaaaggcccgg 3' (SEQ ID NO: 40) and aw119 5' gatgataagcttacacggcgatctttccgccc 3' (SEQ ID NO: 41), and cloned it into the BamHI/HinDIII sites of LT-1 creating the vector LT-2. The 3' UTR of the gene encoding the histidine rich protein 2 (HRP2 3') was cut out of the vector pHHT-TK (47) with HinDIII/EcoRI and annealed into LT-2. The 5' UTR of the *P. falciparum* calmodulin (CAM) gene was amplified with primers aw76 5' caatggcccctttcttaagcattttg 3' (SEQ ID NO: 42) and aw77 5' gcatggatcctgatatatttctattagg 3' (SEQ ID NO: 43) from pHHT-TK and ligated into the HRP2 3' containing LT-2. This plasmid was named LT-3.

The 3' UTR of the *P. berghei* dihydrofolate reductase/thymidylate synthase (PbDT 3') was amplified with the oligonucleotides aw122 5' atccccggggtaccctgcaggtc-gacttaattaaggatatggcagcttaatgttcgttttc 3' (SEQ ID NO: 44) and aw123 5' tactactagcggccgcctaccctgaagaag 3' (SEQ ID NO: 45), and ligated into the NotI/XmaI cut plasmid pHHT-TK resulting in pHHT-TK-3'.

The firefly luciferase was cut out of LT-3 with BamHI/HinDIII and replaced with the human dehydrofolate reductase gene (hDHFR) from pHHT-TK. The hDHFR containing LT-3 was then cut with EcoRI/AflII to release the whole hDHFR gene cassette (with the CAM5' and HRP2 3') and cloned into EcoRI/AflII cut pHHT-TK-3'.

The resulting vector was named pDC-1 and contains a CAM5'-hDHFR-HRP2 3' gene cassette for positive selection and a HSP86 5'-Herpex simplex TK-PbDT 3' gene cassette for negative selection. The component of each gene cassette can be individually cut out and replaced (hence the vector is modular). Each gene cassette is flanked by a multiple cloning site. In addition the vector contains a plasmid backbone, which enables ampicillin selection in *E. coli* and replication both in *E. coli* and *P. falciparum*.

Finally, the ScFCU gene was amplified with the primers aw500 5' atcctcgagatggtgacaggggaatg 3' (SEQ ID NO: 46) and aw501 5' ggatcccgggttaaacacagtagta 3' (SEQ ID NO: 47) from the plasmid pHHT-FCU-ΔPF11_0037 (90) and cloned XhoI/XmaI into the cut pDC-1 to replace the HsTK gene with the ScFCU gene (CDUP). The final vector was then called pCC-1.

pCC-4 is a derivative of pCC-1, where the hDHFR gene is replaced by the gene for blasticidin-S deaminase (BSD), which confers resistance to blasticidin-S.

Plasmid DNA was extracted using Maxiprep kits from either Qiagen or Invitrogen (Purelink). 80 μg DNA was transfected using standard protocols. After positive selection on WR99210 (2 nM final concentration) or blasticidin (2 μg/ml final concentration), the cells were placed under negative selection using either Ganciclovir (Roche, 20 μM, pHHT-TK) or 5-Fluorocytosine (ICN, 100 nM, pCC1 and pCC4). Any resulting cell populations underwent Southern blot analysis. Genomic DNA was prepared with the Dneasy Tissue Kit (Qiagen) and Southern Blot analysis performed using the DIG system (Roche) according to manufacturer's instructions to confirm disruption of the targeted genes.

EXAMPLE 7

This example describes the generation of loss-of-function *P. falciparum* parasites using FLP recombinase to remove the positive selectable marker.

To disrupt the function of genes in *Plasmodium falciparum* (e.g. UIS3, UIS4, LSA-1, p52, p36, Etramp "Y", Etramp "Z", S22, FabI and FabG), derivatives of pCC1 containing FRT sequences to catalyze recombination for deletion of the positive selectable marker (e.g. hDHFR) are used. The following primers with FRT sites are used for amplifying the targeting flanks: reverse primer for 5' flank (FRT1R) 5'-GAAGTTC-CTATACTTTCTAGAGAATAGGAACTTC-3' (SEQ ID NO: 48) and forward primer for 3' flank (FRT1F) 5'-GAAGTTC-CTATTCTCTAGAAAGTATAGGAACTTC-3' (SEQ ID NO: 49) pCC1-derivatives use CDUP to select parasites in which the construct integrates by homologous double crossover recombination. pCC1 uses the positive selectable marker hDHFR. Targeting sequences (e.g. 5' flanks and 3' flanks) for homologous recombination into the gene of interest are also cloned into the vectors. A schematic of this approach is shown in FIG. 3.

Plasmid DNA is extracted using Maxiprep kits from either Qiagen or Invitrogen (Purelink). 80 μg DNA is transfected using standard protocols. After positive selection on WR99210 (2 nM final concentration) or blasticidin (2 μg/ml final concentration), the cells are placed under negative selection using either Ganciclovir (Roche, 20 μM, pHHT-TK) or 5-Fluorocytosine (ICN, 100 nM, pCC1 and pCC4). Any resulting cell populations undergo Southern blot analysis. Genomic DNA is prepared with the Dneasy Tissue Kit (Qiagen) and Southern Blot analysis performed using the DIG system (Roche) according to manufacturer's instructions to confirm disruption of the targeted genes.

Following genetic disruption, to remove the positive selectable marker, a second vector based on pCC4 (pCC4-FLP) containing the positive selectable marker bsd as described supra (e.g., EXAMPLE 5) and flp recombinase driven by an Hsp86 promoter region is introduced to the parasites (e.g. by transfection), to catalyse deletion of the positive selectable marker genes in *Plasmodium falciparum*. Following positive selection for the flp-recombinase containing-vector on blasticidin, recovered cell populations undergo Southern blot analysis. Genomic DNA is prepared with the Dneasy Tissue Kit (Qiagen) and Southern Blot analysis performed using the DIG system (Roche) according to manufacturer's instructions to confirm removal of the positive selectable marker (e.g. hDHFR) from the confirmed disruption of targeted genes.

EXAMPLE 8

This example describes the generation of loss-of-function *P. falciparum* parasites using Cre recombinase to remove the positive selectable marker.

To disrupt the function of genes in *Plasmodium falciparum* (e.g. UIS3, UIS4, LSA-1, p52, p36, Etramp "Y", Etramp "Z", SAP1 (S22), FabI and FabG), derivatives of pCC1 containing loxP sequences to catalyze recombination for deletion of the positive selectable marker (e.g. hDHFR) are used. The following primers with loxP sites are used for amplifying the targeting flanks: reverse primer for 5' flank (loxP1R) 5' ATAACTTCGTATAGCATACATTATACGAAGTTAT 3' (SEQ ID NO: 50) and forward primer for 3' flank (loxP1F) 5' ATAACTTCGTATAATGTATGCTATACGAAGTTAT 3' (SEQ ID NO: 51). pCC1-derivatives use CDUP to select parasites in which the construct integrates by homologous double crossover recombination. pCC1 uses the positive selectable marker hDHFR (e.g., FIG. 4). Targeting sequences (e.g. 5' flanks and 3' flanks) for homologous recombination into the gene of interest are also cloned into the vectors. A schematic of this approach is shown in FIG. 4.

Plasmid DNA is extracted using Maxiprep kits from either Qiagen or Invitrogen (Purelink). 80 µg DNA is transfected using standard protocols. Following positive selection on WR99210 or blasticidin, the cells are placed under negative selection using either Ganciclovir (Roche, 20 µM, pHHT-TK) or 5-Fluorocytosine (ICN, 100 nM, pCC1 and pCC4). Any resulting cell populations undergo Southern blot analysis. Genomic DNA is prepared with the Dneasy Tissue Kit (Qiagen) and Southern Blot analysis performed using the DIG system (Roche) according to manufacturer's instructions to confirm disruption of the targeted genes.

Following genetic disruption, to remove the positive selectable marker, a second vector based on pCC4 (pCC4-Cre) containing the positive selectable marker bsd as described supra (e.g., EXAMPLE 6) and cre recombinase driven by an Hsp86 promoter region is introduced to the parasites (e.g. by transfection), to catalyse deletion of the positive selectable marker genes in Plasmodium falciparum. Following positive selection for the cre-recombinase containing-vector on blasticidin, recovered cell populations undergo Southern blot analysis. Genomic DNA is prepared with the Dneasy Tissue Kit (Qiagen) and Southern Blot analysis performed using the DIG system (Roche) according to manufacturer's instructions to confirm removal of the positive selectable marker (e.g. hDHFR) from the confirmed disruption of targeted genes.

EXAMPLE 9

This example describes the genetic disruption of LSA-1 in *P. falciparum* parasites.

To disrupt the function of LSA-1 in *Plasmodium falciparum*, the vector pCC4-LSA-1 KO was constructed. This vector contains two cassettes the first containing bsd for positive selection using blasticidin driven by the calmodulin promoter (5' CAM) and has the histidine rich protein 2 terminator (3' hrp2). The second cassette has the CDUP gene for negative selection with 5-FC and is driven by the heat shock protein 86 promoter (5' hsp86) and flanked by the *Plasmodium berghei* dhfr terminator (3' PbDT). The plasmid backbone contains the cassette for bacterial expression and selection (AMP). Targeting sequences (e.g. 5' flanks and 3' flanks) for homologous recombination into LSA-1 are also cloned into the vector. The following primers were used: 5' flank forward (LSA15F) 5' atatCCGCGGgaagttcctattctctagaaagtataggaacttcCTGAAA-CATATTTTGTACATATCATTTTAC 3' (SEQ ID NO: 52); 5' flank reverse (LSA15R) 5' atatACTAGTCTAGATCTTCT-TGTCTGTTTTCG 3' (SEQ ID NO: 53); 3' flank forward (LSA13F) 5' atatCCATGGCAGCTATAGAACTTCCAT-CAG 3' (SEQ ID NO: 54); and 3' flank reverse (LSA13R) 5' atatGGCGCCgaagttcctatactttctagagaataggaacttcGATAATT CTTCTGATGATTTTTCTATTC 3' (SEQ ID NO: 55).

The plasmid pCC4-LSA-1 KO was introduced into *Plasmodium falciparum* parasites by transfection of ring-stage parasites (~5% parasitemia) with 80 µg of purified plasmid DNA (Qiagen) using standard procedures. After 6 h the culture medium (RPMI-HEPES with 10% heat inactivated human serum) was changed and blasticidin (e.g. blasticidin-5-hydrochloride) was added to a final concentration of 2.5 ug/ml. Fresh media and blasticidin was added every 24 h for the next 5 days and every 48 h thereafter. After the establishment of blasticidin resistant parasites (25-32 days) 5-FC (Ancotil ICN) was added while maintaining selection with blasticidin. This procedure allows positive selection for parasites that had integrated this cassette by double crossover recombination with blasticidin and negative selection with 5-FC against those that retained the episomal plasmid.

To determine if these parasites had integrated the bsd selection cassette into the LSA-1 gene wet used Southern blot hybridization on genomic DNA cut with restriction enzymes Hind III and Sca I or Eco RI alone, which shows the predicted sizes of the digested fragments in kbp, and digests of wild-type (e.g. untransfected) *Plasmodium falciparum* (WT), and the transfected lines par1 and par3 when probed with DNA corresponding to either the 5' or 3' flanks, respectively. The bands obtained were those expected for a double crossover homologous recombination of the bsd cassette into the LSA-1 gene in the parasite lines par1 and par3 (WT, 7.6 kb band, genetic disruption, 4.3 kb band, and WT, 4.8 kb band, genetic disruption, 2.1 kb band, when probed with the 5' and 3' flanks, respectively), indicating that LSA-1 had indeed been disrupted with the bsd cassette integrated by homologous double crossover recombination across the 5' and 3' flanks.

EXAMPLE 10

This example describes the genetic disruption of p52 and p36, respectively, in *P. falciparum* parasites.

Irradiated, live-attenuated *Plasmodium* sporozoite stages infect the liver, abort development and confer sterile protection against subsequent malaria infection in animal models and humans. This level of protection is unmatched by recombinant malaria vaccines, which have generated only incomplete protection (98, 99). However, the live-attenuated vaccine approach faces obstacles that need solutions including accurate, reproducible attenuation techniques. Herein we demonstrate for the first time the use of precise genetic engineering to attenuate the most lethal human malaria parasite *Plasmodium falciparum*. The genetically attenuated parasites (GAPs) harbor individual deletions of the sporozoite-expressed genes p52 and p36. Deletions do not affect parasite replication throughout the erythrocytic cycle and sporozoite production rates in mosquitoes are comparable to wildtype parasites. However, the deletions cause parasite developmental arrest during infection of hepatocytes. The developmental phenotype of GAPs suggests their potential to elicit protective immune responses against liver stage malaria in humans and thus their utility as a live, whole-organism vaccine against *P. falciparum* malaria infection.

Methods

Recombinant protein expression and antisera production: The nucleotide sequence for the signal peptide and the GPI anchor were excluded from the expression constructs for genes encoding the P36 and P52 proteins. The P36 expression construct contains coding sequence started from $G_{48}$ through the end of the protein, $S_{353}$, into pEU-E01-GST plasmid between the XhoI and BamHI sites. P52 expression construct contains $S_{44}$ through $K_{458}$ as above. Both recombinant proteins were expressed in the wheat germ cell-free protein expression system as GST-fusion proteins (25), and were purified using the glutathione-Sepharose 4B column (GE Healthcare Bio-Sciences, Piscataway, N.J.). The affinity-purified proteins were used to obtain immune sera in mice or rabbits. The animals were immunized three times in three weeks interval subcutaneously using Freund's adjuvant. Pre-immune sera and antisera obtained from animals immunized with GST in Freund's adjuvant were used as negative controls.

Immunofluorescent labeling of native P52 protein in sporozoites: Salivary gland sporozoites were extracted from mosquitoes by dissection and deposited on slides, 3,000 per well. After air-drying the slides were fixed with ice-cold acetone and blocked with 5% non-fat dry milk in PBS for 30 minutes at 37° C. Sporozoites were incubated for one hour at 37° C. with mouse or rabbit anti-P52 sera and anti-TRAP sera, washed with ice-cold PBS and incubated anti-rabbit and anti-mouse secondary antibodies conjugated either with Alexa Fluor®488 or 546 (Invitrogen), and DAPI (2 µg/mL) for 30 minutes at 37° C. After further washing, slides were mounted with Prolong Gold Antifade Reagent (Invitrogen). The images were taken by confocal scanning laser microscopy (LSMS PASCAL; Carl Zeiss MicroImaging, Thornwood, N.Y.).

Design and production of gene targeting constructs: Pfp52 (GenBank: XP_001351357—PlasmoDB: PFD0215c) and Pfp36 (GenBank: XP_001351356—PlasmoDB: PFD0210c) are paralogous tandem-arranged genes on chromosome 4. Their products exhibit a predicted N-terminal cleavable signal peptide followed by two 6-cys domains, but unlike P36, P52 exhibits a C-terminal hydrophobic sequence predicted to be a putative GPI anchor attachment signal (25). The *P. falciparum* proteins P52 and P36 exhibit 40% and 43% amino acid identity to their respective *P. yoelii* orthologs.

Targeting sequences for *P. falciparum* p52 and p36 were cloned into plasmid pCC1 to facilitate positive-negative selection (89). Restriction sites in the multiple cloning site (MCS) were SacII/SpeI for the 5' flank and AvrII/SfoI for the 3' flank. Sequencing was performed to confirm inserts. Primers used were as follows: p52 5' flank forward (p525F) 5'-atatCCGCGGgaagttcctattctctagaaagtataggaacttcGGATC TCTATAAATGCATGAGG-3' (SEQ ID NO: 56) and 5' flank reverse (p525R) 5'-atatACTAGTCTGGGT-GAGTTTTTGCCG-3', (SEQ ID NO: 57); 3' flank forward p523F) 5'-atatCCTAGGCAAGGAAAAAAATTAAGG GTTGTG-3' (SEQ ID NO: 58) and 3' flank reverse (p523R) 5'-atatGGCGCCgaagttcctatactttctagagaataggaacttcGTTCA TTTATATATTTGGAAATATCATC-3' (SEQ ID NO: 59); p36 5' flank forward (p365F) 5'-atatCCGCGGgaagttcctat-tctctagaaagtataggaacttcGGAGAGTATAGCAAAATGTTG C-3' (SEQ ID NO: 60) and 5' flank reverse (p365R) 5'-atatAC-TAGTGTGCATGTTTCATTAGCATAATCC-3' (SEQ ID NO: 61), 3' flank forward (p363F) 5'-atatCCTAGGGG-GAATTTACATGCCATTCTATG-3' (SEQ ID NO: 62) and 3' flank reverse (p363R) 5'-atatGGCGCCgaagttc-ctatactttctagagaataggaacttcCCTATACCCTTCCCTTGTG-3' (SEQ ID NO: 63).

Transfection of *P. falciparum* with targeting constructs: Plasmid DNA was extracted by maxi prep kit (QIAGEN). The 3D7 *P. falciparum* parasites (Walter Reed Army Institute for Research) were synchronized at ring stage with sorbitol two days prior to transfection. On the following day trophozoites were selected for WT cytoadherence properties by incubation in RPMI plus Gelofusine (Braun). Transfection of *P. falciparum* ring stages with 100 µg of DNA was performed by electroporation at 0.31 kV and 950 µF with a BioRad Gene Pulser (BioRad, La Jolla, Calif.). Cultures were placed on the positive selection drug WR99210 (Jacobus Pharmaceuticals, Princeton, N.J.) 6 hours post-transfection and maintained as described (106).

RT-PCR and Southern blot: 2.4 million *P. falciparum* sporozoites per parasite line were used for RNA extraction with TRIzol (Invitrogen) and treated with amplification grade DNAseI (Invitrogen). cDNA was synthesized with Super Script III Platinum RT-PCR kit (Invitrogen). Amplification with p52 and p36 gene-specific primers was done for 35 cycles at 94° C. 30 sec, 55° C. 30 sec, 60° C. 2 min. Primers used for P52 were: forward (P52F) 5'-CCAGAAAATTGC-CCTTCTAGAGCCTTTGTT-3' (SEQ ID NO: 64), reverse (P52R) 5'-GCCCAATACATCATTTGAATAAGCATG-3' (SEQ ID NO: 65). Primers used for P36 were: forward (P36F) 5'-TGTTTACACTCGAATGTGGGATGGCATCCT-3' (SEQ ID NO: 66), reverse (P36R) 5'-GAATGGCATG-TAAATTCCCACATTATATCT-3' (SEQ ID NO: 67). Genomic DNA from WT 3D7 and knockout lines was digested for 2-16 hours with the following enzymes: P52 5' and 3' HindIII/ClaI, P36 5' EcoRI/EcoRV and 3' EcoRI. Digested DNA was run on a 1% TAE agarose gel at 15 v for 18 hours and transferred to Hybond-N membrane (Amersham) overnight at room temperature, UV crosslinked and pre-hybridized with herring sperm DNA for 2.5 hours. A Digoxygenin-labelled probe was prepared by PCR per supplier protocol (Roche) using the cloning primers. Hybridization was carried out for 18 hours at 55° C. The blot was exposed to film for 10-60 minutes and developed per standard protocol.

Gametocyte cultures: WT *P. falciparum* and knockout lines were cultured in vitro using pooled human A+ sera (Interstate Blood Bank, Memphis, Tenn.), RPMI-Hepes (Life Technologies/GIBCO), hypoxanthine (Sigma) and washed, type O+ erythrocytes. Media was changed daily and exflagellation was observed at room temperature by phase-contrast microscopy at 200× magnification beginning 12 to 13 days after the cultures were initiated. Parasites from the cultures were fed to the mosquitoes when the majority of the gametocytes were morphologically mature and vigorous exflagellation was observed.

*Anopheles stephensi* aged 4-7 days were pre-starved for 2-4 hours and then fed for a minimum of 30 minutes on 37° C. culture using a membrane feeder apparatus with bandruche membrane (Joseph Long Inc., Belleville, N.J.). One cage of 250-300 mosquitoes was exposed to concentrated erythrocytes from a 30 mL gametocyte culture mixed with an equal volume of fresh erythrocytes and 2 volumes of serum. Mosquitoes were incubated at 27° C., 80% humidity and sporozoites were harvested at 16-22 days post-infection.

Sporozoite counts and motility assays: Twenty thousand sporozoites were seeded per well on 12-well glass slides previously coated with 3% BSA in RPMI-1640. The slides were incubated at 37° C. for 1 hour. They were fixed for 10 min with 4% paraformaldehyde at room temperature, and were washed with 1% FBS in 1×PBS. Slides were then blocked with 10% FCS/PBS overnight at 4° C. Sporozoite trails were immunostained by incubation with anti-PfCSP monoclonal antibody for 45 minutes at 37° C. They were washed with 1% FCS/PBS, Slides were incubated with (1:200) anti-mouse IgG AlexaFluor 488 (Molecular Probes) for 45 minutes at 37° C. and they were washed with 1% FCS/PBS. Slides were mounted using Vectashield mounting medium (Vector Labs, Burlingame, Calif.). They were observed at 400× magnification by epifluorescence microscopy using an Olympus BX 50 microscope. Quantification was performed by direct microscopic counting of triplicate wells.

In vitro invasion and development assays: To assess invasion 25,000 sporozoites were added per well to a HC04 cells monolayer on 8 well glass Labtek chamber Slides™ They were incubated 3 hours at 37° C. and 5% $CO_2$. Slides were washed with PBS and were fixed with cold methanol. Slides were incubated 30 minutes with anti-CSP mAb, at room temperature, washed with PBS and blocked with 0.1% BSA/PBS followed by a 1:200 HRP goat anti-mouse IgG (Kirkegaard and Perry, Gaithersburg, Md.) as secondary antibody for 30 minutes at room temperature. Slides were mounted using Permount (Fisher Scientific). Intracellular sporozoites were counted using microscopy at 200× magnification in triplicate wells.

Development assays were performed by adding 60,000 sporozoites per well to HC-04 cells monolayers in 8 well Permanox Labtek chamber Slides™. Excess sporozoites were removed and cells washed after a three hour incubation at 37° C. and 5% $CO_2$. Cultures were maintained with daily medium changes for 72, 96, and 144 hours. Chamber slides were methanol fixed and stained using a mAb against HSP-70 (mAb 4C9) as primary antibody and Alexa Fluor 488 anti-mouse IgG (Molecular Probes) as the secondary antibody diluted in 0.1% Evans blue/PBS in a similar manner as described above. Slides were mounted using Vectashield plus DAPI (Vector Labs, Burlingame, Calif.). The total number of liver stages per well were counted in triplicate wells using an Olympus BX 50 epifluorescent microscope. Parasites were observed by epifluorescence microscopy at 400× magnification. Photographs were taken using a BioRad Radiance 2100 Confocal microscope.

In vivo assessment of infection in hepatic chimera murine model: Five to fourteen day old SCID mice homozygous for the urokinase type plasminogen activator transgene (SCID Alb-uPA) received an inoculation, by intrasplenic injection, with $10^6$ human hepatocytes that had been isolated (with informed consent) from surgically resected liver specimens by collagenase digestion and Percoll gradient centrifugation (107). Mice were screened 6 weeks post transplant for successful hepatocyte engraftment by serum analysis for human alpha one antitrypsin by ELISA. Chimeric mice received an intravenous tail vein injection of $1-1.5\times10^6$ P. falciparum WT or p36(-) sporozoites, were euthanized by $CO_2$ overdose at 4 days post-infection and their livers removed for cryosectioning or RNA extraction. Livers were rinsed in PBS and the lobes cut into separate pieces. Selected lobes were embedded in Tissue-Tek O.C.T. compound (Miles Scientific, Naperville, Ill.) and frozen in an isopentane/liquid $N_2$ bath, while other pieces were flash frozen in liquid $N_2$ for RNA extraction. Tissue sections (7 μm) were cut on a Leica CM1900 (Leica Microsystems, Deerfield, Ill.), fixed in absolute methanol, and stored at −80° C. until used. Diluted antisera (anti-CSP and anti-HSP70 and anti-LSA1) were then applied to the tissue section (in a volume sufficient to cover the tissue) and the slides were then incubated for 30 min. at 37° C. in a humidity chamber. Liver section slides were placed in a staining dish and washed 3 times for 5 min. with PBS. A fluorescein-conjugated IgG (Kirkegaard and Perry, Gaithersburg, Md.) was used as the secondary antibody. The secondary antibody was diluted 1:40 into PBS containing 0.02% Evan's blue. The Evan's blue was added to act as a counterstain to suppress any autofluorescence in the tissue. The diluted secondary antibody was added and the slides placed in a humidity chamber, in the dark, and incubated at 37° C. for 30 min. Tissue sections were then washed and the slides mounted, using Vectashield® mounting media (Vector Labs, Burlingame, Calif.). The stained slides were screened with a Nikon Eclipse E600 epifluorescent microscope and digital images collected with a SPOT digital camera (Diagnostic Instruments, Inc., Sterling Hgts, Mich.).

RNA for use in RT-PCR analysis was isolated from infected liver as previously described (97). Briefly, first-strand cDNA was generated from total RNA using the SuperScript First-Strand Synthesis System for RT-PCR kit (Life Technologies, Gaithersburg, Md.). cDNA synthesis was performed by priming RNA, isolated from the different parasite samples with random hexamers, and then incubation with reverse transcriptase (RT+). As a control for the presence of genomic DNA, reactions were done omitting the reverse transcriptase (RT−). Amplification of specific P. falciparum 18S gene sequences or human glyceraldehyde phosphate dehydrogenase (GAPDH) was accomplished by PCR using a hot start Taq DNA polymerase from the HotStarTaq PCR kit (Qiagen, Valencia, Calif.). One microliter from the cDNA reaction was added to a PCR master mix with 18S primers (forward (18SF), 5'-AATCTTGAACGAGGATGCC-3' (SEQ ID NO: 68); reverse (18SR), 5'-GGAAACCTTGTTAC-GACTTCTCC-3' (SEQ ID NO: 69)) or GAPDH primers (forward (GAPDHF), 5'-GAAGGTGAAGGTCGGAGTC-3' (SEQ ID NO: 70); reverse (GAPDHR), 5'-GAAGATGGT-GATGGGATTTC-3' (SEQ ID NO: 71)). PCR products were electrophoresed on a 1% agarose gel and visualized by staining with ethidium bromide.

Results

Subcellular localization of P52 and P36: To determine the subcellular localization of P. falciparum P52 and P36, we expressed each protein in a wheat-germ cell free expression system (108). Polyclonal antisera were raised in mice and rabbits and reactivity was tested in immunoflourescence assays (IFAs) using P. falciparum sporozoites. A specific sporozoite-internal staining was observed for P52 that co-localized with the micronemal protein TRAP. The fluorescence was only observed in sporozoites after permeabilization of membranes, indicating that P52 localizes to the secretory organelles of sporozoites. Pre-immune sera did not show reactivity with sporozoites (data not shown). Unfortunately, antisera raised against P36 did not react with sporozoites in IFA (data not shown) and therefore localization was not determined.

Deletion of P. falciparum P52 and P36: To delete P52 and P36 from the parasite genome, we used a positive-negative selection strategy (89). Double crossover homologous recombination between targeting sequences in transfection constructs and the endogenous genes resulted in replacement of PfP52 and PfP36 individually with the human dihydrofolate reductase (dhfr) selectable marker (109). Two independently transfected lines of the P. falciparum gametocyte-producing clone 3D7 were generated for each targeted locus. Transfectant parasites appeared between days 21 and 35 post-transfection under positive selection with WR99210 (109). Parental transfectant populations were removed from positive selection for a three-week period and then subjected to positive selection until a stable population was established after two weeks. This was followed by negative selection against cytosine deaminase-uracil phosphoribosyltransferase with 5-fluorocytosine. Transfectant lines were then analyzed by Southern blot to detect the gene deletions. Clonal lines of recombinant parasites were derived from the parental population by limiting dilution and analyzed for successful gene deletion and absence of wildtype (WT) by Southern blot. The Southern blot analysis confirmed the genetic homogeneity of the knockouts.

P52- and P36-deficient *P. falciparum* parasites show normal infectivity and development in the mosquito: Deletion of PfP52 and PfP36 in the erythrocytic stage did not result in any observable defect during blood stage replication (data not shown), indicating that these genes have no apparent function that is critical during this part of the parasite life cycle. In addition, the morphology of male and female gametocytes in thin blood smears and male gamete exflagellation in wet mounts were indistinguishable from WT parasites (data not shown).

Gametocyte stage parasite cultures were used to infect *Anopheles stephensi* mosquitoes by membrane feeding. Evaluation of midgut oocyst infection in mosquitoes showed no discernible differences between WT, P52$^-$ and P36$^-$ knockout lines (data not shown). This indicated that gene deletions did not affect the sexual stages of the parasite. Furthermore, it provided evidence that prolonged culture of knockout parasite lines (4-6 months) during drug selection did not significantly reduce knockout parasite transmissibility to mosquitoes. Importantly, invasion of the mosquito salivary glands appeared normal in the P52 and P36 knockout lines because numbers of sporozoites isolated from the glands were comparable to those isolated from WT parasites (Table 6).

TABLE 6

Phenotypic analysis of Pf52- and Pf36-deficient sporozoites and liver stages

|  | WT | P52- | P36- |
|---|---|---|---|
| No. salivary gland spz/mosquito | 45,233 ± 24,624 | 57,162 ± 7,535 | 67,667 ± 29,365 |
| Spz trails in motility assay | 1.00 (referent) | 0.92 ± 0.11 | 0.91 ± 0.13 |
| Relative invasion rates | 1.00 (referent) | 1.04 ± 0.07 | 1.00 ± 0.13 |
| Relative liver stage parasite abundance at 72 hours | 1.00 (referent) | 0.70 ± 0.11 | 0.65 ± 0.10 |

P52- and P36-deficient *P. falciparum* sporozoites are biologically active: To ensure that gene deletions result in complete lack of expression of P52 or P36 we performed RT-PCR on sporozoite RNA isolated from WT and knockout parasite lines. Results indicated that p52$^-$ sporozoites did not express transcripts for P52 but expressed transcripts for P36; conversely, p36$^-$ knockout sporozoites expressed transcripts for P52 but not for P36.

It has been shown that both the viability and biological activity of sporozoites are reflected in their motility on a solid substrate that can be assessed by using anti-circumsporozoite (CS) protein, the main sporozoite surface protein (110). No significant differences in motility and CS protein shedding were observed between WT, p52$^-$ and p36$^-$ lines as evidenced by deposition of trails stained with anti-CSP antibodies (Table 6).

P52- and P36-deficient *P. falciparum* parasites invade but exhibit developmental arrest in hepatocytes: We investigated the ability of p52$^-$ and p36$^-$ sporozoites to invade host cells in vitro using HC-04 hepatocytes a cell line that supports invasion and complete liver stage development of *P. falciparum* (111). Invasion was assessed microscopically by counting the number of cells invaded by sporozoites; invasion rates were comparable among WT and knockout parasite lines indicating that the lack of P52 and P36 did not impact sporozoite host cell entry (Table 6).

Next, intracellular development of knockout parasite liver stages was compared to WT parasite development in HC-04 cells at 3-, 4- and 6 days after sporozoite infection. (Table 6).

At day 3, knockout parasites did not show significant deficiencies in liver stage growth. However, at day 4 knockout parasite liver stages exhibited smaller sizes across infected HC-04 cultures when compared to WT parasites and at day 6 knockout parasite liver stages showed clear growth arrest when compared to well developed WT parasite liver stages.

P-36-deficient *P. falciparum* sporozoites fail to productively infect the livers of humanized SCID alb-uPA mice: Because the liver phase of *P. falciparum* only develops in human hepatocytes and is therefore not adequately assessed in conventional animal models we used a humanized mouse model (97) to study infectivity of the single knockout parasite p36$^-$. Immunodeficient mice homozygous for the urokinase type plasminogen activator transgene (SCID Alb-uPA) were inoculated with $10^6$ primary human hepatocytes to create chimeric human-mouse livers (107). After 6 weeks successful engraftment was evaluated. Positive engrafted chimeric mice were infected intravenously with $10^6$ sporozoites of either p36$^-$ (n=6) or WT (n=3) *P. falciparum* and livers were harvested four days post-infection. Tissue sections of livers were labeled with antisera against parasite HSP70 and LSA-1 and examined by immunofluorescence microscopy. In contrast to liver stage development observed in livers of mice infected with WT *P. falciparum* no p36$^-$ parasites were observed (data not shown). To further evaluate p36$^-$ infection in the chimeric mice we performed RT-PCR analysis on liver tissue. Whilst WT liver stages were easily detected 4 days post infection by amplification of parasite 18S rDNA no amplification was observed from livers infected with p36$^-$ parasites. Together the data indicate that the *P. falciparum* GAPs are attenuated and cannot develop successfully in human hepatocytes.

Discussion

Here, we targeted two loci in *P. falciparum*, P52 and P36, for deletion. Deletion of the orthologous genes in the rodent malaria models had indicated that they are critical for productive liver infection (71, 72, 105). Transmission to the mosquito vector and passage through the mosquito stages were not affected by deletion of either P52 or P36. Furthermore, although loss of gametocyte production and transmissibility has been reported after prolonged culture of *P. falciparum*, the selection procedure for cytoadherence we employed to minimize loss of chromosome ends (112) appeared to have avoided this problem. The p52$^-$ and p36$^-$ lines showed normal mosquito salivary gland infection rates and knockout salivary gland sporozoites exhibited normal gliding motility demonstrating that the biological activity of knockout sporozoites was not affected up to this point in the parasites' developmental cycle.

Further analysis of the human parasite pre-erythrocytic stages has been challenging because no traditional animal models, except chimpanzees, exist that allows in vivo evaluation of liver infection. Nonetheless, liver infection can be modeled in hepatocyte cultures and we made use of the HC-04 continuous hepatocyte cell line that was shown to support complete liver stage development of *P. falciparum* (111). Cell infection rates of the p52$^-$ and p36$^-$ lines were comparable to those of WT *P. falciparum*, indicating that lack of P52 or P36 did not affect host cell entry. However, the knockouts showed clear defects in liver stage development. This became most pronounced 6 days after infection when WT parasites had developed large cell masses whereas knockout parasites appeared arrested at an early developmental stage. It is noteworthy that P52 and P36 are each apparently critical for liver infection. Although the genes are paralogues and share a similar expression profile, neither compensates functionally for the loss of the other. The *P. falciparum* p52$^-$ and p36$^-$ phenotypes are therefore similar to the phenotypes observed for the corresponding rodent malaria knockouts (71, 72, 105).

In order to further assess the developmental phenotype of the knockout parasites in vivo, we tested Pfp36⁻ in an immunodeficient chimeric mouse model that carries human hepatocyte transplants (97, 107). p36⁻ parasites were not detected after four days of hepatic development. In contrast, WT parasites were detected in the chimeric livers 4 days after infection by RT-PCR as well as histological methods. The findings in conjunction with the in vitro observations suggest that the knockout parasites may infect the chimeric mice but do not persist in the chimeric livers. The findings are in agreement with previous work in *P. yoelii* that showed rapid decline of GAPs in the liver of mice (55, 105).

Together, our results demonstrate the critical role of P52 and P36 in *P. falciparum* hepatocyte infection. Our work is the first demonstration of specific attenuation of *P. falciparum* in early hepatocyte infection. The phenotype of arrested liver stage development exhibited by the p52⁻ and p36⁻ *P. falciparum* indicates their potential as a live-attenuated vaccine against malaria. Such live attenuated vaccines can be tested for safety (i.e., breakthrough blood stage infection) and efficacy using the established human sporozoite challenge model (103). To add an additional element of safety, a GAP vaccine might be comprised of a p52⁻/p36⁻ line that carries deletions of both genes. In the *P. yoelii* model, a p52⁻/p36⁻ GAP did not show any breakthrough infection when inoculated at high doses of $10^5$ sporozoites. Furthermore this GAP vaccine induced sterile protection against high dose challenge with $10^4$ WT sporozoites and against natural infectious bite (105). A *P. falciparum* live vaccine that has been attenuated by gene deletion offers the advantages of genetic homogeneity, standardization, testable genetic identity and possibly improved safety of the vaccine with regard to breakthrough infections. These are critical factors on the path to development of a live-attenuated human malaria vaccine.

EXAMPLE 11

This example describes the simultaneous genetic disruption of p52 and p36 in *P. falciparum* parasites and their characterization.

Methods

Design and production of gene targeting constructs: The p52 and p36 genes are adjacent to one another in the *Plasmodium falciparum* genome. To disrupt the function of both p52 and p36 in a single population of *Plasmodium falciparum* parasites the vector pCC1-P52/P36 KO was constructed. Targeting sequences for *P. falciparum* P52 and P36 were cloned into plasmid pCC1 to facilitate positive-negative selection (89). Restriction sites in the MCS were SacII/SpeI for the 5' flank and AvrII/SfoI for the 3' flank. Sequencing was performed to confirm inserts. A schematic of this approach is shown in FIG. 5.

Furthermore, to disrupt the function of both p52 and p36 in a single population of *Plasmodium falciparum* parasites, and remove the positive selectable marker following genetic disruption, a vector derivative of pCC1 containing lox sequences (pCC1-Lox) to catalyze recombination for deletion of the positive selectable marker following genetic disruption was constructed. pCC1-derivatives use CDUP to select parasites in which the construct integrates by homologous double crossover recombination. pCC1-P52/P36 KO uses the positive selectable marker hDHFR. Targeting sequences (e.g., 5' flank and 3' flank) for homologous recombination into the gene of interest are also cloned into the vector. pCC1-LoxP-P52/P36 contains mutant lox sites, lox66 and lox71, adjacent to the positive selectable marker cassette. The primers used for disrupting both genes with loxP sites were as follows: P52 5' flank: P525flF: 5'-ATATCCGCGGGGATCTCTATAAAT-GCATGAGG -3' (SEQ ID NO: 72) and P525flR: 5'-ATATAC-TAGTATAACTTCGTATAATGTATGCTATACGAACGG TACTGGGTGAGTTTTTGCCGTAGTACTAAAAGCAT CATTC -3' (SEQ ID NO: 73); and P36 3' flank: P363flF: 5'-ATATCCTAGGATAACTTCGTATAATGTATGCTATAC GAACGGTAGGGAATTTACATGCCATTCTATGTAAA GGAAGATATAAC-3' (SEQ ID NO: 74) and P363flR: 5'-ATATGGCGCCCCTATACCCTTCCCTTGTG-3' (SEQ ID NO: 75).

Transfection of *P. falciparum* with targeting constructs: The pCC1-P52/P36 KO plasmid was introduced into *Plasmodium falciparum* parasites by transfection of ring-stage parasites (~5% parasitemia) with 100 µg of purified plasmid DNA (Qiagen) by electroporation at 0.31 kV and 950 µF with a BioRad Gene Pulser (BioRad, La Jolla, Calif.). The pCC1-LoxP-P52/P36 KO plasmid was similarly introduced into a separate population of *Plasmodium falciparum* parasites. After 6 hours, the culture medium (RPMI-HEPES with 5% AlbumaxII (Invitrogen) and 5% heat inactivated human serum) was changed and 6 nM WR99210 (Jacobus Pharmaceuticals) was added. Fresh media and WR99210 was added every 24 h for the next 5 days and every 48 h thereafter. After the establishment of WR99210 resistant parasites (25-32 days) 5-FC (Ancotil® ICN) was added while maintaining selection with WR99210. This procedure allows positive selection for parasites that had integrated this cassette by double crossover recombination with WR99210 and negative selection with 5-FC against those that retained the episomal plasmid.

RT-PCR and Southern blot: 2.4 million column purified *P. falciparum* spz per parasite line were used for RNA extraction with TRIzol (Invitrogen) and treated with Turbo DNAse (AMbion). cDNA was synthesized with Super Script III Platinum RT-PCR kit (Invitrogen). Amplification with p52 and p36 gene-specific primers was done at 94° C. 30 seconds, 55° C. 30 seconds, 60° C. 2 minutes for 35 cycles. Primers used for p52 were: forward (P52F) 5'-CCAGAAAATTGCCCT-TCTAGAGCCTTTGTT-3' (SEQ ID NO: 64), reverse (P52R) 5'-GCCCAATACATCATTTGAATAAGCATG-3' (SEQ ID NO: 65). Primers used for p36 were: forward (P36F) 5'-TGTTTACACTCGAATGTGGGATGGCATCCT-3' (SEQ ID NO: 66), reverse (P36R) 5'-GAATGGCATG-TAAATTCCCACATTATATCT-3' (SEQ ID NO: 67).

Genomic DNA from wild-type 3D7 and mutant lines was digested for 2-16 hours with the following enzymes: P52 5' and 3' HindIII/ClaI, P36 5' EcoRI/EcoRV and 3' EcoRI. Digested DNA was run on a 1% TAE agarose gel at 15 v for 18 hours and transferred to Hybond-N membrane (Amersham) membrane overnight at room temperature, UV crosslinked and pre-hybridized with herring sperm DNA for 2.5 hours. Digoxygenin-labelled probe was prepared by PCR per supplier protocol (Roche) using the cloning primers. Hybridization was carried out for 18 hours at 55° C. The blot was exposed to film for 10-60 minutes and developed per standard protocol.

Gametocyte cultures: Wild-type Pf strain NF54 and mutant Pf lines are cultured in vitro using pooled human A+ sera (Interstate Blood Bank, Memphis, Tenn.), RPMI-Hepes (Life Technologies/GIBCO), hypoxanthine (Sigma) and washed, type O+ erythrocytes. Media is changed daily and exflagellation is checked at room temperature by phase-contrast microscopy at 200× magnification beginning 12 to 13 days after the cultures are initiated. Parasites from the cultures are fed to the mosquitoes when the majority of the gametocytes are morphologically mature and vigorous exflagellation is observed. *Anopheles stephensi* aged 4-7 days are pre-starved for 2-4 hours and then fed for a minimum of 30 minutes on 37° C. culture by membrane feeder apparatus with bandruche membrane (Joseph Long Inc., Belleville, N.J.). One cage of 250-300 mosquitoes is exposed to concentrated erythrocytes from a 30 mL gametocyte culture mixed with an equal volume of fresh erythrocytes and 2 volumes of serum. Mosquitoes are incubated at 27° C., 80% humidity and sporozoites are harvested at 16-22 days post-infection.

Sporozoite counts and motility assays: Ten to twenty thousand sporozoites are seeded into wells on 12-well glass slides coated with 3% BSA in RPMI-1640. The sporozoites are incubated at 37° C. for 1 hour, fixed for 10 minutes at room temperature with 4% paraformaldehyde, and washed thrice with 1% FBS in 1×PBS. Wells are then blocked with 10% FCS/PBS for 45 minutes at 37° C. Sporozoite trails are stained for IFA by incubation with anti-PfCSP monoclonal antibody for 45 minutes at 37° C. and observed at 400× magnification by phase-contrast microscopy.

In vitro invasion and development assays: Sporozoites are extracted from mosquito salivary glands by dissection, seeded 50,000/well onto ECL-coated slides and incubated 3 hours at 37° C. at 5% $CO_2$. Slides are washed 3 times with PBS and fixed with cold methanol. Cells are incubated 30 minutes with anti-CSP mAb, washed and stained with HRP goat anti-mouse IgG for 30 minutes. Intracellular sporozoites are counted using a phase-contrast microscope at 200× magnification. Development assays are performed over 72, 96, and 144 hour incubation periods and stained with antisera against EXP-1 (kind gift of Klaus Lingelbach) and monoclonals against HSP-70 (mAb 4C9) and LSA-1 (mAb 5C5) in a similar manner as described above. Total exoerythrocytic forms per well are counted in triplicate wells.

In vitro development of liver stages in hepatic chimera murine model (97): All experiments use sporozoites of the 3D7 strain or P36 knockout strain of *Plasmodium falciparum*. Sporozoites are reared in *Anopheles stephensi* mosquitoes and are isolated by hand dissection in Medium 199 (Gibco, Grand Island, N.Y.) with 5% fetal calf serum. Five to fourteen day old SCID mice homozygous for the urokinase type plasminogen activator transgene (SCID Alb-uPA) receive an inoculation, by intrasplenic injection, with $10^6$ human hepatocytes that have been isolated (with informed consent) from surgically resected liver specimens by collagenase digestion and Percoll gradient centrifugation (107). Mice are screened 6 weeks post transplant for successful hepatocyte engraftment by serum analysis for human alpha one antitrypsin by ELISA. Mice are cared for by the University of Maryland School of Medicine Veterinary Resources under a protocol approved by the University of Maryland School of Medicine Institutional Animal Care and Use Committee.

Chimeric mice receive an intravenous tail vein injection of $1-1.5\times10^6$ *P. falciparum* sporozoites, are euthanized by $CO_2$ overdose at 4 or 7 days post-infection and their livers removed for cryosectioning or RNA extraction. Livers are rinsed in PBS and the lobes cut into separate pieces. Selected lobes are embedded in Tissue-Tek O.C.T. compound (Miles Scientific, Naperville, Ill.) and frozen in an isopentane/liquid $N_2$ bath, while other pieces were flash frozen in liquid $N_2$ for RNA extraction. Tissue sections (7 μm) are cut on a Leica CM1900 (Leica Microsystems, Deerfield, Ill.), fixed in absolute methanol, and stored at −80° C. until used.

Slides with tissue sections are stored at −70° C. wrapped in foil and a plastic bag. Tissue section slides are removed from the freezer, placed in a desiccators and allowed to equilibrate to room temperature. Diluted antisera (anti-circumsporozoite protein, *Plasmodium* Heat Shock Protein 70, Liver stage antigen-1 and merozoite surface protein-1) are then applied to the tissue section (in a volume sufficient to cover the tissue) and the slides are then incubated for 30 minutes at 37° C. in a humidity chamber. Liver section slides are placed in a staining dish and washed 3 times for 5 minutes with PBS. A fluorescein-conjugated IgG (Kirkegaard and Perry, Gaithersburg, Md.) is used as the secondary antibody. The specificity of the secondary antibody varies depending upon the species of the primary antibody used to stain the sections. The secondary antibody is diluted 1:40 into PBS containing 0.02% Evan's blue. The Evan's blue is added to act as a counterstain to suppress any autofluorescence in the tissue. The diluted secondary antibody is added and the slides placed in a humidity chamber, in the dark, and incubated at 37° C. for 30 min. Tissue sections are then washed and the slides mounted, using Vectashield® mounting media (Vector Labs, Burlingame, Calif.). The stained slides are screened with a Nikon Eclipse E600 epifluorescent microscope and digital images collected with a SPOT digital camera (Diagnostic Instruments, Inc., Sterling Hgts, Mich.).

RNA for use in RT-PCR analysis is isolated from infected liver as previously described (97). Briefly, first-strand cDNA is generated from total RNA using the SuperScript First-Strand Synthesis System for RT-PCR kit (Life Technologies, Gaithersburg, Md.). cDNA synthesis is performed by priming RNA, isolated from the different parasite samples with random hexamers, and then incubation with reverse transcriptase (RT+). As a control for the presence of genomic DNA, reactions are done omitting the reverse transcriptase (RT−). Amplification of specific *P. falciparum* 18S gene sequences or human glyceraldehyde phosphate dehydrogenase (GAPDH) is accomplished by PCR using a hot start Taq DNA polymerase from the HotStarTaq PCR kit (Quiagen, Valencia, Calif.). One microliter from the cDNA reaction is added to a PCR master mix with 18S primers (forward (18SF), 5'-AATCTTGAACGAGGATGCC (SEQ ID NO: 68); reverse (18SR), 5'-GGAAACCTTGTTACGACTTCTCC-3' (SEQ ID NO: 69) or GAPDH primers (forward (GAPDHF), 5'-GAAGGTGAAGGTCGGAGTC-3' (SEQ ID NO: 70); reverse (GAPDHR), 5'-GAAGATGGTGATGGGATTTC-3' (SEQ ID NO: 71)). PCR products are electrophoresed on a 1% agarose gel and visualized by staining with ethidium bromide.

Results

Generation of p52(−) and p36(−) null parasite lines: Double crossover homologous recombination between targeting sequences in transfection constructs and the endogenous genes resulted in replacement of p52 and p36 with the human dhfr selectable marker. Two independently transfected lines were produced for each locus targeted. Transfectant parasites appeared between day 21 and 35 post-transfection. Parental transfectant populations were removed from positive selection for a three-week period and then underwent another round of positive selection, followed by negative selection with cytosine deaminase. Transfectant lines were then analyzed by Southern blot and RT-PCR to detect gene disruption.

To determine if parasites had integrated the hDHFR selection cassette into the p52/p36 locus, we used Southern blot hybridisation on genomic DNA cut with restriction enzymes Hind III and Cla I, which show the predicted sizes of the digested fragments in kbp, and digests of wild-type (e.g., untransfected) *Plasmodium falciparum* (WT), and two transfected lines (parA and parB) when probed with DNA corresponding to the 3' flank. The bands shown were those expected for a double crossover homologous recombination of the hDHFR cassette into the p52/p36 locus in the parasite lines (WT, 5.8 kb band, genetic disruption, 2.7 kb band, when probed with the 3' flank). This indicates that p52 and p36 had indeed been disrupted with the hDHFR cassette integrated by homologous double crossover recombination across the 5' and 3' flanks. Similarly, a parasite population in which p52 and p36 had been disrupted with the hDHFR cassette integrated by homologous double crossover recombination using pCC1-LoxP-P52/P36 KO was obtained.

Discussion

We targeted two loci in *P. falciparum*, p52 and p36, for deletion. The endogenous genes were replaced with the human dhfr selectable marker via double crossover homologous recombination. These experiments were designed to evaluate the roles of P52 and P36 in *P. falciparum* sporozoite and liver stage development, as well as their potential for generating *P. falciparum* genetically attenuated parasites (GAPs).

Whole-organism vaccines are thought to be the most promising vaccine strategy against *Plasmodium*. Subunit vaccines designed to elicit immunity against the blood-stages have generated only incomplete protection (98, 99). Irradiation of sporozoites offered a model of immunity directed toward the hepatic stages of the parasite. The advantages of a homogeneous, standardized line of genetically-attenuated *Plasmodium* as a vaccine spurred efforts to create GAPs in rodent malaria species; the success of these lines in eliciting protective immunity supports the feasibility of generating attenuated *P. falciparum* that will induce malaria immunity in the human host.

EXAMPLE 12

This example describes the removal of the positive selectable marker from *P. falciparum* parasites with simultaneous genetic disruption of p52 and p36.

Following genetic disruption, to remove the positive selectable marker, a second vector based on pCC4 (pCC4-Cre) containing the positive selectable marker bsd and cre recombinase driven by an Hsp86 promoter region is introduced to the parasites (e.g. by transfection), to catalyze deletion of the positive selectable marker genes in *Plasmodium falciparum*. Following positive selection for the loxP-recombinase containing-vector on blasticidin, recovered cell populations undergo Southern blot analysis. Genomic DNA is prepared with the Dneasy Tissue Kit (Qiagen) and Southern Blot analysis performed using the DIG system (Roche) according to manufacturer's instructions to confirm removal of the positive selectable marker (e.g. hDHFR) from the confirmed disruption of targeted genes. The resulting parasite population lacking the sequences between the loxP sites (e.g. the positive selectable marker) is genetically disrupted for both p52 and p36.

EXAMPLE 13

This example describes the genetic disruption of Etramp "Y" in *P. falciparum* parasites.

To disrupt the function of Etramp "Y" (also known as PF14_0729) in *Plasmodium falciparum*, the vector pCC1-ΔPF14_0729 was constructed. This vector contains two cassettes the first containing hDHFR for positive selection using WR99210 driven by the calmodulin promoter (5' CAM) and has the histidine rich protein 2 terminator (3' hrp2). The second cassette has the CDUP gene for negative selection with 5-FC and is driven by the heat shock protein 86 promoter (5' hsp86) and flanked by the *Plasmodium berghei* dhfr terminator (3' PbDT). The plasmid backbone contains the cassette for bacterial expression and selection (AMP). Furthermore, to disrupt the function of PF14_0729 and remove the positive selectable marker following genetic disruption, a vector derivative of pCC1 containing FRT sequences (pCC1-FRT-ΔPF14_0729) to catalyze recombination for deletion of the positive selectable marker following genetic disruption was constructed. Targeting sequence for homologous recombination into PF14_0729 (e.g. 5' flank: Y51 5' atcccgcgGT-GTAGATTAAAAGAATCTGTTG 3' (SEQ ID NO: 76) and Y52 5' gatactagtCCTTAAAATGGCTATTAATACCC 3' (SEQ ID NO: 77) 3' flank: Y31 5' atcgaattcGCAGTTG-GAATATGGAAAACTAG 3' (SEQ ID NO: 78) and Y32 5' gatcctagGTGCATACCGTTCCAAATTGAC 3' (SEQ ID NO: 79) are also cloned into the vectors.

The pCC1-ΔPF14_0729 plasmid was introduced into *Plasmodium falciparum* parasites by transfection of ring-stage parasites (~5% parasitemia) with 80 µg of purified plasmid DNA (Qiagen) using standard procedures. The pCC1-FRT-ΔPF14_0729 plasmid was similarly introduced into a separate population of *Plasmodium falciparum* parasites. After 6 h the culture medium (RPMI-HEPES with 5% AlbumaxII (Invitrogen) and 5% heat inactivated human serum) was changed and 6 nM WR99210 (Jacobus Pharmaceuticals) was added. Fresh media and WR99210 was added every 24 h for the next 5 days and every 48 h thereafter. After the establishment of WR99210 resistant parasites (25-32 days) 5-FC (Ancotil® ICN) was added while maintaining selection with WR99210. This procedure allows positive selection for parasites that had integrated this cassette by double crossover recombination with WR99210 and negative selection with 5-FC against those that retained the episomal plasmid.

To determine if parasites had integrated the hDHFR selection cassette into the PF14_0729 locus, we used Southern blot hybridization on genomic DNA cut with restriction enzymes Bam HI and Avr II, and Avr II and Eco RI, which show the predicted sizes of the digested fragments in kbp, and digests of wild-type (e.g., untransfected) *Plasmodium falciparum* (WT), and the transfected line (3D7ΔPF14_0729) when probed with DNA corresponding to either the 5' or 3' flank, respectively. The bands shown are those expected for a double crossover homologous recombination of the hDHFR cassette into the PF14_0729 locus in the parasite line 3D7ΔPF14_0729 (WT, 7.3 kb band, genetic disruption, 4.3 kb band, and WT, 9.0 kb band, genetic disruption, 4.9 kb band, when probed with the 5' and 3' flanks, respectively). This indicates that PF14_0729 had indeed been disrupted with the hDHFR cassette integrated by homologous double crossover recombination across the 5' and 3' flanks. Similarly, a parasite population in which PF14_0729 had been disrupted with the hDHFR cassette integrated by homologous double crossover recombination using pCC1-FRT-ΔPF14_0729 was obtained.

Following genetic disruption, the positive selectable marker is removed essentially as described in EXAMPLE 12.

EXAMPLE 14

This example describes the genetic disruption of UIS3, UIS4, Etramp "Z", FabI, or FabG in *P. falciparum* parasites.

To disrupt the function of UIS3, UIS4, Etramp "Z", FabI, or FabG in *Plasmodium falciparum*, the vectors pCC1-ΔUIS3, pCC1-ΔUIS4, pCC1-ΔEtramp Z, pCC1-ΔFabI, or pCC1-ΔFabG, respectively, are constructed. These vectors contain two cassettes the first containing hDHFR for positive selection using WR99210 driven by the calmodulin promoter (5' CAM) and has the histidine rich protein 2 terminator (3' hrp2). The second cassette has the CDUP gene for negative selection with 5-FC and is driven by the heat shock protein 86 promoter (5' hsp86) and flanked by the *Plasmodium berghei* dhfr terminator (3' PbDT). The plasmid backbone contains the cassette for bacterial expression and selection (AMP). Furthermore, to disrupt the function of UIS3, UIS4, Etramp "Z", FabI, or FabG, and remove the positive selectable marker following genetic disruption, vector derivatives of pCC1 containing loxP sequences (pCC1-loxP-UIS3, pCC1-loxP-UIS4, pCC1-loxP-EtrampZ, pCC1-loxP-FabI, or pCC1-loxP-FabG) to catalyze recombination for deletion of the positive selectable marker following genetic disruption are constructed. Targeting sequences (e.g. 5' flanks and 3' flanks) for homologous recombination into UIS3, UIS4, Etramp "Z", FabI, or FabG are also cloned into the vectors.

The following primers may be used for UIS3: 5' flank UIS35F1 5' atcccgcggCTCTTTTTTTATTTCATTTTA 3' (SEQ ID NO: 80) and UIS35F2 5' cggactagtGAAGTTCCTATACTTTCTAGAGAATAGGAACTTCttaGCTATCAATGAATAATAAATTA 3' (SEQ ID NO: 81); and 3' flank UIS33F1 5' atcgaattcGAAGTTCCTATTCTCTAGAAAGTATAGGAACTTcAAGATGGTGCTATAGCAAGTACTAGTGAATTTTATATAGAACC 3' (SEQ ID NO: 82) and UIS33F2 5' gatcctaggATAGATGTATTGTTCCCTCC 3' (SEQ ID NO: 83).

The following primers may be used for UIS4: 5' flank UIS45F1 5' atcccgcggCCATTTATCATAAAATTGTGGTCC 3' (SEQ ID NO: 84) and UIS45F2 5' gatactagtGAAGTTCCTATACTTTCTAGAGAATAGGAACTTCtta GTCGATATCCTTCAACGCTCTCTTATCATCATTTGCAG 3' (SEQ ID NO: 85); and 3' flank UIS43F1 5' atcgaattcGAAGTTCCTATTCTCTAGAAAGTATAGGAACTTCGGATCCGACTCTGAGGAATTAGATAGTTCTAAAGAGG 3' (SEQ ID NO: 86) and UIS43F2 5' gatcctagGTAACAAGCACATTACGTACAG 3' (SEQ ID NO: 87).

The following primers may be used for EtrampZ: 5' flank EtrampZ5F1 5' gatactagtGAAGTTCCTATACTTTCTAGAGAATAGGAACTTCttaCTTAAAATGGCTATTAATACCCATACCAAATATAGCTATTCC 3' (SEQ ID NO: 88) and EtrampZ5F2 5' atc gaattcGAAGTTCCTATTCTCTAGAAAGTATAGGAACTTcGCAGTTGGAATATGGAAAACTAGAAAAAATTACAAAAACG 3' (SEQ ID NO: 89); and 3' flank EtrampZ3F1 5' gatactagtATAACTTCGTATAGCATACATTATACGAAGTTATttaCTTAAAATGGCTATTAATACCCATACCAAATATAGCTATTCC 3' (SEQ ID NO: 90) and EtrampZ3F2 5' atcgaattcATAACTTCGTATAATGTATGCTATACGAAGTTAtGCAGTTGGAATATGGAAAACTAGAAAAAATTACAAAAACG 3' (SEQ ID NO: 91).

The following primers may be used for FabI: 5' flank FabI5F1 5' atcccgcggGAGTTTATTCATGTGGACATGTGC 3' (SEQ ID NO: 92) and 5' FabI5F2 atcactagtATAACTTCGTATAGCATACATTATACGAAGTTATgtt cattctgaagaacgttatgg 3' (SEQ ID NO: 93); and 3' flank FabI3F1 5' atcgaattcATAACTTCGTATAATGTATGCTATACGAAGTTATtgacgcttcttttgatactgc 3' (SEQ ID NO: 94) and FabI3F2 5' actcctaggATCCACATATATTGTCTGCC 3' (SEQ ID NO: 95).

The following primers may be used for FabG: 5' flank FabG5F1 5' atcccgcggGTGGTTATATATACACATAACTTAGC 3' (SEQ ID NO: 96) and FabG5F2 5' atcactagtATAACTTCGTATAGCATACATTATACGAAGTTATcaat ggaagaactttgtaaacaag 3' (SEQ ID NO: 97); and 3' flank FabG3F1 5' atcgaattcATAACTTCGTATAATGTATGCTATACGAAGTTATcaagtatagtagggttaacagg 3' (SEQ ID NO: 98) and FabG3F2 5' atccctaagCTTCTTCTGGTGTTCCCATTCG 3' (SEQ ID NO: 99).

The pCC1-ΔUIS3, pCC1-ΔUIS4, pCC1-ΔEtrampZ, pCC1-ΔFabI, or pCC1-ΔFabG plasmids are introduced into *Plasmodium falciparum* parasites by transfection of ring-stage parasites (~5% parasitemia) with 80 μg of purified plasmid DNA (Qiagen) using standard procedures. The pCC1-loxP-UIS3, pCC1-loxP-UIS4, pCC1-loxP-EtrampZ, pCC1-loxP-FabI, or pCC1-loxP-FabG plasmids are similarly introduced into separate populations of *Plasmodium falciparum* parasites. After 6 h the culture medium (RPMI-HEPES with 5% AlbumaxII (Invitrogen) and 5% heat inactivated human serum) is changed and 2-6 nM WR99210 (Jacobus Pharmaceuticals) added. Fresh media and WR99210 is added every 24 h for the next 5 days and every 48 h thereafter. After the establishment of WR99210 resistant parasites (25-32 days) 5-FC (Ancotil® ICN) is added while maintaining selection with WR99210. This procedure allows positive selection for parasites that had integrated this cassette by double crossover recombination with WR99210 and negative selection with 5-FC against those that retained the episomal plasmid.

To determine if parasites have integrated the hDHFR selection cassette into the UIS3, UIS4, Etramp "Z", FabI, or FabG loci, Southern blot hybridisation on genomic DNA cut with restriction enzymes is used to examine sizes of the digested fragments wild-type (e.g. untransfected) *Plasmodium falciparum* (WT), and the transfected lines (3D7ΔUIS3, 3D7ΔUIS4, 3D7ΔEtrampZ, 3D7ΔFabI, or 3D7ΔFabG) when probed with DNA corresponding to either the 5' or 3' flanks. This analysis allows examination of disruption of UIS3, UIS4, Etramp "Z", FabI, or FabG loci with the hDHFR cassette integrated by homologous double crossover recombination across the 5' and 3' flanks using the vectors.

Following genetic disruption, the positive selectable marker is removed essentially as described in EXAMPLE 12.

EXAMPLE 15

This example describes the administration of a vaccine composition comprising P56(−)/P36(−) null *P. falciparum* parasites to human volunteers to assess the safety and clinical efficacy.

P56(−)/P36(−) null *P. falciparum* sporozoites will be administered to approximately 42 healthy malaria-naive adults (non-pregnant). Subjects' exposure to the vaccine will consist of delivery of p52(−)/p36(−) sporozoites via mosquito bite in a controlled clinical environment per the well established challenge model (102-104). The first phase of the trial is a safety study that will consist of two experimental cohorts. The first cohort is comprised of subjects (n=6) who will receive bites from 5 infected mosquitoes in 1-pint cartons under controlled mosquito containment conditions. The second cohort is comprised of subjects (n=6) who will receive bites from 200 infected mosquitoes under the same controlled mosquito containment conditions. There will be a 4-week time period after dosing the first cohort to assess safety before dosing of the second cohort is initiated.

The clinical protocol design includes safety monitoring parameters in all cohorts. Criteria for initiation of the second phase (vaccination/challenge) of the study will be that the safety portion yielded the absence of evidence for blood infection (i.e., breakthrough). In this second phase, the vaccine will be administered to up to 30 healthy malaria-naive adults. Malaria challenge will follow with the 3D7 clone of the NF54 strain of *P. falciparum* 2-4 weeks and 6 months after the last delivery of the vaccine by mosquito bite in a controlled environment as previously described (102, 104). A control group of 6 healthy malaria-naïve adults (non-immunized infectivity controls) will be challenged at the same time as the vaccine administered group to score infectivity of the challenge batch. It is expected that there will be no breakthrough infections in the safety study after administration of P56(−)/P36(−) null *P. falciparum* sporozoites because it has already been shown that these sporozoites arrest development in the liver (see EXAMPLE 11). In the second phase of this clinical trial, it is anticipated that between 12/30 (40%) and 30/30 (100%) volunteers will be completely protected against challenge with the 3D7 clone, such as between 15/30 (50%) and 30/30 (100%), between 20/30 (67%) and 30/30 (100%), between 25/30 (83%) and 30/30 (100%), or between 27/30 (90%) and 30/30 (100%).

CITATIONS

The contents of each of the following publications is incorporated by reference herein.

1. Sachs, J. & Malaney, P. The economic and social burden of malaria. *Nature* 415:680-685 (2002).

2. Kappe, S. H., Kaiser, K. & Matuschewski, K. The *Plasmodium* sporozoite journey: a rite of passage. *Trends Parasitol.* 19:135-143 (2003).

3. Shortt, H. E. & Garnham, P. C. C. Pre-erythrocytic stage in mammalian malaria parasites. *Nature* 161:126 (1948).

4. Hoffman, S. L. Save the children. *Nature* 430:940-941 (2004).

5. Nussenzweig, R. S. et al. Protective immunity produced by the injection of X-irradiated sporozoites of *Plasmodium berghei. Nature* 216:160-162 (1967).

6. Hoffman, S. L. et al. Protection of humans against malaria by immunization with radiation-attenuated *Plasmodium falciparum* sporozoites. *J. Infect. Dis.* 185:1155-1164 (2002).

7. Hoffman, S. L. & Doolan, D. L. Malaria vaccines-targeting infected hepatocytes. *Nat. Med.* 6:1218-1219 (2000).

8. Gardner, M. J. et al. Genome sequence of the human malaria parasite *Plasmodium falciparum. Nature* 419:498-511 (2002).

9. Carlton, J. M. et al. Genome sequence and comparative analysis of the model rodent malaria parasite *Plasmodium yoelii yoelii. Nature* 419:512-519 (2002).

10. Hoffman, S. L. & Luke, T. G. Method for the prevention of malaria. WO 2004/045559 A2.

11. Matuschewski, K., J. Ross, S. M. Brown, K, Kaiser, V. Nussenzweig, and S. H. I. Kappe. Infectivity-associated changes in the transcriptional repertoire of the malaria parasite sporozoite stage. *J. Biol. Chem.* 277:41948-41953 (2002).

12. Kaiser, K., Matuschewski, K., Camargo, N., Ross, J. & Kappe, S. H. Differential transcriptome profiling identifies *Plasmodium* genes encoding pre-erythrocytic stage-specific proteins. *Mol. Microbiol.* 51:1221-1232 (2004).

13. V. Thathy and R. Ménard, Gene targeting in *Plasmodium berghei*, in Methods in Molecular Medicine, Vol. 72: Malaria Methods and Protocols, D. L. Doolan, Ed., Humana Press, 2002.

14. Noonpakdee, W., et al., Inhibition of *Plasmodium falciparum* proliferation in vitro by antisense oligodeoxynucleotides against malarial topoisomerase II, Biochem Biophys Res Commun. 302(4):659-64, 2003.

15. Gardiner, D. L., et al., Inhibition of *Plasmodium falciparum* clag9 gene function by antisense RNA, Mol Biochem Parasitol. 110(1):33-41, 2000

16. Al-Olayan, E. M., et al., Complete development of mosquito phases of the malaria parasite in vitro, Science 295:677-679, 2002.

17. Meis, J. F. et al. Malaria parasites—discovery of the early liver form. Nature 302:424 (1983).

18. Meis, J. F., & J. P. Verhave. Exoerythrocytic development of malarial parasites. *Adv Parasitol* 27:1 (1988).

19. Druilhe, P. L. et al. Immunity to Liver Stages. In Malaria: Parasite Biology, Pathogenesis and Protection. I. W. Sherman, ed. American Society for Microbiology, Washington D.C., P. 513 (1998).

20. Silvie, O., et al. Effects of irradiation on *Plasmodium falciparum* sporozoite hepatic development: implications for the design of pre-erythrocytic malaria vaccines. *Parasite Immunol.* 24:221 (2002).

21. Scheller, L. F., & A. F. Azad. Maintenance of protective immunity against malaria by persistent hepatic parasites derived from irradiated sporozoites. *Proc Natl Acad Sci USA* 92:4066 (1995).

22. Rosenberg, R. et al. An estimation of the number of malaria sporozoites ejected by a feeding mosquito. *Trans R Soc Trop Med Hyg* 84:209 (1990).

23. Beier, J. C. et al. Quantitation of malaria sporozoites transmitted in vitro during salivation by wild Afrotropical *Anopheles. Med Vet Entomol* 5:71 (1991).

24. Alger, N. E. et al. Sporozoite and normal salivary gland induced immunity in malaria. *Nature* 238:341 (1972).

25. Kappe, S. H., M. J. Gardner, S. M. Brown, J. Ross, K. Matuschewski, J. M. Ribeiro, J. H. Adams, J. Quackenbush, J. Cho, D. J. Carucci, S. L. Hoffman, and V. Nussenzweig. Exploring the transcriptome of the malaria sporozoite stage. *Proc Natl Acad Sci USA* 98:9895 (2001).

26. Le Roch, K. G. et al. Discovery of gene function by expression profiling of the malaria parasite life cycle. *Science* 301:1503 (2003).

27. Florens, L. et al. A proteomic view of the *Plasmodium falciparum* life cycle. *Nature* 419:520 (2002).

28. Guerin-Marchand, C. et al. A liver-stage-specific antigen of *Plasmodium falciparum* characterized by gene cloning. *Nature* 329:164 (1987).

29. Mueller, Ann-Kristin, Mehdi Labaied, Stefan H. I. Kappe, and Kai Matuschewski. Genetically modified *Plasmodium* parasites as a protective experimental malaria vaccine. *Nature* 433:164-167, 13 Jan. 2005. See also: Ménard, R. Knockout malaria vaccine? *Nature* 433:113-114, 13 Jan. 2005; and Waters, A. P. et al. Malaria vaccines: back to the future? *Science* 307:528-530, 28 Jan. 2005.

30. Sibley, L. D. Intracellular parasite invasion strategies. *Science* 304:248-253 (2004).

31. Meis, J. F. et al. Transformation of sporozoites of *Plasmodium berghei* into exoerythrocytic forms in the liver of its mammalian host. *Cell Tissue Res* 241:353-360 (1985).

32. Potocnjak, P. et al. Monovalent fragments (Fab) of monoclonal antibodies to a sporozoite surface antigen (Pb44) protect mice against malarial infection. *J. Exp. Med.* 151:1504-1513 (1980).

33. Tsuji, M. et al. Demonstration of heat-shock protein 70 in the sporozoite stage of malaria parasites. *Parasitol. Res.* 8016-21 (1994).

34. de Koning-Ward, T. F., et al. *Mol. Biochem. Parasitol.* 106:199-212 (2000).

35. Sultan, A. A., et al. TRAP is necessary for gliding motility and infectivity of *plasmodium* sporozoites. *Cell* 90:511-522 (1997).

36. Renia, L. et al. Malaria sporozoite penetration; a new approach by double staining. *J. Immunol. Methods* 112:201-205 (1988).

37. Dykxhoorn et al. Killing the messenger: Short RNAs that silence gene expression. *Nat. Rev. Mol. Cell Biol.* 4:457-67 (2003).

38. Novino & Sharp. The RNAi revolution. *Nature* 430: 161-164 (2004).

39. Reynolds et al. Rational siRNA design for RNA interference. *Nat. Biotechnol.* 22:326-30 (2004).

40. Heidel et al. Lack of interferon response in animals to naked siRNAs. *Nat. Biotechnol. DOI:*10.1038/nbt1038, Nov. 21, 2004.

41. Kumar et al. Characterization and expression of a PPI serine/threonine protein phosphatase (PfPP1) from the malaria parasite, *Plasmodium falciparum*: demonstration of its essential role using RNA interference. *Malar. J.* 1(1):5 (2002).

42. McRobert & McConkey. RNA interference (RNAi) inhibits growth of *Plasmodium falciparum*. *Mol. Biochem. Parasitol.* 119(2):273-8 (2002).

43. Malotra et al. Double-stranded RNA-mediated gene silencing of cysteine proteases (falcipain-1 and -2) of *Plasmodium falciparum*. *Mol. Microbiol.* 45(5):1245-54 (2002).

44. Mohmmed et al. In vivo silencing in *Plasmodium berghei*—a mouse malaria model. *Biochem. Biophys. Res. Commun.* 309(3):506-11 (2003).

45. Boutros et al. Genome-wide RNAi analysis of growth and viability in *Drosophila* cells. *Science* 303:832-5 (2004).

46. Kamath et al. Systematic functional analysis of the *C. elegans* genome using RNAi. *Nature* 421:231-7 (2003).

47. Duraisingh et al. Negative selection of *Plasmodium falciparum* reveals targeted gene deletion by double crossover recombination. *Int. J. Parasitol.* 32(1):81-9 (2002).

48. Vanderberg, J. P., and Frevert, U. (2004). Intravital microscopy demonstrating antibody-mediated immobilisation of *Plasmodium berghei* sporozoites injected into skin by mosquitoes. Int. J. Parasitol. 34, 991-996.

49. Amino, R., Thiberge, S., Martin, B., Celli, S., Shorte, S., Frischknecht, F., and Menard, R. (2006). Quantitative imaging of *Plasmodium* transmission from mosquito to mammal. Nat. Med. 12, 220-224.

50. Matuschewski, K. (2006). Getting infectious: formation and maturation of *Plasmodium* sporozoites in the *Anopheles* vector. Cell. Microbiol. 8, 1547-1556.

51. Kappe, S. H., Buscaglia, C. A., and Nussenzweig, V. (2004). *Plasmodium* sporozoite molecular cell biology. Annu. Rev. Cell. Dev. Biol. 20, 29-59.

52. Vanderberg, J. P. (1974). Studies on the motility of *Plasmodium* sporozoites. J. Protozool. 21, 527-537.

53. Vanderberg, J. P. (1975). Development of infectivity by the *Plasmodium berghei* sporozoite. J. Parasitol. 61, 43-50.

54. Mueller, A. K., Camargo, N., Kaiser, K., Andorfer, C., Frevert, U., Matuschewski, K., and Kappe, S. H. (2005). *Plasmodium* liver stage developmental arrest by depletion of a protein at the parasite-host interface. Proc. Natl. Acad. Sci. USA 102, 3022-3027.

55. Tarun, A. S., Dumpit, R. F., Camargo, N., Labaied, M., Liu, P., Takagi, A., Wang, R., and Kappe, S. H. (2007). Protracted sterile protection with *Plasmodium yoelii* pre-erythrocytic genetically attenuated parasite malaria vaccines is independent of significant liver-stage persistence and is mediated by CD8+ T cells. J. Infect. Dis. 196, 608-616.

56. Mikolajczak, S. A., Aly, A. S., and Kappe, S. H. (2007). Preerythrocytic malaria vaccine development. Curr. Opin. Infect. Dis. 20, 461-466.

57. Mikolajczak, S. A., Jacobs-Lorena, V., MacKellar, D. C., Camargo, N., and Kappe, S. H. (2007). L-FABP is a critical host factor for successful malaria liver stage development. Int. J. Parasitol. 37, 483-489.

58. Labaied, M., Harupa, A., Dumpit, R. F., Coppens, I., Mikolajczak, S. A., and Kappe, S. H. (2007). *Plasmodium yoelii* sporozoites with simultaneous deletion of P52 and P36 are completely attenuated and confer sterile immunity against infection. Infect. Immun. 75, 3758-3768.

59. Mikolajczak, S. A., and Kappe, S. H. (2006). A clash to conquer: the malaria parasite liver infection. Mol. Microbiol. 62, 1499-1506.

60. Silvie, O., Greco, C., Franetich, J. F., Dubart-Kupperschmitt, A., Hannoun, L., van Gernert, G. J., Sauerwein, R. W., Levy, S., Boucheix, C., Rubinstein, E., et al. (2006). Expression of human CD81 differently affects host cell susceptibility to malaria sporozoites depending on the *Plasmodium* species. Cell. Microbiol. 8, 1134-1146.

61. Janse, C. J., Franke-Fayard, B., Mair, G. R., Ramesar, J., Thiel, C., Engelmann, S., Matuschewski, K., van Gernert, G. J., Sauerwein, R. W., and Waters, A. P. (2006). High efficiency transfection of *Plasmodium berghei* facilitates novel selection procedures. Mol. Biochem. Parasitol. 145, 60-70.

62. Jongco, A. M., Ting, L. M., Thathy, V., Mota, M. M., and Kim, K. (2006). Improved transfection and new selectable markers for the rodent malaria parasite *Plasmodium yoelii*. Mol. Biochem. Parasitol. 146, 242-250.

63. Menard, R., and Janse, C. (1997). Gene targeting in malaria parasites. Methods 13, 148-157.

64. Khan, Z. M., and Vanderberg, J. P. (1991). Role of host cellular response in differential susceptibility of nonimmunized BALB/c mice to *Plasmodium berghei* and *Plasmodium yoelii* sporozoites. Infect. Immun. 59, 2529-2534.

65. Belmonte, M., Jones, T. R., Lu, M., Arcilla, R., Smalls, T., Belmonte, A., Rosenbloom, J., Carucci, D. J., and Sedegah, M. (2003). The infectivity of *Plasmodium yoelii* in different strains of mice. J. Parasitol. 89, 602-603.

66. Vanderberg, J. P., Chew, S., and Stewart, M. J. (1990). *Plasmodium* sporozoite interactions with macrophages in vitro: a videomicroscopic analysis. J. Protozool. 37, 528-536.

67. Mota, M. M., Pradel, G., Vanderberg, J. P., Hafalla, J. C., Frevert, U., Nussenzweig, R. S., Nussenzweig, V., and Rodriguez, A. (2001). Migration of *Plasmodium* sporozoites through cells before infection. Science 291, 141-144.

68. Mota, M. M., Hafalla, J. C., and Rodriguez, A. (2002). Migration through host cells activates *Plasmodium* sporozoites for infection. Nat. Med. 8, 1318-1322.

69. Bergman, L. W., Kaiser, K., Fujioka, H., Coppens, I., Daly, T. M., Fox, S., Matuschewski, K., Nussenzweig, V., and Kappe, S. H. (2003). Myosin A tail domain interacting protein (MTIP) localizes to the inner membrane complex of *Plasmodium* sporozoites. J. Cell Sci. 116, 39-49.

70. Parker, R., and Sheth, U. (2007). P bodies and the control of mRNA translation and degradation. Mol. Cell. 25, 635-646.

71. van Dijk, M. R., Douradinha, B., Franke-Fayard, B., Heussler, V., van Dooren, M. W., van Schaijk, B., van Gernert, G. J., Sauerwein, R. W., Mota, M. M., Waters, A. P., et al. (2005). Genetically attenuated, P36p-deficient malarial sporozoites induce protective immunity and apoptosis of infected liver cells. Proc. Natl. Acad. Sci. USA 102, 12194-12199.

72. Ishino, T., Chinzei, Y., and Yuda, M. (2005). Two proteins with 6-cys motifs are required for malarial parasites to commit to infection of the hepatocyte. Mol. Microbiol. 58, 1264-1275.

73. Baldacci, P., and Menard, R. (2004). The elusive malaria sporozoite in the mammalian host. Mol. Microbiol. 54, 298-306.

74. Ishino, T., Yano, K., Chinzei, Y., and Yuda, M. (2004). Cell-passage activity is required for the malarial parasite to cross the liver sinusoidal cell layer. PLoS. Biol. 2, E4.

75. Ishino, T., Chinzei, Y., and Yuda, M. (2005). A *Plasmodium* sporozoite protein with a membrane attack complex domain is required for breaching the liver sinusoidal cell layer prior to hepatocyte infection. Cell. Microbiol. 7, 199-208.

76. Kariu, T., Ishino, T., Yano, K., Chinzei, Y., and Yuda, M. (2006). CelTOS, a novel malarial protein that mediates transmission to mosquito and vertebrate hosts. Mol. Microbiol. 59, 1369-1379.

77. Aravind, L., Iyer, L. M., Wellems, T. E., and Miller, L. H. (2003). *Plasmodium* biology: genomic gleanings. Cell 115, 771-785.

78. Pizzi, E., and Frontali, C. (2001). Low-complexity regions in *Plasmodium falciparum* proteins. Genome Res. 11, 218-229.

79. Singh, G. P., Chandra, B. R., Bhattacharya, A., Akhouri, R. R., Singh, S. K., and Sharma, A. (2004). Hyperexpansion of asparagines correlates with an abundance of proteins with prion-like domains in *Plasmodium falciparum*. Mol. Biochem. Parasitol. 137, 307-319.

80. Xue, H. Y., and Forsdyke, D. R. (2003). Low-complexity segments in *Plasmodium falciparum* proteins are primarily nucleic acid level adaptations. Mol. Biochem Parasitol. 128, 21-32.

81. Nandi, T., Kannan, K., and Ramachandran, S. (2003). The low complexity proteins from enteric pathogenic bacteria: taxonomic parallels embedded in diversity. In silico boil. 3, 277-285.

82. Elemento, O., Slonim, N., and Tavazoie, S. (2007). A universal framework for regulatory element discovery across all genomes and data types. Mol. Cell. 28, 337-350.

83. Coulson, R. M., Hall, N., and Ouzounis, C. A. (2004). Comparative genomics of transcriptional control in the human malaria parasite *Plasmodium falciparum*. Genome Res. 14, 1548-1554.

84. Hakimi, M. A., and Deitsch, K. W. (2007). Epigenetics in Apicomplexa: control of gene expression during cell cycle progression, differentiation and antigenic variation. Curr. Opin. Microbiol. 10, 357-362.

85. Hall, N., Karras, M., Raine, J. D., Carlton, J. M., Kooij, T. W., Berriman, M., Florens, L., Janssen, C. S., Pain, A., Christophides, G. K., et al. (2005). A comprehensive survey of the *Plasmodium* life cycle by genomic, transcriptomic, and proteomic analyses. Science 307, 82-86.

86. Mair, G. R., Braks, J. A., Garver, L. S., Wiegant, J. C., Hall, N., Dirks, R. W., Khan, S. M., Dimopoulos, G., Janse, C. J., and Waters, A. P. (2006). Regulation of sexual development of *Plasmodium* by translational repression. Science 313, 667-669.

87. Decker, C. J., Teixeira, D., and Parker, R. (2007). Edc3p and a glutamine/asparagine-rich domain of Lsm4p function in processing body assembly in *Saccharomyces cerevisiae*. J. Cell Biol. 179, 437-449.

88. Quittnat, F., Nishikawa, Y., Stedman, T. T., Voelker, D. R., Choi, J. Y., Zahn, M. M., Murphy, R. C., Barkley, R. M., Pypaert, M., Joiner, K. A., et al. (2004). On the biogenesis of lipid bodies in ancient eukaryotes: synthesis of triacylglycerols by a *Toxoplasma* DGAT1-related enzyme. Mol. Biochem. Parasitol. 138, 107-122.

89. Maier et al. (2006) Negative selection using yeast cytosine deaminase/uracil phosphoribosyl transferase in *Plasmodium falciparum* for targeted gene deletion by double crossover recombination. Mol. Biochem. Parasitol. 150(1): 118-21.

90. Carvalho et al. (2004) Conditional mutagenesis using site-specific recombination in *Plasmodium berghei*, Proc. Natl. Acad. Sci. USA 101(41): 14931-6).

91. Gossen and Bujard, Proc. Natl. Acad. Sci. USA 1992, 89:5547-5551.

92. Meissner et al. (2005) Tetracycline analogue-regulated transgene expression in *Plasmodium falciparum* blood stages using *Toxoplasma gondii* transactivators, Proc. Natl. Acad. Sci. USA 102(8)2980-2985.

93. Leef J L, et al. Low-temperature preservation of sporozoites of *Plasmodium berghei*. Bull WHO 57 (suppl 1) 87-91, 1979.

94. Orjih A U, and Nussenzweig R S. Immunization against rodent malaria with cryopreserved irradiated sporozoites of *Plasmodium berghei*. Am J Trop Med Hyg 29(3): 343-7, 1980.

95. Campbell C C, Collins W E, Nguyen-Dinh P, Barber A, Broderson J R. *Plasmodium falciparum* gametocytes from culture in vitro develop to sporozoites that are infectious to primates. Science 217(4564):1048-50, 1982.

96. Chulay J D, Schneider I, Cosgriff T M, Hoffman S L, Ballou W R, Ouakyi I A, Carter R, Trosper J H, and Hockmeyer W T. Malaria transmitted to humans by mosquitoes infected from cultured *Plasmodium falciparum*. Am. J. Trop. Med. Hyg. 35(1):66-8, 1986 (January).

97. Sacci J B Jr, Alam U, Douglas D, Lewis J, Tyrrell D L, Azad A F, Kneteman N M. *Plasmodium falciparum* infection and exoerythrocytic development in mice with chimeric human livers. Int. J. Parasitol. 36, 353-360 (2006).

98. Alonso P L, Sacarlal J, Aponte J J, Leach A, Macete E, Milman J, Mandomando I, Spiessens B, Guinovart C, Espasa M, Bassat Q, Aide P, Ofori-Anyinam O, Navia M M, Corachan S, Ceuppens M, Dubois M C, Demoitié M A, Dubovsky F, Menéndez C, Tornieporth N, Ballou W R, Thompson R, Cohen J. Efficacy of the RTS, S/AS02A vaccine against *Plasmodium falciparum* infection and disease in young African children: randomised controlled trial. Lancet. 364, 1411-20.

99. Snounou G, Grüner A C, Müller-Graf C D, Mazier D, Rénia L. The *Plasmodium* sporozoite survives RTS, S vaccination. Trends Parasitol. 21, 456-61.100.

Reed M B, Saliba K J, Caruana S R, Kirk K, Cowman A F (2000) Pgh1 modulates sensitivity and resistance to multiple antimalarials in *Plasmodium falciparum*. Nature 403(6772): 906-9.

101. Militello K T, Wirth D F. A new reporter gene for transient transfection of *Plasmodium falciparum*. Parasitol Res. 2003 January; 89(2):154-7. Epub 2002 Aug. 23.

102. Chulay J D, Schneider I, Cosgriff T M, Hoffman S L, Ballou W R, Quakyi I A, Carter R, Trosper J H, and Hockmeyer W T (1986) Malaria transmitted to humans by mosquitoes infected from cultured *Plasmodium falciparum*. Am. J. Trop. Med. Hyg. 35: 66-68.

103. Epstein J E, Rao S, Williams F, Freilich D, Luke T, Sedegah M, de la Vega P, Sacci J, Richie T L, and Hoffman S L (2007) Safety and clinical outcome of experimental challenge of human volunteers with *Plasmodium falciparum*-infected mosquitoes: an update. J Infect Dis 196: 145-154.

104. Kester K E, McKinney D A, Tornieporth N, Ockenhouse C F, Heppner D G Jr, Hall T, Wellde B T, White K, Sun P, Schwenk R, Krzych U, Delchambre M, Voss G, Dubois M C, Gasser R A Jr, Dower M G, O'Brian M, Wittes J, Wirtz R, Cohen J, and Ballou W R (2007) A phase I/IIa safety, immunogenicity, and efficacy bridging randomized study of a two-dose regimen of liquid and lyophilized formulations of the candidate malaria vaccine RTS, S/AS02A in malaria-naive adults. Vaccine 25:5359-66.

105. Labaied, M., Harupa, A., Dumpit, R. F., Coppens, I., Mikolajczak, S. A., and Kappe, S. H. I., *Plasmodium yoelii* Sporozoites with Simultaneous Deletion of P52 and P36 are Completely Attenuated and Confer Sterile Immunity against Infection, *Infection and Immunity* (2007) 75(8):3758-68, published electronically ahead of print on May 21, 2007.

106. Trager, W. and J. B. Jenson, Cultivation of malarial parasites. Nature, 1978. 273(5664): p. 621-2.

107. Mercer, D. F., et al., Hepatitis C virus replication in mice with chimeric human livers. Nat Med, 2001. 7(8): p. 927-33.

108. Tsuboi, T., et al., Wheat germ cell-free system-based production of malaria proteins for discovery of novel vaccine candidates. Infect Immun, 2008. 76(4): p. 1702-8.

109. Fidock, D. A. and T. E. Wellems, Transformation with human dihydrofolate reductase renders malaria parasites insensitive to WR99210 but does not affect the intrinsic activity of proguanil. Proc Natl Acad Sci USA, 1997. 94(20): p. 10931-6.

110. Stewart, M. J. and J. P. Vanderberg, Malaria sporozoites release circumsporozoite protein from their apical end and translocate it along their surface. J Protozool, 1991. 38(4): p. 411-21.

111. Sattabongkot, J., et al., Establishment of a human hepatocyte line that supports in vitro development of the exo-erythrocytic stages of the malaria parasites *Plasmodium falciparum* and *P. vivax*. Am J Trop Med Hyg, 2006. 74(5): p. 708-15.

112. Goodyer, I. D., et al., Purification of mature-stage *Plasmodium falciparum* by gelatine flotation. Ann Trop Med Parasitol, 1994. 88(2): p. 209-11.

113. Sina, B. J., et al. (1993) *Plasmodium falciparum* Sporozoite Immunization Protects against *Plasmodium berghei* Sporozoite Infection, Exp. Parasitol. 77:129-135.

114. Douradinha, B. et al. (2997) Genetically attenuated P36p-deficient *Plasmodium berghei* sporozoites confer long-lasting and partial cross-species protection, Int. J. Parasitol. 37(13):1511-9.

115. Sedegah, M. et al. (2007) Cross-protection between attenuated *Plasmodium berghei* and *P. yoelii* sporozoites, Parasite Immunol. 29(11):559-65.

While the preferred embodiment of the invention has been illustrated and described, it will be appreciated that various changes can be made therein without departing from the spirit and scope of the invention.

The embodiments of the invention in which an exclusive property or privilege is claimed are defined as follows:

1. A genetically attenuated live *Plasmodium falciparum* organism that is genetically engineered to disrupt the liver-stage-specific gene function of LSA-1.

* * * * *

UNITED STATES PATENT AND TRADEMARK OFFICE
CERTIFICATE OF CORRECTION

PATENT NO. : 8,168,166 B2
APPLICATION NO. : 12/116159
DATED : May 1, 2012
INVENTOR(S) : S. H. I. Kappe et al.

Page 1 of 1

It is certified that error appears in the above-identified patent and that said Letters Patent is hereby corrected as shown below:

On the Title Page

Item (75)  Delete "Stefan H. I. Kappe, Seattle, WA (US); Kai-Uwe C. Matuschewski, Berlin (DE); Ann-Kristin Mueller, Dossenheim (DE); Kelley van Buskirk, Columbia City, IN (US); Mehdi Labaied, Bainbridge Island, WA (US); Ahmed Sayed Ibrahim Aly, Seattle, WA (US); Alan Frederick Cowman, Melbourne (AU), Alexander Gerd Maier, Coburg (AU)"

should read

--Stefan H. I. Kappe, Seattle, WA (US); Kelley van Buskirk, Columbia City, IN (US); Alan Frederick Cowman, Melbourne (AU)--

Signed and Sealed this
Thirteenth Day of August, 2013

Teresa Stanek Rea
*Acting Director of the United States Patent and Trademark Office*